United States Patent
Zhu et al.

(10) Patent No.: US 11,787,863 B2
(45) Date of Patent: *Oct. 17, 2023

(54) MULTI-SPECIFIC ANTIBODIES AND METHODS OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Yi Zhu, Chengdu (CN); Ole Olsen, Everett, WA (US); Dong Xia, Redmond, WA (US); David Jellyman, Duvall, WA (US); Katrina Bykova, Seattle, WA (US); Anne-Marie K. Rousseau, Seattle, WA (US); Bill Brady, Bothell, WA (US); Blair Renshaw, Renton, WA (US); Brian Kovacevich, Snohomish, WA (US); Yu Liang, Redmond, WA (US); Zeren Gao, Redmond, WA (US)

(73) Assignees: SYSTIMMUNE, INC.; BAILI-BIO (CHENGDU) PHARMACEUTICAL CO., LTD., Chengdu (CN)

(*) Notice: Subject to any disclaimer, the term of this patent is extended or adjusted under 35 U.S.C. 154(b) by 646 days.

This patent is subject to a terminal disclaimer.

(21) Appl. No.: 16/615,122

(22) PCT Filed: Jun. 22, 2018

(86) PCT No.: PCT/US2018/038156
§ 371 (c)(1),
(2) Date: Nov. 19, 2019

(87) PCT Pub. No.: WO2019/005639
PCT Pub. Date: Jan. 3, 2019

(65) Prior Publication Data
US 2022/0002406 A1    Jan. 6, 2022

Related U.S. Application Data

(60) Provisional application No. 62/524,557, filed on Jun. 25, 2017.

(51) Int. Cl.
*C07K 16/28* (2006.01)
*A61P 35/02* (2006.01)

(52) U.S. Cl.
CPC .......... *C07K 16/2809* (2013.01); *A61P 35/02* (2018.01); *C07K 16/2803* (2013.01); *C07K 16/2827* (2013.01); *C07K 16/2863* (2013.01); *C07K 16/2878* (2013.01); *C07K 2317/31* (2013.01); *C07K 2317/52* (2013.01); *C07K 2317/55* (2013.01); *C07K 2317/622* (2013.01); *C07K 2317/92* (2013.01)

(58) Field of Classification Search
CPC ............ C07K 2317/52; C07K 2317/31; C07K 16/2803
USPC ....................................................... 424/135.1
See application file for complete search history.

(56) References Cited

U.S. PATENT DOCUMENTS

| | | | |
|---|---|---|---|
| 2011/0182905 A1 | 7/2011 | Takada et al. | |
| 2014/0271464 A1 | 9/2014 | Garcia-Martinez et al. | |
| 2016/0355600 A1 | 12/2016 | Moore et al. | |
| 2020/0157224 A1* | 5/2020 | Zhu | C07K 16/32 |
| 2021/0024630 A1* | 1/2021 | Zhu | A61P 35/02 |
| 2022/0002425 A1* | 1/2022 | Zhu | A61K 47/6901 |

FOREIGN PATENT DOCUMENTS

| | | |
|---|---|---|
| WO | WO2009132037 A1 | 10/2009 |
| WO | WO2014/206561 A1 | 12/2014 |
| WO | WO2015/058861 A1 | 4/2015 |
| WO | WO2015/127288 A1 | 8/2015 |

OTHER PUBLICATIONS

Edwards et al. (J. Mol. Biol. (2003) 334, 103-118).*
Lloyd et al., (Protein Engineering, Design & Selection vol. 22 No. 3 pp. 159-168, 2009).*
Vajdos et al. (J Mol Biol. Jul. 5, 2002;320(2):415-28).*

* cited by examiner

*Primary Examiner* — Lynn A Bristol
(74) *Attorney, Agent, or Firm* — Feng Wan

(57) ABSTRACT

The disclosure provides a tetra-specific antibody monomer having a N-terminal and a C-terminal, comprising in tandem from the N-terminal to the C-terminal, a first scFv domain at the N-terminal, a Fab domain, a Fc domain, a second scFv domain, and a third scFv at the C-terminal, wherein the first scFv domain, the Fab domain, the second scFv domain, and the third scFv domain each has a binding specificity against a different antigen. In one embodiment, the antigen is a tumor antigen, an immune signaling antigen, or a combination thereof. Multi-specific antibodies comprising the disclosed tetra-specific antibodies are also provided.

16 Claims, 13 Drawing Sheets

Specification includes a Sequence Listing.

FIGURE 1. Tetraspecific antibody structure.
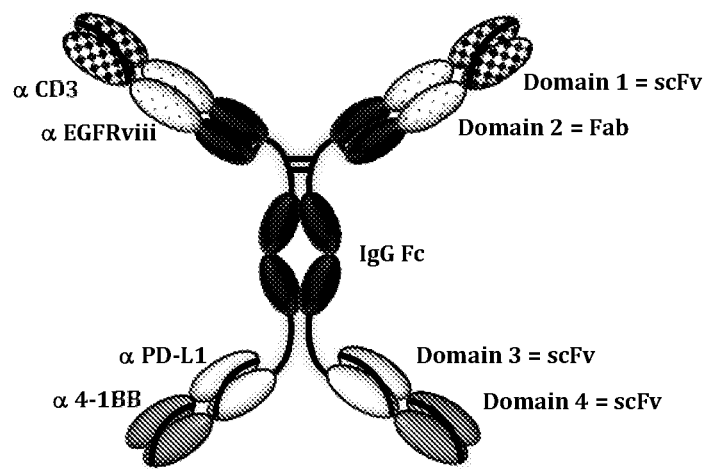

FIGURE 2. Redirected PBMC cytotoxicity against astrocytoma cell line U87 that was transfected with EGFRvIII.
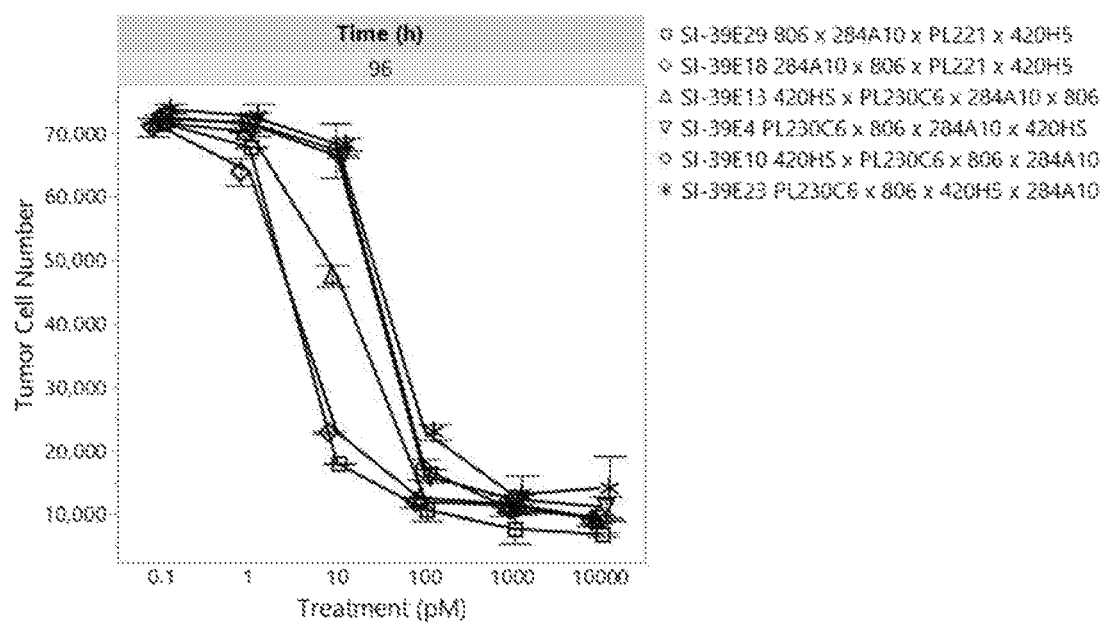

FIGURE 3. Redirected PBMC cytotoxicity against acute lymphoblastic leukemia cell line Kasumi-2.
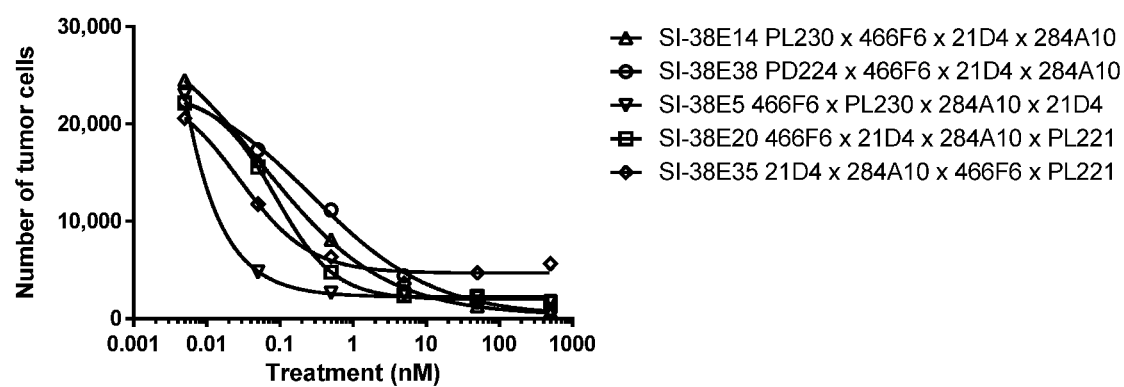

FIGURE 4. Redirected PBMC cytotoxicity against astrocytoma cell line U87 that was transfected with EGFRvIII. Functional activity of different 4-1BB domains. Functional impact of PD-L1 and 4-1BB domains.
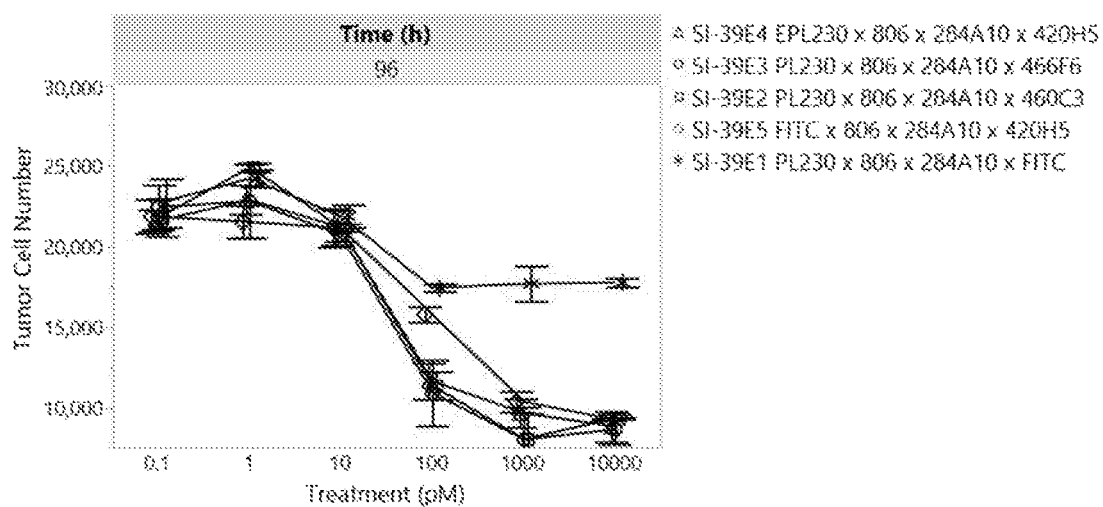

FIGURE 5. Tetraspecific antibodies binding to human ROR1 transfected CHO cells.
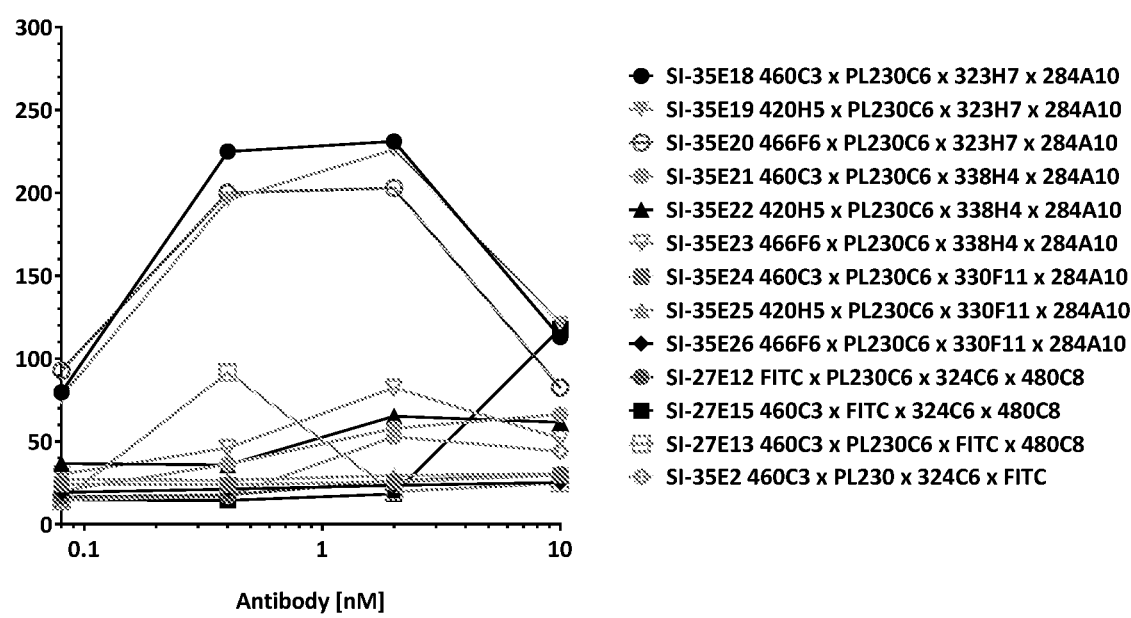

FIGURE 6. Tetraspecific antibodies binding to human 41BB transfected CHO cells.
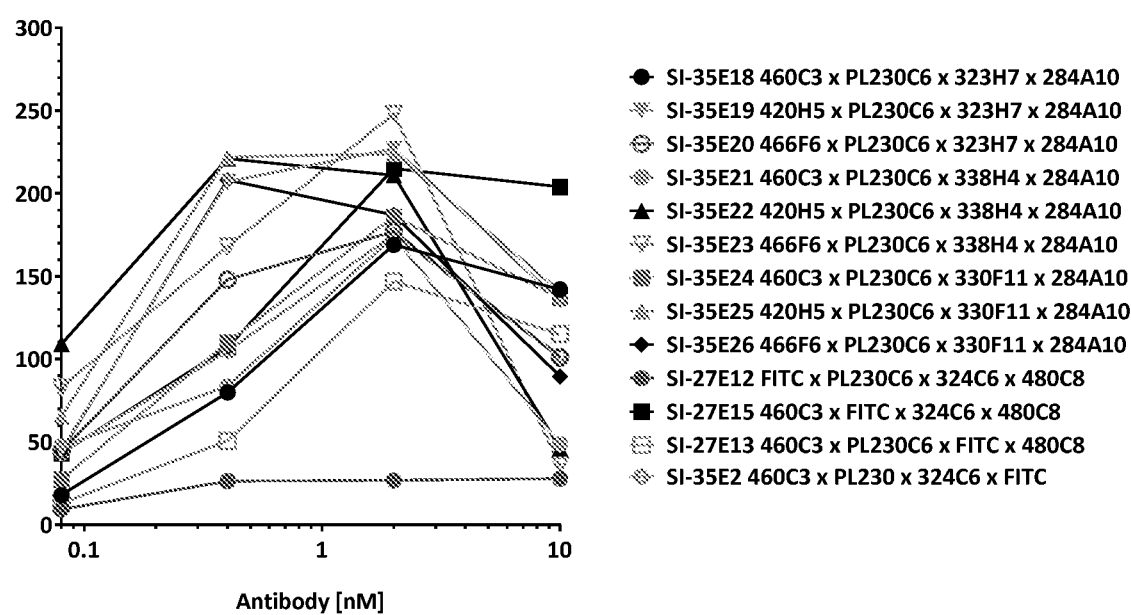

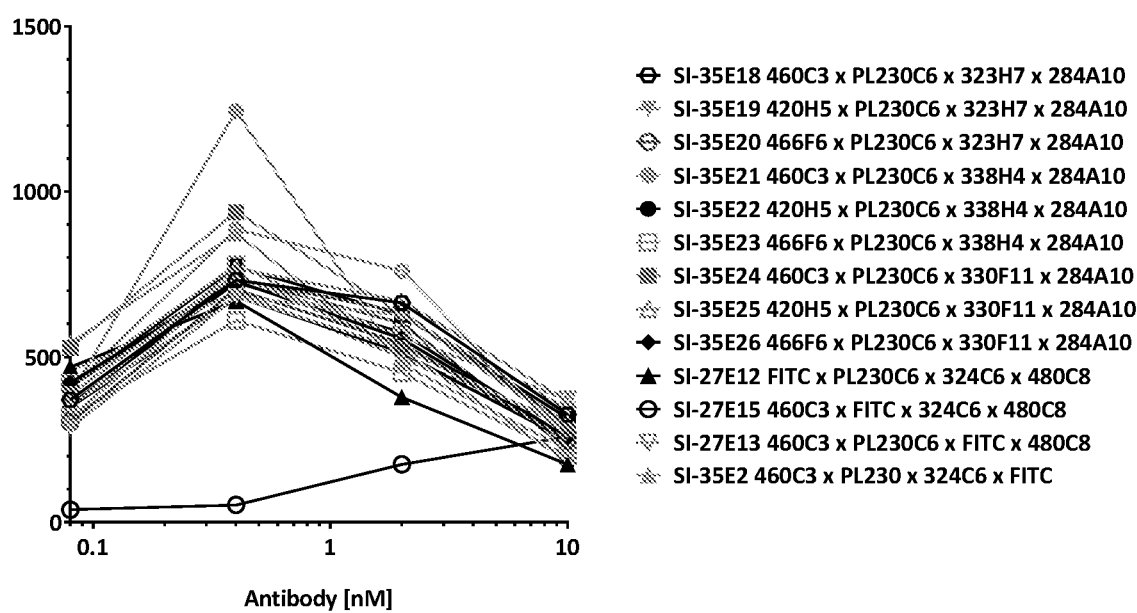
FIGURE 7. Tetraspecific antibodies binding to human PD-L1 transfected CHO cells.

FIGURE 8. Tetraspecific antibodies with the binding domain 323H7 which is specific for the Ig domain of ROR1 meditated RTCC of the B-ALL cell line Kasumi2 with PBMC as effectors.
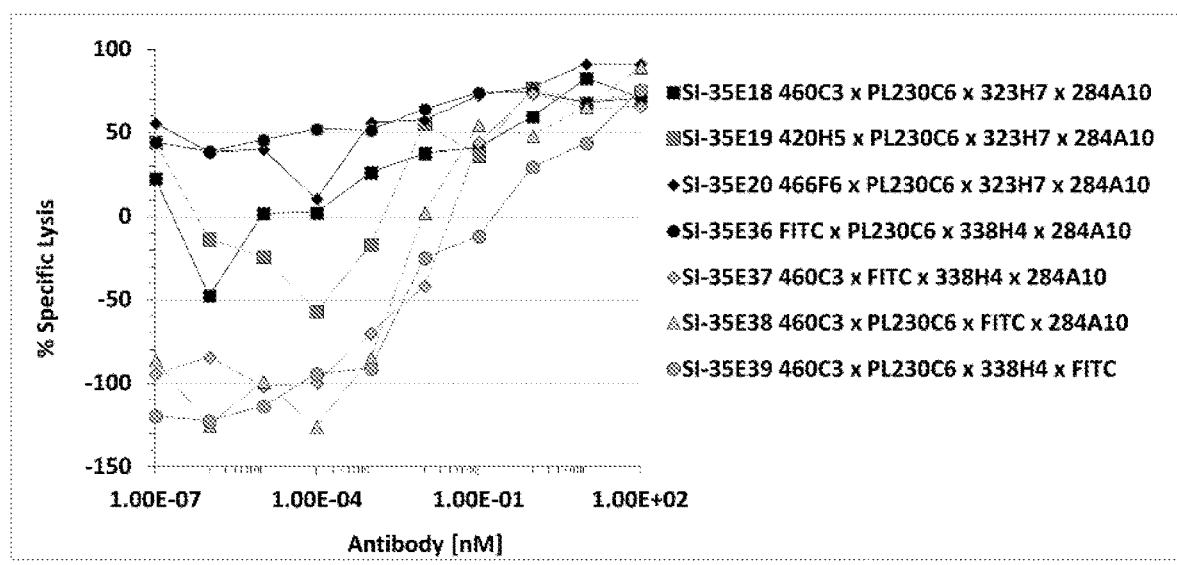

FIGURE 9. Tetraspecific antibodies with the binding domain 323H7 which is specific for the Ig domain of ROR1 meditated RTCC of the B-ALL cell line Kasumi2 with CD8+, CD45RO+ memory T cells as effectors.
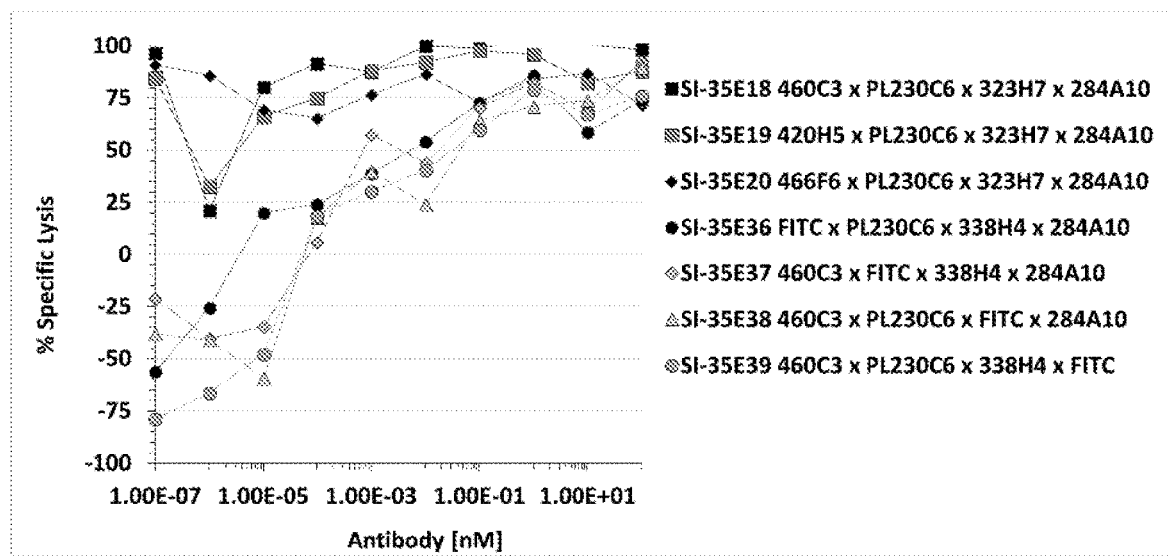

FIGURE 10. Tetraspecific antibodies with the binding domain 323H7 which is specific for the Ig domain of ROR1 meditated RTCC of the B-ALL cell line Kasumi2 with CD8+, CD45RA+ naive T cells as effectors.
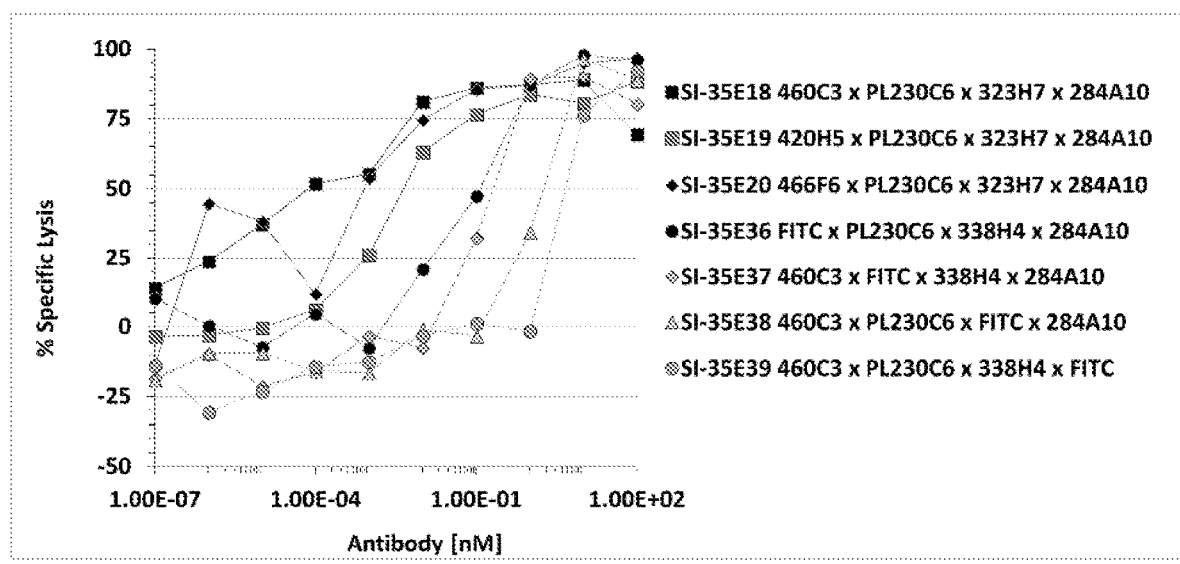

FIGURE 11. Tetraspecific antibodies with the binding domain 338H4 which is specific for the Frizzled domain of ROR1 meditated RTCC of the B-ALL cell line Kasumi2 with PBMC as effectors.
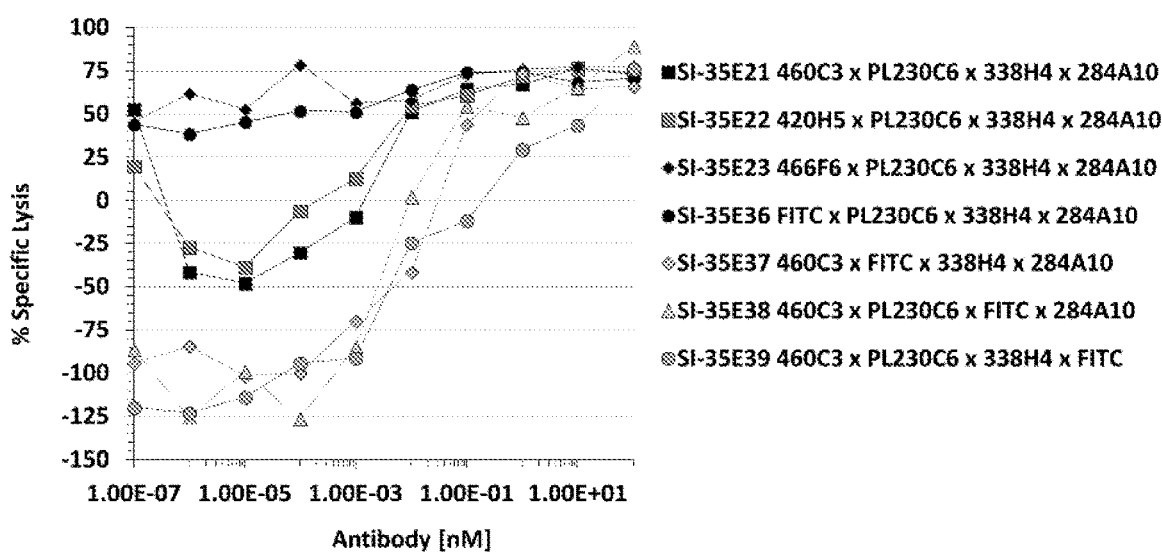

FIGURE 12. Tetraspecific antibodies with the binding domain 338H4 which is specific for the Frizzled domain of ROR1 meditated RTCC of the B-ALL cell line Kasumi2 with CD8+, CD45RO+ memory T cells as effectors.
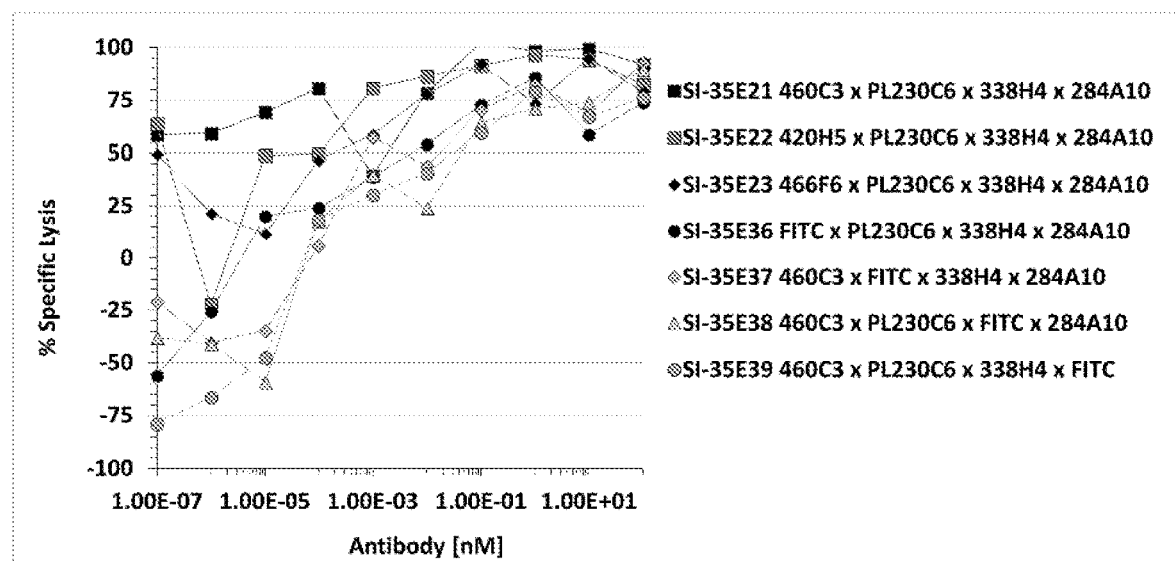

FIGURE 13. Tetraspecific antibodies with the binding domain 338H4 which is specific for the Frizzled domain of ROR1 meditated RTCC of the B-ALL cell line Kasumi2 with CD8+, CD45RA+ naive T cells as effectors.
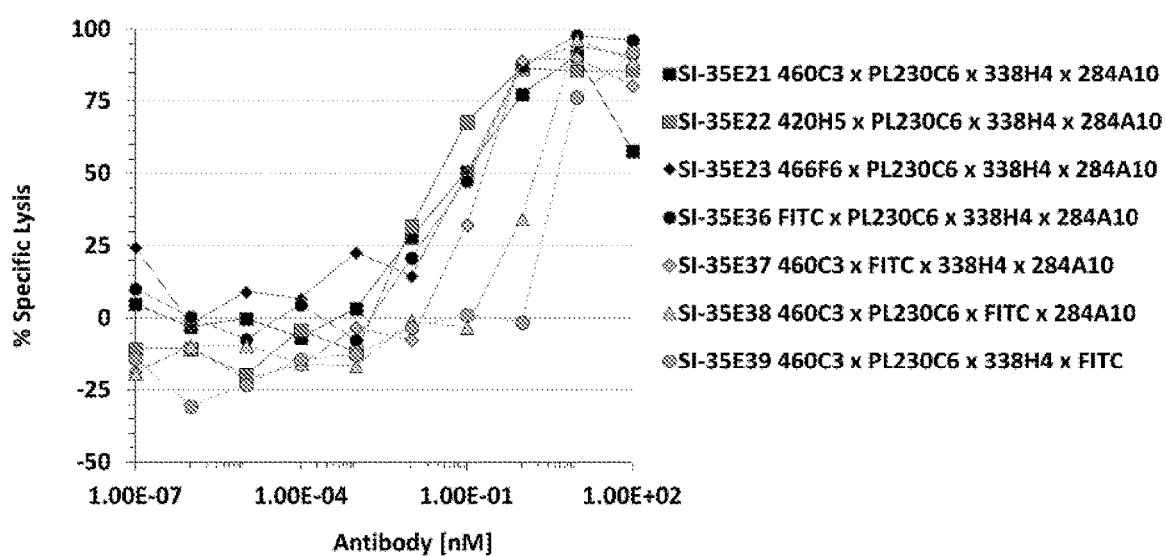

MULTI-SPECIFIC ANTIBODIES AND METHODS OF MAKING AND USING THEREOF

CROSS REFERENCE TO RELATED APPLICATIONS

This application claims the benefit of U.S. Provisional Patent Application No. 62/524,557 filed Jun. 25, 2017, which application is expressly incorporated herein by reference in its entirety.

TECHNICAL FIELD

The present disclosure generally relates to the technical field of biologic therapeutics, and more particularly relates to making and using multi-specific antibodies.

BACKGROUND

Cancer cells develop various strategies to evade the immune system. One of the underlying mechanisms for the immune escape is the reduced recognition of cancer cells by the immune system. Defective presentation of cancer specific antigens or lack of thereof results in immune tolerance and cancer progression. In the presence of effective immune recognition tumors use other mechanisms to avoid elimination by the immune system. Immunocompetent tumors create suppressive microenvironment to downregulate the immune response. Multiple players are involved in shaping the suppressive tumor microenvironment, including tumor cells, regulatory T cells, Myeloid-Derived Suppressor cells, stromal cells, and other cell types. The suppression of immune response may be executed in a cell contact-dependent format as well as in and a contact-independent manner, via secretion of immunosuppressive cytokines or elimination of essential survival factors from the local environment. Cell contact-dependent suppression relies on molecules expressed on the cell surface, e.g. Programmed Death Ligand 1 (PD-L1), T-lymphocyte-associated protein 4 (CTLA-4) and others [Dunn, et al., 2004, Immunity, 21(2): 137-48; Adachi & Tamada, 2015, Cancer Sci., 106(8): 945-50].

As the mechanisms by which tumors evade recognition by the immune system continue to be better understood new treatment modalities that target these mechanisms have recently emerged. On Mar. 25, 2011, the U. S. Food and Drug Administration (FDA) approved ipilimumab (anti-CTLA-4 monoclonal antibody, YERVOY®, Bristol-Myers Squibb) injection for the treatment of unresectable or metastatic melanoma. YERVOY® binds to cytotoxic T-lymphocyte-associated protein 4 (CTLA-4) expressed on activated T cells and blocks the interaction of CTLA-4 with CD80/86 on antigen-presenting cells thereby blocking the negative or inhibitory signal delivered into the T cell through CTLA-4 resulting in re-activation of the antigen-specific T cell leading to, in many patients, eradication of the tumor. A few years later in 2014 the FDA approved KEYTRUDA® (anti-PD1 monoclonal antibody, Pembrolizumab, Merck) and OPDIVO® (anti-PD1 monoclonal antibody, Nivolumab, Bristol-Myers Squibb) for treatment of advanced melanoma. These monoclonal antibodies bind to PD-1 which is expressed on activated and/or exhausted T cells and block the interaction of PD-1 with PD-L1 expressed on tumors thereby eliminating the inhibitory signal through PD-1 into the T cell resulting in re-activation of the antigen-specific T cell leading to again, in many patients, eradication of the tumor. Since then additional clinical trials have been performed comparing the single monoclonal antibody Yervoy® to the combination of the monoclonal antibodies YERVOY® and OPDIVO® in the treatment of advanced melanoma which showed improvement in overall survival and progression-free survival in the patients treated with the combination of antibodies. (Hodi et al., 2016, Lancet Oncol. 17(11):1558-1568, Hellman et al., 2018, Cancer Cell 33(5): 853-861). However, as many clinical trials have shown a great benefit of treating cancer patients with monoclonal antibodies that are specific for one or more immune checkpoint molecules data has emerged that only those patients with a high mutational burden that generates a novel T cell epitope(s) which is recognized by antigen-specific T cells show a clinical response (Snyder et al., 2014, NEJM 371: 2189-2199). Those patients that have a low tumor mutational load mostly do not show an objective clinical response (Snyder et al., 2014, NEJM 371:2189-2199, Hellman et al., 2018, Cancer Cell 33(5): 853-861).

In recent years, other groups have developed an alternate approach that does not require the presence of neoepitope presentation by antigen-presenting cells to activate T cells. One example is the development of a bi-specific antibody where the binding domain of an antibody which is specific for a tumor associated antigen, e.g., CD19, is linked to and antibody binding domain specific for CD3 on T cells thus creating a bi-specific T cell engager or BiTe molecule. In 2014, the FDA approved a bi-specific antibody called Blinatumomab (bispecific anti-CD3×CD19 monoclonal antibody, BLINCYTO®; Amgen) for the treatment of Precursor B-Cell Acute Lymphoblastic Leukemia. Blinatumomab links the scFv specific for CD19 expressed on leukemic cells with the scFv specific for CD3 expressed on T cells (Bejnjamin and Stein 2016, Ther Adv Hematol 7(3):142-146). However, despite an initial response rate of >50% in patients with relapsed or refractory ALL many patients are resistant to Blinatumomab therapy or relapse after successful treatment with Blinatumomab. Evidence is emerging that the resistant to Blinatumomab or who relapse after Blinatumomab treatment is attributable to the expression of immune checkpoint inhibitory molecules expressed on tumor cells such as PD-L1 that drives an inhibitory signal through PD-1 expressed on activated T cells (Feucht et al., 2016, Oncotarget 7(47):76902-76919). In a case study of a patient who was resistant to therapy with Blinatumomab a second round of Blinatumomab therapy was performed but with the addition of a monoclonal antibody, pembrolizumab (KEYTRUDA®, Merck), which specific for PD-1 and blocks the interaction of T cell-expressed PD-1 with tumor cell expressed PD-L1 resulted in a dramatic response and reduction of tumor cells in the bone marrow from 45% to less than 5% in this one patient (Feucht et al., 2016, Oncotarget 7(47):76902-76919). These results show that combining a bi-specific BiTe molecule with one or more monoclonal antibodies may significantly increase clinical activity compared to either agent alone.

SUMMARY

The present disclosure provides, among others, tetra-specific antibody monomers, antibodies containing tetra-specific monomers, antigen-binding fragments thereof, multi-specific antibodies, immuno-conjugates comprising the disclosed antibodies, methods of making disclosed monomers, antigen-binding fragments, and antibodies, and methods of using the disclosed molecules for treating cancer.

In one aspect, the application provides tetra-specific antibody monomers. In one embodiment, the tetra-specific antibody monomer has a N-terminal and a C-terminal and include in tandem from the N-terminal to the C-terminal, a first scFv domain at the N-terminal, a Fab domain, a Fc domain, a second scFv domain, and a third scFv at the C-terminal. The first scFv domain, the Fab domain, the second scFv domain, and the third scFv domain each has a binding specificity against a different antigen.

In one embodiment, the antigen includes a tumor antigen, an immune signalling antigen, or a combination thereof. In one embodiment, the first scFv domain, the Fab domain, the second scFv domain, and the third scFv domain each has a binding specificity against a tumor antigen or an immune signalling antigen. In one embodiment, the first scFv domain has a binding specificity against a tumor antigen. In one embodiment, the first scFv domain has a binding specificity against an immune signalling antigen. In one embodiment, the Fab domain has a binding specificity against a tumor antigen. In one embodiment, the Fab domain has a binding specificity against an immune signalling antigen. In one embodiment, the second scFv domain has a binding specificity against a tumor antigen. In one embodiment, the second scFv domain has a binding specificity against an immune signalling antigen. In one embodiment, the third scFv domain has a binding specificity against a tumor antigen. In one embodiment, the third scFv domain has a binding specificity against a tumor antigen.

In one embodiment, the tetra-specific monomer includes the scFv domain, the Fab domain, the second scFv domain, and the third scFv domain each independently has a binding specificity against an antigen selected from ROR1, PD-L1, CD3, CD28, 4-1BB, CEA, HER2, EGFR VIII, EGFR, LMP1, LMP2A, Mesothelin, PSMA, EpCAM, glypimay-3, gpA33, GD2, TROP2, NKG2D, BCMA, CD19, CD20, CD33, CD123, CD22, CD30, PD-L1, PD1, OX40, 4-1BB, GITR, TIGIT, TIM-3, LAG-3, CTLA4, CD40, VISTA, ICOS, BTLA, LIGHT, HVEM, CSF1R, CD73, and CD39. In one embodiment, the scFv domain, the Fab domain, the second scFv domain, and the third scFv domain each independently has a binding specificity against tumor specific antigens including, but not limited to, ROR1, CEA, HER2, EGFR, EGFR VIII, LMP1, LMP2A, Mesothelin, PSMA, EpCAM, glypimay-3, gpA33, GD2, TROP2, BCMA, CD3, CD19, CD20, CD33, CD123, CD22, CD30, or immune checkpoint modulators including, without limitation, PD-L1, PD1, OX40, 4-1BB, GITR, TIGIT, TIM-3, LAG-3, CTLA4, CD40, VISTA, ICOS, BTLA, Light, HVEM, CD73, CD39, etc. In one embodiment, one set of scFv domain may specifically bind to an immune checkpoint modulators or a tumor antigen. In one embodiment, the scFv specific to CD3 may be on either C or N terminal of heavy or light chains.

In one embodiment, the first scFv domain, the Fab domain, the second scFv domain, and the third scFv domain each independently has a binding specificity against an antigen selected from CD3, EGRF EGFRvlll, PD-L1, and 4-1BB. In one embodiment, the first scFv domain has a binding specificity against CD3. In one embodiment, the Fab domain has a binding specificity against EGRF EGFRvlll. In one embodiment, the second scFv domain has a binding specificity against PD-L1. In one embodiment, the third scFv domain has a binding specificity against 4-1BB. In one embodiment, the first scFv domain has a binding specificity against CD3, the Fab domain has a binding specificity against EGRF EGFRvlll, the second scFv domain has a binding specificity against PD-L1, and the third scFv domain has a binding specificity against 4-1BB.

Fc domain may be humanized. In one embodiment, the Fc domain is a human IgG1 Fc.

The scFv domain may include a linker linking the scFv domain to the heavy chain or light chain of the antibody. In one embodiment, the linker may include more than 10 amino acids. In one embodiment, the linker may include more than 15 amino acids long. In one embodiment, the linker may include less than 20 amino acids.

In one embodiment, the linker may comprise a gly-gly-gly-gly-ser (G4S)n linker, and n may be an integral between 1 to 20. For example, n may be 2, 4, or 6. In one embodiment, the first scFv domain, the second scFv domain, or the third scFv domain may comprise a gly-gly-gly-gly-ser (G4S)n linker, wherein n is 2 or 4.

In one embodiment, the application provides a tetra-specific antibody monomers having an amino acid sequence having a percentage homology to SEQ ID NO. 02, 04, 06, 08, 10, 12, 14, 16, 18, 20, 22, 24, 26, 28, 30, 32, 34, 36, 38, 40, 42, 44, 46, 48, 50, 52, 54, 56, 58, and 60. The percentage homology is not less than 70%, 80%, 90%, 95%, 98% or 99%.

The application further provides antigen-binding fragments. In one embodiment, the application provides scFv domains. In one embodiment, the scFv domain has an amino acid sequence having a percentage homology to SEQ ID NO. 02, 04, 06, 08, 10, 12, 14, 16, 18, 20, 22, 24, 26, 28, 30, 32, 34, 36, 38, 40, 42, 44, 46, 48, 50, 52, 54, 56, 58, and 60, wherein the percentage homology is not less than 70%, 80%, 90%, 95%, 98% or 99%. In one embodiment, the application provides Fab domains. In one embodiment, the Fab domain includes an amino acid sequence having a percentage homology to SEQ ID NO. 02, 04, 06, 08, 10, 12, 14, 16, 18, 20, 22, 24, 26, 28, 30, 32, 34, 36, 38, 40, 42, 44, 46, 48, 50, 52, 54, 56, 58 and 60, wherein the percentage homology is not less than 70%, 80%, 90%, 95%, 98% or 99%. The antigen-binding fragments disclosed herein may be used to construct the tetra-specific antibody monomers or multi-specific antibodies.

In one aspect, the application provides multi-specific antibodies. In one embodiment, the multi-specific antibody includes tetra-specific antibody monomers. In one embodiment, the multi-specific antibody includes two tetra-specific antibody monomers disclosed herein. As each tetra-specific antibody monomer has four antigen-binding domains, the multi-specific antibody disclosed may include 8 antigen-binding domains. In one embodiment, the antigen binding domains in such multi-specific antibody each independently has a binding specificity against a different antigen therefor providing an octa-specific antibody. In one embodiment, the multi-specific antibody is a penta-specific antibody. In one embodiment, the multi-specific antibody is a penta-specific antibody. In one embodiment, the multi-specific antibody is a penta-specific antibody a hexa-specific antibody. In one embodiment, the multi-specific antibody is a penta-specific antibody a hepta-specific antibody.

In one embodiment, the multi-specific antibody includes a dimer of a tetra-specific antibody monomer therefor providing a tetra-specific antibody. In one embodiment, the application provides an isolated, purified, or non-natural existing multi-specific antibodies. In one embodiment, the application provides a tetra-specific antibody having an amino acid sequence having a percentage homology to SEQ ID 66 and 68. The percentage homology is not less than 70%, 80%, 90%, 95%, 98% or 99%.

The application further provides isolated nucleic acid sequence encoding the tetra-specific antibody monomers, the multi-specific antibodies, or the antigen-binding fragments thereof. In one embodiment, the nucleic acid encodes an amino acid sequence having a percentage homology to the tetra-specific antibody monomer having a SEQ ID NO. 01, 03, 05, 07, 09, 11, 13, 15, 17, 19, 21, 23, 25, 27, 29, 31, 33, 35, 37, 39, 41, 43, 45, 47, 49, 51, 53, 55, 57, and 59. The percentage homology is not less than 70%, 80%, 90%, 95%, 98% or 99%.

The application further provides expression vectors and host cells comprising the nucleic acid sequences disclosed herein. In one embodiment, the host cell includes the expression vector. The host cell may be a prokaryotic cell or a eukaryotic cell.

The application further provides immuno-conjugates. In one embodiment, the immuno-conjugate includes a cytotoxic agent or an imaging agent linked to the multi-specific antibody disclosed herein through a linker.

The linker may be cleavable or non-cleavable. The linker may include a covalent bond such as an ester bond, an ether bond, an amid bond, a disulphide bond, an imide bond, a sulfone bond, a phosphate bond, a phosphorus ester bond, a peptide bond, or a combination thereof. In one embodiment, the linker comprises a hydrophobic poly(ethylene glycol) linker.

The cytotoxic agent may include a chemotherapeutic agent, a growth inhibitory agent, a cytotoxic agent from class of calicheamicin, an antimitotic agent, a toxin, a radioactive isotope, a therapeutic agent, or a combination thereof. In one embodiment, the cytotoxic agent comprises a calicheamicin, ozogamicin, monomethyl auristatin E, emtansine, a derivative or a combination thereof.

The imaging agent may be any compound useful for imaging purpose. In one embodiment, the imaging agent may be radionuclide, a florescent agent, a quantum dots, or a combination thereof.

The application further provides pharmaceutical composition. In one embodiment, the pharmaceutical composition comprises a pharmaceutically acceptable carrier and the tetra-specific antibody monomer disclosed herein. In one embodiment, the pharmaceutical composition comprises a pharmaceutically acceptable carrier and the multi-specific antibody disclosed herein. In one embodiment, the pharmaceutical composition comprises a pharmaceutically acceptable carrier and the antigen-binding fragment disclosed herein. In one embodiment, the pharmaceutical composition comprises a pharmaceutically acceptable carrier and the immuno-conjugate disclosed herein.

In one embodiment, the pharmaceutical composition further includes a therapeutic agent. Example therapeutic agents include without limitation a radioisotope, radionuclide, a toxin, a chemotherapeutic agent or a combination thereof. In one embodiment, the therapeutic agent comprises an antibody, an enzyme, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In one embodiment, the therapeutic agent comprises a check point inhibitor. In one embodiment, the therapeutic agent comprises an inhibitor of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In a further aspect, the application provides methods for making the tetra-specific antibody monomers, the multi-specific antibodies, the antigen-binding fragments thereof, and immuno-conjugates thereof. In one embodiment, the method includes the steps of culturing the host cell containing the nucleic acid sequences disclosed herein such that the DNA sequence encoding the antibody is expressed and purifying the antibody. In one embodiment, the antibody is a tetra-specific antibody.

In a further aspect, the application provides methods of using the tetra-specific antibody monomers, the multi-specific antibodies, the antigen-binding fragments thereof, and immuno-conjugates thereof for cancer treatment. In one embodiment, the method includes the step of administering tetra-specific antibody monomers, the multi-specific antibodies, the antigen-binding fragments thereof, and immuno-conjugates thereof, or pharmaceutical composition thereof to a subject in need of such treatment. In one embodiment, the method includes the step of administering to the subject an effective amount of the tetra-specific antibody.

In one embodiment, the method includes directly injecting into the tumour site an effective amount of multi-specific monomers, multi-specific antibodies, the immuno-conjugates, the antigen-binding fragment thereof.

Varieties of cancer may be prevented or treated. In one embodiment, the cancer may have cells expressing ROR1, CEA, HER2, EGFR, EGFR VIII, LM P1, LMP2A, Mesothelin, PSMA, EpCAM, glypimay-3, gpA33, GD2, TROP2, NKG2D, BCMA, CD19, CD20, CD33, CD123, CD22, or CD30. Example cancers include without limitation breast cancer, colorectal cancer, anal cancer, pancreatic cancer, gallbladder cancer, bile duct cancer, head and neck cancer, nasopharyngeal cancer, skin cancer, melanoma, ovarian cancer, prostate cancer, urethral cancer, lung cancer, non-small lung cell cancer, small cell lung cancer, brain tumor, glioma, neuroblastoma, oesophageal cancer, gastric cancer, liver cancer, kidney cancer, bladder cancer, cervical cancer, endometrial cancer, thyroid cancer, eye cancer, sarcoma, bone cancer, leukemia, myeloma or lymphoma.

In one embodiment, the method may further include co-administering an effective amount of a therapeutic agent. In one embodiment, the therapeutic agent may include an antibody, a chemotherapy agent, an enzyme, or a combination thereof. In one embodiment, the therapeutic agent may include an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In one embodiment, the therapeutic agent may include a check point inhibitor. In one embodiment, the therapeutic agent may include an inhibitor of PD1, PD-L1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In one embodiment, the therapeutic agent may comprises capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, a derivative or a combination thereof.

The subject may be a human. In one embodiment, the subject may be suffering from cancer. The application further provides solutions comprising an effective concentration of the multi-specific antibodies, monomers, or immunoconjugates disclosed herein. In one embodiment, the solution is blood plasma in a subject.

The objectives and advantages of the disclosure may become apparent from the following detailed description of example embodiments thereof in connection with the accompanying drawings. Still other embodiments may become readily apparent to those skilled in the art from the following detailed description, wherein are described embodiments by way of illustrating the best mode contemplated. As may be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF FIGURES

The foregoing and other features of this disclosure may become more fully apparent from the following description and appended claims, taken in conjunction with the accompanying drawings. Understanding that these drawings depict only several embodiments arranged in accordance with the disclosure and are, therefore, not to be considered limiting of its scope, the disclosure may be described with additional specificity and detail through use of the accompanying drawings, in which:

FIG. 1 is a diagram of a tetra-specific antibody with Domains 1-4 as antigen binding domains. CD3×EGFRvlll×PD-L1×4-1BB tetra-specific antibody is shown as an example in accordance to one embodiment.

FIG. 2 depicts experiment results showing Redirected PBMC (peripheral blood mononuclear cells) cytotoxicity against astrocytoma cell line U87 that was transfected with EGFRvlll. Tumor lysis activity of tetra-specific antibodies used is listed in TABLE 1.

FIG. 3 depicts experiment results showing Redirected PBMC (peripheral blood mononuclear cells) cytotoxicity against acute lymphoblastic leukemia cell line Kasumi-2.

FIG. 4 depicts experiment results showing Redirected PBMC (peripheral blood mononuclear cells) cytotoxicity against astrocytoma cell line U87 that was transfected with EGFRvlll. Functional activities of different 4-1BB domains and functional impact of PD-L1 and 4-1BB domains are shown.

FIG. 5 is a depiction of experiment results showing FACS analysis of tetra-specific antibodies binding to human ROR1 transfected CHO cells according to some embodiments.

FIG. 6 is a depiction of experiment results showing FACS analysis of tetra-specific antibodies binding to human 4-1BB transfected CHO cells according to some embodiments.

FIG. 7 is a depiction of experiment results showing FACS analysis of tetra-specific antibodies binding to human PD-L1 transfected CHO cells according to some embodiments.

FIG. 8 is a depiction of experiment results showing redirected T cell cytotoxicity (RTCC) assay, meditated by tetra-specific antibodies with the binding domain 323H7 which is specific for the Ig domain of ROR1, with peripheral blood mononuclear cells as effectors and the B-ALL cell line Kasumi2 as targets according to some embodiments.

FIG. 8 is a depiction of experiment results showing redirected T cell cytotoxicity (RTCC) assay, meditated by tetra-specific antibodies with the binding domain 323H7 which is specific for the Ig domain of ROR1, with peripheral blood mononuclear cells as effectors and the B-ALL cell line Kasumi2 as targets according to some embodiments.

FIG. 9 is a depiction of experiment results showing redirected T cell cytotoxicity (RTCC) assay, meditated by tetra-specific antibodies with the binding domain 323H7 which is specific for the Ig domain of ROR1, with CD8+, CD45RO+ memory T cells as effectors and the B-ALL cell line Kasumi2 as targets according to some embodiments.

FIG. 10 is a depiction of experiment results showing redirected T cell cytotoxicity (RTCC) assay, meditated by tetra-specific antibodies with the binding domain 323H7 which is specific for the Ig domain of ROR1, with CD8+, CD45RA+naive T cells as effectors and the B-ALL cell line Kasumi2 as targets according to some embodiments.

FIG. 11 is a depiction of experiment results showing redirected T cell cytotoxicity (RTCC) assay, meditated by tetra-specific antibodies with the binding domain 338H4 which is specific for the Frizzled domain of ROR1, with peripheral blood mononuclear cells as effectors and the B-ALL cell line Kasumi2 as targets according to some embodiments.

FIG. 12 is a depiction of experiment results showing redirected T cell cytotoxicity (RTCC) assay, meditated by tetra-specific antibodies with the binding domain 338H4 which is specific for the Frizzled domain of ROR1, with CD8+, CD45RO+ memory T cells as effectors and the B-ALL cell line Kasumi2 as targets according to some embodiments.

FIG. 13 is a depiction of experiment results showing redirected T cell cytotoxicity (RTCC) assay, meditated by tetra-specific antibodies with the binding domain 338H4 which is specific for the Frizzled domain of ROR1, with CD8+, CD45RA+naive T cells as effectors and the B-ALL cell line Kasumi2 as targets according to some embodiments.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It may be readily understood that the aspects of the present disclosure, as generally described herein, and illustrated in the FIGs, may be arranged, substituted, combined, separated, and designed in a wide variety of different configurations, all of which are explicitly contemplated herein.

The disclosure provides, among others, isolated antibodies, methods of making such antibodies, tetra-specific or multi-specific molecules, antibody-drug conjugates and/or immuno-conjugates composed from such antibodies or antigen binding fragments, pharmaceutical compositions containing the antibodies, tetra-specific or multi-specific molecules, antibody-drug conjugates and/or immuno-conjugates, method of making thereof, and method of using the disclosed molecules or composition for treatment of cancer.

The term "antibody" is used in the broadest sense and specifically covers single monoclonal antibodies (including agonist and antagonist antibodies), antibody compositions with polyepitopic specificity, as well as antibody fragments (e.g., Fab, F(ab')2, and Fv), so long as they exhibit the desired biological activity. In some embodiments, the antibody may be monoclonal, polyclonal, chimeric, single chain, tetra-specific or bi-effective, simianized, human and humanized antibodies as well as active fragments thereof. Examples of active fragments of molecules that bind to known antigens include Fab, F(ab')2, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin may be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to hetero-tetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions may be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies may be advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, *Nature,* 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 [1984]).

Monoclonal antibodies may be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with both human PD-L1 protein and cells transiently expressing human PD-L1 on the cell surface. Rabbits are known to create antibodies of high affinity, diversity and specificity (Weber et al. Exp. Mol. Med. 49:e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9:e86184 (2014).

The term "antigen- or epitope-binding portion or fragment" refers to fragments of an antibody that are capable of binding to an antigen (PD-L1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments may be even smaller sub-fragments and may consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments may be screened for utility using the same techniques employed with intact antibodies.

The "antigen-or epitope-binding fragments" may be derived from an antibody of the present disclosure by a number of art-known techniques. For example, purified monoclonal antibodies may be cleaved with an enzyme, such as pepsin, and subjected to HPLC gel filtration. The appropriate fraction containing Fab fragments may then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')2 fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species may be assigned to one of two clearly distinct types, called kappa and lambda (λ), based on the amino acid sequences of their constant domains.

Depending on the amino acid sequence of the constant domain of their heavy chains, immunoglobulins may be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called a, delta, epsilon, γ, and µ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In some embodiments, framework support residues may be altered to preserve binding affinity. Methods to obtain "humanized antibodies" are well known to those skilled in the art. (see, e.g., Queen et al., *Proc. Natl Acad Sci USA*, 86:10029-10032 (1989), Hodgson et al., *Bio/Technology*, 9:421 (1991)).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide may be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which may induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding may be measured, for example, by determining binding of a molecule compared to binding of a control molecule, which generally is a molecule of similar structure that does not have binding activity. For example, specific binding may be determined by competition with a control molecule that is similar to the target.

Specific binding for a particular antigen or an epitope may be exhibited, for example, by an antibody having a KD for an antigen or epitope of at least about $10^{-4}$ M, at least about $10^{-9}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen may have a KD that is 20-, 50-, 100-, 500-, 1000-, 5,000-, 10,000- or more times greater for a control molecule relative to the antigen or epitope.

Also, specific binding for a particular antigen or an epitope may be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity may be determined conventionally with the use of computer programs. The deviations appearing in the comparison between a given sequence and the above-described sequences of the disclosure may be caused for instance by addition, deletion, substitution, insertion or recombination.

In one aspect, the application provides tetra-specific antibody monomers, antigen-binding fragments, and multi-specific antibodies. In one embodiment, the application provides tetra-specific antibodies.

In one embodiment, the disclosure provides tetra-specific antibodies with a binding specificity against four different antigen targets. In one embodiment, the antigen targets are tumor specific antigens, T cell receptor CD3 component, or immune checkpoint molecules. The tetra-specific antibodies may directly engage body's endogenous T cells to kill tumor cells independent of tumor antigen presentation by MHC to the antigen specific T cell receptors. In some embodiments, the immune checkpoint modulating component of the tetra-specific antibodies may overcome the immunosuppressive tumor microenvironment to fully activate the exhausted T cells within the tumor microenvironment.

The tetra-specific antibodies have unique properties of directly engaging T cells at the same time modulating immune checkpoint or inhibiting Treg or other inhibitory immune cells or targeting tumor with component against tumor antigens. It may show benefit to the patients where BiTE or CAR-T treatment isn't appropriate. In one embodiment, the tetra-specific antibodies could demonstrate clinical benefit in solid tumor where BiTE-like technology or CAR-T treatment yet to show clinical benefit due to the limitations imposed by the inhibitory tumor microenvironment.

In one embodiment, the application provides an engineered antibody with 4 different binding domains or a "tetra-specific antibody". One binding domain is specific for CD3 on T cells, a second binding domain is specific for a tumor associated antigen including but not limited to ROR1, CEA, HER2, EGFR, EGFRvlll, LMP1, LMP2A, Mesothelin, PSMA, EpCAM, glypimay-3, gpA33, GD2, TROP2, BCMA, CD19, CD20, CD33, CD123, CD22, CD30, and a third and fourth binding domains are specific for two distinct immune checkpoint modulators such as PD-L1, PD-1, OX40, 4-1BB, GITR, TIGIT, TIM-3, LAG-3, CTLA4, CD40, VISTA, ICOS, BTLA, Light, HVEM, CD73, CD39, etc.

An example tetra-specific molecules disclosed herein (FIG. 1) target either human ROR1 (SEQIDs 33-48), human CD19 (SEQIDs 53-56) or EGFR vlll (SEQIDs 49-52) as tumor associated antigens. Each of these targeted tetra-specific proteins also carries an anti-human PD-L1 (SEQIDs 9-16), an anti-human 4-1BB (SEQIDs 21-32) and an anti-human CD3 binding domain (SEQIDs 1-8). These binding domains were converted to scFv, VLVH, for placement at the N-terminal Domain 1 (D1) or scFv, VHVL, for placement at the C-terminal Domains 3 (D3) and 4 (D4) of the peptide (FIG. 1).

In some embodiments, scFv molecules described herein contain a 20 amino acid flexible gly-gly-gly-gly-ser (G4S) X4 linker that operably links the VH and VL, regardless of the V-region orientation (LH or HL). The remaining position in the tetra-specific protein, Domain 2 (D2), consists of an IgG1 heavy chain, VH-CH1-Hinge-CH2-CH3, and its corresponding light chain, VL-CL, which may be either a kappa or lambda chain. D1 and D2 are genetically linked through a 10 amino acid (G4S)×2 linker, as are D2, D3 and D4 resulting in a contiguous ~150 kDa heavy chain monomer peptide. When co-transfected with the appropriate light chain, the final symmetric tetra-specific peptide may be purified through the IgG1 Fc (Protein A/Protein G) and assayed to assess functional activity. Heavy and light chain gene "cassettes" were previously constructed such that V-regions could be cloned using either restriction enzyme sites (Hindlll/Nhel for the heavy chain and Hindlll/BsiWl for the light chain) or "restriction-free cloning" such as GIBSON ASSEMBLY™ (SGI-DNA, La Jolla, Calif.), INFUSION™ (Takara Bio USA) or NEBUILDER® (NEB, Ipswich, Mass.), the latter of which was used here.

Tetra-specific proteins are produced through a process that involves design of the intact molecule, synthesis and cloning of the nucleotide sequences for each domain, expression in mammalian cells and purification of the final product. Nucleotide sequences were assembled using the GENEIOUS® 10.2.3 software package (Biomatters, Auckland, NZ) and broken up into their component domains for gene synthesis (GENEWIZ®, South Plainsfield, NJ).

In this example, S1-35E18 (SEQID 65 and 67) was split into its component domains where the anti-4-1BB scFv, VLVH, occupies D1, anti-human PD-L1 clone PL23006 occupies D2 (Fab position), anti-human ROR1 Ig domain-specific clone 323H7 VHVL scFv occupies D3, and anti-human CD3 scFv, VHVL, occupies the C-terminal D4. Using NEBUILDER® web-based tools, 5' and 3' nucleotides were appended to each of the domains depending on their position in the larger protein so that each domain overlaps its flanking domains by 20-30 nucleotides which direct site-specific recombination, thus genetically fusing each domain in a single gene assembly step. Due to the high number of homologous regions in the tetra-specific nucleotide sequence, the N-terminal domains 1 and 2 are assembled separately from the C-terminal D3 and D4. The N- and C-terminal fragments were then assembled together in a second NEBUILDER® reaction.

A small aliquot was transformed into *E. coli* DH10b (Invitrogen, Carlsbad, Calif.) and plated on TB+carbenicillin 100 ug/ml plates (Teknova, Hollister, CA) and incubated at 37C overnight. Resultant colonies were selected and 2 ml overnight cultures inoculated in TB+carbenicillin. DNA was prepared (Thermo-Fisher, Carlsbad, Calif.) from overnight cultures and subsequently sequenced (GENEWIZ®, South Plainsfield, NJ) using sequencing primers (Sigma, St. Louis, Mo.) flanking each domain. In some embodiments, DNA sequences were assembled and analyzed in GENEIOUS® software.

In another aspect, the application provides pharmaceutical compositions including the multi-specific antibody monomers, the multi-specific antibodies, the antigen-binding fragments, and the immuno-conjugates thereof, and methods of using the disclosed antibodies or pharmaceutical compositions for treatment of cancer.

The advantages of using the disclosed tetra-specific antibody monomers, multi-specific antibodies or compositions for treatment purpose over any existing therapies include, among others: 1) Inclusion of an IgG Fc domain may confer the characteristic of a longer half-life in serum compared to a bi-specific BiTe molecule; 2) Inclusion of two binding domains that are specific for immune checkpoint modulators, that may inhibit the suppressive pathways and engage the co-stimulatory pathways at the same time; and 3) Cross-link CD3 on T cells with tumor associated antigens thus "re-directing" T cells to kill the tumor without the need to remove T cells from the patient and genetically modify them to be specific for the tumor cell before re-introducing them back into the patient as done for chimeric antigen receptor T cells (CAR-T).

Formulation of the pharmaceutical composition may be accomplished according to standard methodology know to those of ordinary skill in the art.

In one embodiment, the antibodies and monomers according to the disclosure may be prepared in a physiologically acceptable formulation and may comprise a pharmaceutically acceptable carrier, diluent and/or excipient using known techniques. For example, the antibody according to the disclosure and as described herein including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Formulation of the pharmaceutical composition according to the disclosure may be accomplished according to standard methodology know to those of ordinary skill in the art.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Suitable pharmaceutical carriers, diluents and/or excipients are well known in the art and include, for example, phosphate buffered saline solutions, water, emulsions such as oil/water emulsions.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio.

In one embodiment, the pharmaceutical composition may include proteinaceous carriers such as, for example, serum albumin or immunoglobulin, particularly of human origin. Further biologically active agents may be present in the pharmaceutical composition of the disclosure dependent on the intended use. In one embodiment, the proteinaceous pharmaceutically active matter may be present in amounts between 1 ng and 10 mg per dose. Generally, the regime of administration should be in the range of between 0.1 µg and 10 mg of the antibody according to the disclosure, particularly in a range 1.0 µg to 1.0 mg, and more particularly in a range of between 1.0 µg and 100 µg, with all individual numbers falling within these ranges also being part of the disclosure. If the administration occurs through continuous infusion a more proper dosage may be in the range of between 0.01 µg and 10 mg units per kilogram of body weight per hour with all individual numbers falling within these ranges also being part of the disclosure.

The compositions of the present disclosure may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

It is well known to those of ordinary skill in the art that the dosage of the composition may depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The term "therapeutically effective amount" or "effective amount" refers to the amount of antibody which, when administered to a human or animal, elicits a response which is sufficient to result in a therapeutic effect in said human or animal, e.g., to ameliorate disease in a subject. The effective amount is readily determined by one of ordinary skill in the art following routine procedures. Where the disease is a cancer, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is a mayer, the effective amount of the drug may alternatively do one or more of the following when administered to a subject: slow or stop tumor growth, reduce tumor size (for example, volume or mass), relieve to some extent one or more of the symptoms associated with the cancer, extend progression free survival, result in an objective response (including, for example, a partial response or a complete response), and increase overall survival time. To the extent the drug may prevent growth and/or kill existing cancer cells, it is cytostatic and/or cytotoxic.

A person skilled in the art have the ability to determine the effective amount or concentration of the antibodies disclosed therein to effective treat a condition such as a cancer. Other parameters such as the proportions of the various components in the pharmaceutical composition, administration does and frequency may be obtained by a person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

The compositions may be administered by standard routes of administration. In general, the composition may be administered by topical, oral, rectal, nasal, intradermal, intraperitoneal, or parenteral (for example, intravenous, subcutaneous, or intramuscular) routes. In some embodiments, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

In one embodiment, the administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The antibody monomers, antibodies, antigen-binding fragments and immuno-conjugates thereof may be used in combination with a therapeutic agent or a composition comprising a therapeutic agent for treatment purpose.

In some embodiments, the multi-specific antibody molecule is used in combination with one or more additional therapeutic agents at an effective amount. The additional therapeutic agent includes an antibody, a chemotherapy agent, an enzyme, or a combination thereof. In some embodiment, the additional therapeutic agent may be an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In some embodiments, the additional therapeutic agent may be a check point inhibitor. In some embodiments, therapeutic agent comprises inhibitors of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In one embodiment, the therapeutic agent may include capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, a derivative or a combination thereof. In one embodiment, the therapeutic agent may include capecitabine, cisplatin, Cyclophosphamide, methotrexate, 5-fluorouracil, Doxorubicin, cyclophosphamide, mustine, vincristine, procarbazine, prednisolone, bleomycin, vinblastine, dacarbazine, etoposide, Epirubicin, pemetrexed, folinic acid, gemicitabine, oxaliplatin, irinotemay, topotemay, camptothecin, docetaxel, paclitaxel, fulvestrant, tamoxifen, letrozole, exemestane, anastrozole, aminoglutethimide, testolactone, vorozole, formestane, fadrozole, letrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, a derivative or a combination thereof.

Cancers, including breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer, may express cancer-associated genes. Inhibition of cancer-associated activity with specific monoclonal antibodies or antigen-binding fragment may have therapeutic effect on cancers. Furthermore, administering a therapeutically effective amount of composition comprising monoclonal antibodies or antigen-binding fragment specific for cancer-associated protein may cure, prevent, ameliorate, and delay the development or metastasis of cancers, through the effect of the cytotoxic agent.

The present disclosure may be understood more readily by reference to the following detailed description of specific embodiments and examples included herein. Although the present disclosure has been described with reference to specific details of certain embodiments thereof, it is not intended that such details should be regarded as limitations upon the scope of the disclosure.

EXAMPLES

Example 1: Binding of Tetra-Specific Antibodies to EGFRvlll Antigen

Binding of tetra-specific antibodies listed in TABLE 1 to EGFRvlll antigen expressed on the surface of U87 cell line was assessed using FACS method. The tetra-specific antibodies were incubated with U87 cell line and then detected with secondary anti-human antibodies directly conjugated to ALEXA FLUOR 647™ fluorochrome. Cellular binding of the tetra-specific antibodies was analyzed on a flow cytometer BD LSRFORTESSA™. All tested antibodies bound to the antigen with a KD in a single digit and sub-nanomolar range (TABLE 2). Observed differences in binding were within 3-fold range and might be driven by the position of the binding domain within the molecule as well as by interactions with adjacent domains.

TABLE 1 shows example tetra-specific antibodies with EGFRvlll tumor antigen binding domain. TABLE 2 shows the binding to EGFRvlll antigen expressed in U87 cell line. Binding of tetra-specific antibodies listed in TABLE 1 to EGFRvlll antigen was assessed by flow cytometry.

TABLE 1

Tetra-specific antibodies with EGFRvIII tumor antigen binding domain.

| Antibody ID | Antibody domain structure |
|---|---|
| SI-39E29 | 806 × 284A10 × PL221 × 420H5 |
| SI-39E18 | 284A10 × 806 × PL221 × 420H5 |
| SI-39E13 | 420H5 × PL230 × 284A10 × 806 |
| SI-39E4 | PL230 × 806 × 284A10 × 420H5 |
| SI-39E10 | 420H5 × PL230 × 806 × 284A10 |
| SI-39E23 | PL230 × 806 × 420H5 × 284A10 |

TABLE 2

Binding to EGFRvIII antigen expressed in CHO cell line.

| | CHO-EGFRviii binding | |
|---|---|---|
| Antibody ID | Antibody domain structure | EC50 (nM) |
| SI-39E29 | 806 × 284A10 × PL221 × 420H5 | 0.489 |
| SI-39E18 | 284A10 × 806 × PL221 × 420H5 | 0.7549 |
| SI-39E13 | 420H5 × PL230 × 284A10 × 806 | 1.244 |
| SI-39E4 | PL230 × 806 × 284A10 × 420H5 | 1.115 |
| SI-39E10 | 420H5 × PL230 × 806 × 284A10 | 1.542 |
| SI-39E23 | PL230 × 806 × 420H5 × 284A10 | 0.9222 |

Example 2: Binding of Tetra-Specific Antibodies to EGFRvlll, 4-1BB, PD-L1 and CD3 Protein Antigens Binding affinities and kinetics of tetra-specific antibodies listed in TABLE 1 to their respective antigens was assessed via Surface Plasmon Resonance on FORTEBIO® OCTET® RED96 instrument. The antigens were immobilized on the sensor chip surface and the tested antibodies were flown over the immobilized antigens. All molecules showed high binding to the antigens (TABLE 3). SI-39E29, SI-39E18 and SI-39E23 showed lower binding to CD3 e/d antigen than other antibodies tested. TABLE 3 shows the binding of tetra-specific antibodies listed in TABLE 1 to EGFRvlll, 4-1BB, PD-L1 and CD3 antigens.

TABLE 3. Binding to EGFRvlll, 4-1BB, PD-L1 and CD3 antigens.

TABLE 3A

| Antibody ID | Antibody domain structure | EGFRVIII binding | | | | 4-1BB binding | | | |
|---|---|---|---|---|---|---|---|---|---|
| | | Response | KD (M) | kon(1/Ms) | kdis(1/s) | Response | KD (M) | kon(1/Ms) | kdis(1/s) |
| SI-39E29 | 806 × 284A10 × PL221 × 420H5 | 1.4113 | <1.0E−12 | 1.38E+05 | <1.0E−07 | 1.9181 | 5.94E−10 | 2.32E+05 | 1.38E−04 |
| SI-39E18 | 284A10 × 806 × PL221 × 420H5 | 1.4606 | <1.0E−12 | 1.19E+05 | <1.0E−07 | 2.0165 | 3.93E−10 | 2.35E+05 | 9.24E−05 |
| SI-39E13 | 420H5 × PL230 × 284A10 × 806 | 1.2317 | <1.0E−12 | 9.90E+04 | <1.0E−07 | 2.4703 | 1.17E−10 | 2.27E+05 | 2.65E−05 |
| SI-39E4 | PL230 × 806 × 284A10 × 420H5 | 1.4058 | <1.0E−12 | 8.43E+04 | <1.0E−07 | 2.417 | 3.54E−10 | 1.67E+05 | 5.91E−05 |
| SI-39E10 | 420H5 × PL230 × 806 × 284A10 | 1.1414 | <1.0E−12 | 8.63E+04 | <1.0E−07 | 2.6348 | 3.56E−11 | 2.09E+05 | 7.43E−06 |
| SI-39E23 | PL230 × 806 × 420H5 × 284A10 | 1.3408 | <1.0E−12 | 1.41E+05 | <1.0E−07 | 2.0159 | 6.96E−10 | 2.03E+05 | 1.41E−04 |

TABLE 3B

| Antibody ID | Antibody domain structure | PD-L1 binding | | | | CD3 e/d binding | | | |
|---|---|---|---|---|---|---|---|---|---|
| | | Response | KD (M) | kon(1/Ms) | kdis(1/s) | Response | KD (M) | kon(1/Ms) | kdis(1/s) |
| SI-39E29 | 806 × 284A10 × PL221 × 420H5 | 1.7228 | 2.83E−10 | 3.76E+05 | 1.06E−04 | 1.8493 | 4.75E−10 | 1.66E+05 | 7.86E−05 |
| SI-39E18 | 284A10 × 806 × PL221 × 420H5 | 1.8256 | 1.68E−10 | 3.79E+05 | 6.37E−05 | 1.7586 | 6.32E−10 | 1.74E+05 | 1.10E−04 |
| SI-39E13 | 420H5 × PL230 × 284A10 × 806 | 1.9223 | 8.01E−11 | 4.15E+05 | 3.32E−05 | 1.8019 | <1.0E−12 | 1.04E+05 | <1.0E−07 |
| SI-39E4 | PL230 × 806 × 284A10 × 420H5 | 2.1532 | 7.23E−11 | 3.33E+05 | 2.41E−05 | 1.965 | <1.0E−12 | 8.61E+04 | <1.0E−07 |
| SI-39E10 | 420H5 × PL230 × 806 × 284A10 | 1.9364 | 6.85E−11 | 3.81E+05 | 2.61E−05 | 2.2404 | <1.0E−12 | 1.10E+05 | <1.0E−07 |
| SI-39E23 | PL230 × 806 × 420H5 × 284A10 | 1.9024 | 4.02E−11 | 4.83E+05 | 1.94E−05 | 2.6545 | 2.07E−10 | 1.23E+05 | 2.54E−05 |

Example 3: Redirected PBMC Cytotoxicity Against Astrocytoma Cell Line U87 that was Transfected with EGFRvlll Tetra-specific antibodies listed in TABLE 1 were assessed for their ability to redirect PBMC to lyse U87 transfected with EGFRvlll tumor cell line (U87vlll). PBMC were isolated by ficoll gradient. U87vlll tumor cell line was stably expressing nucleus-localized Red Fluorescent Protein (RFP) delivered via lentiviral transduction (Sartorius). U87vlll tumor cells were co-cultured with PBMC. Lysis of tumor cells was assessed by counting RFP labeled tumor cell nuclei. Images were acquired on live cell imager INCUCYTE® (Sartorius). S1-39E18 and S1-39E13 tetra-specific antibodies showed the highest efficacy at 96 hours followed by S1-39E10. S1-39E4, S1-39E23 and S1-39E29 showed lower efficacy in this study than other antibodies listed in TABLE 1 (FIG. 2).

Example 4: Redirected PBMC Cytotoxicity Against Acute Lymphoblastic Leukemia Cell Line Kasumi-2

Tetra-specific antibodies listed in TABLE 4 were assessed for their ability to lyse leukemia cell line Kasumi-2. PBMC were isolated by ficoll gradient. Kasumi-2 tumor cells were co-cultured with PBMC. Tumor cell lysis was assessed on BD LSRFORTESSA® flow cytometer via counting the number of live tumor cells present after 96 hours of co-culture. Tetra-specific antibody S1-38E14 showed the most potent activity in this study followed by S1-38E38 (FIG. 3). TABLE 4 shows example tetra-specific antibodies with CD19 tumor antigen recognition domain.

TABLE 4

Tetraspecific antibodies with CD19 tumor antigen recognition domain.

| Antibody ID | Antibody domain structure |
|---|---|
| SI-38E14 | PL230 × 466F6 × 21D4 × 284A10 |
| SI-38E38 | PD224 × 466F6 × 21D4 × 284A10 |
| SI-38E5 | 466F6 × PL230 × 284A10 × 21D4 |
| SI-38E20 | 466F6 × 21D4 × 284A10 × PL221 |
| SI-38E35 | 21D4 × 284A10 × 466F6 × PL221 |

Example 5: Redirected PBMC Cytotoxicity Against Astrocytoma Cell Line U87 that was Transfected with EGFRvlll, Functional Activity of Different 4-1BB Domains and Functional Impact of PD-L1 and 4-1BB Domains Tetra-specific antibodies listed in TABLE 5 were assessed for their ability to redirect PBMC to lyse U87 transfected with EGFRvlll tumor cell line (U87vlll). PBMC were isolated by ficoll gradient. U87vlll tumor cell line was stably expressing nucleus-localized Red Fluorescent Protein (RFP) delivered via lentiviral transduction (Sartorius). U87vlll tumor cells were co-cultured with PBMC. Lysis of tumor cells was assessed by counting RFP labeled tumor cell nuclei. Images were acquired on live cell imager INCUCYTE® (Sartorius). Activity of the antibodies was assessed after 96 hours of incubation. Antibodies with different 4-1BB domains—S1-39E4, S1-39E2 and S1-39E3 showed similar activity (FIG. 4). Antibodies with PD-L1 and 4-1BB domains replaced by silent (not functional) FITC domains, SI-39E1 and S1-39E5, showed reduction in lysis activity. This observation confirms functional contribution of 4-1BB and PD-L1 domains. TABLE 5 shows example tetra-specific antibodies with EGFRvlll tumor antigen binding domain. FITC control antibodies.

TABLE 5

Tetraspecific antibodies with EGFRvIII tumor antigen binding domain. FITC control antibodies.

| Antibody ID | Antibody domain structure |
|---|---|
| SI-39E4 | PL230 × 806 × 284A10 × 420H5 |
| SI-39E3 | PL230 × 806 × 284A10 × 466F6 |
| SI-39E2 | PL230 × 806 × 284A10 × 460C3 |
| SI-39E5 | FITC × 806 × 284A10 × 420H5 |
| SI-39E1 | PL230 × 806 × 284A10 × FITC |

Example 6: FACS Analysis of Tetra-Specific Specific Antibody Binding to Human ROR1 Transfected CHO Cells The tetra-specific-specific antibodies listed in TABLEs 1 and 2 were tested for binding to Chinese hamster ovary cells (CHO) cells stably expressing full length human ROR1. Antibodies were prepared at 2×final concentration and titrated 1:5 across 3 wells of a 96 well plate in 50 ul of PBS/2% FBS and then 5,000 ROR1-CHO cells in 50ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA® and the binding profile is shown in FIG. 5. The tetra-specific antibodies SI-35E18, 19, and 20, with the 323H7 binding domain specific for the Ig domain of ROR1, showed higher binding than the tetra-specific antibodies S1-3521, 22, and 23, with the 338H4 binding domain specific for the frizzled domain of ROR1, and the tetra-specific antibodies SI-3524, 25, and 26, with the 330F11 binding domain specific for the kringle domain of ROR1, did not bind.

Example 7: FACS Analysis of Tetra-Specific Specific Antibody Binding to Human 41BB Transfected CHO Cells The tetra-specific-specific antibodies listed in TABLE 6 were tested for binding to Chinese hamster ovary cells (CHO) cells stably expressing full length human ROR1. Antibodies were prepared at 2×final concentration and titrated 1:5 across 3 wells of a 96 well plate in 50 ul of PBS/2% FBS and then 5,000 ROR1-CHO cells in 50ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA® and the binding profile is shown in FIG. 6. All of the tetra-specific antibodies except for the control SI-27E12 contain a 41BB binding domain, 460C3, 420H5, or 466F6 and bound to 41BB expressing CHO cells with varying intensity. TABLE 6 shows the example tetra-specific antibody list.

TABLE 6

Tetraspecific antibody list.

| | | Domain 1 | | Domain 2 | | | Domain 3 | | Domain 4 | |
|---|---|---|---|---|---|---|---|---|---|---|
| ID = | SI-xx | LH-scFv | Humanized Variant | Fab | Humanized Variant | Fc | HL-scFv | Humanized Variant | HL-scFv | Humanized Variant |
| 39 | E02 | PL230C6 | L2H3 | 806 | — | | 284A10 | H1L1 | 460C3 | H1L1 |
| 39 | E03 | PL230C6 | L2H3 | 806 | — | | 284A10 | H1L1 | 466F6 | H2L5 |
| 39 | E18 | 284A10 | L1H1 | 806 | — | n2 | PL221G5 | H1L1 | 420H5 | H3L3 |
| 39 | E13 | 420H5 | L3H3 | PL230C6 | H3L2 | n2 | 284A10 | H1L1 | 806 | |
| 39 | E10 | 420H5 | L3H3 | PL230C6 | H3L2 | n2 | 806 | — | 284A10 | H1L1 |
| 39 | E29 | 806 | — | 284A10 | H1L1 | n2 | PL221G5 | H1L1 | 420H5 | H3L3 |
| 39 | E04 | PL230C6 | L2H3 | 806 | — | n2 | 284A10 | H1L1 | 420H5 | H3L3 |
| 39 | E23 | PL230C6 | L2H3 | 806 | — | n2 | 420H5 | H3L3 | 284A10 | H1L1 |
| 38 | E14 | PL230C6 | L2H3 | 466F6 | H2L5 | n2 | 21D4 | — | 284A10 | H1L1 |
| 38 | E38 | PD224D1 | L2H2 | 466F6 | H2L5 | n2 | 21D4 | — | 284A10 | H1L1 |
| 38 | E05 | 466F6 | L5H2 | PL230C6 | H3L2 | n2 | 284A10 | H1L1 | 21D4 | — |
| 38 | E20 | 466F6 | L5H2 | 21D4 | — | n2 | 284A10 | H1L1 | PL221G5 | H1L1 |
| 39 | E05 | 4-4-20 (FITC) | — | 806 | — | n2 | 284A10 | H1L1 | 420H5 | H3L3 |
| 39 | E01 | PL230C6 | L2H3 | 806 | — | n2 | 284A10 | H1L1 | 4-4-20 (FITC) | — |
| 35 | E02 | 460C3 | L1H1 | PL230C6 | H3L2 | n2 | 324C6 | H2L1 | 4-4-20 (FITC) | — |
| 35 | E12 | 4-4-20 (FITC) | — | PL230C6 | H3L2 | n2 | 324C6 | H2L1 | 480C8 | H1L1 |
| 35 | E13 | 460C3 | L1H1 | PL230C6 | H3L2 | n2 | 4-4-20 (FITC) | — | 480C8 | H1L1 |
| 35 | E15 | 460C3 | L1H1 | 4-4-20 (FITC) | — | n2 | 324C6 | H2L1 | 480C8 | H1L1 |
| 35 | E18 | 460C3 | L1H1 | PL230C6 | H3L2 | n2 | 323H7 | H4L1 | 284A10 | H1L1 |
| 35 | E19 | 420H5 | L3H3 | PL230C6 | H3L2 | n2 | 323H7 | H4L1 | 284A10 | H1L1 |
| 35 | E20 | 466F6 | L5H2 | PL230C6 | H3L2 | n2 | 323H7 | H4L1 | 284A10 | H1L1 |
| 35 | E21 | 460C3 | L1H1 | PL230C6 | H3L2 | n2 | 338H4 | H3L4 | 284A10 | H1L1 |
| 35 | E22 | 420H5 | L3H3 | PL230C6 | H3L2 | n2 | 338H4 | H3L4 | 284A10 | H1L1 |
| 35 | E23 | 466F6 | L5H2 | PL230C6 | H3L2 | n2 | 338H4 | H3L4 | 284A10 | H1L1 |
| 35 | E24 | 460C3 | L1H1 | PL230C6 | H3L2 | n2 | 330F11 | H1L1 | 284A10 | H1L1 |
| 35 | E25 | 420H5 | L3H3 | PL230C6 | H3L2 | n2 | 330F11 | H1L1 | 284A10 | H1L1 |
| 35 | E26 | 466F6 | L5H2 | PL230C6 | H3L2 | n2 | 330F11 | H1L1 | 284A10 | H1L1 |

TABLE 6-continued

Tetraspecific antibody list.

| ID = | SI-xx | Domain 1 LH-scFv | Humanized Variant | Domain 2 Fab | Humanized Variant | Domain 3 Fc | HL-scFv | Humanized Variant | Domain 4 HL-scFv | Humanized Variant |
|---|---|---|---|---|---|---|---|---|---|---|
| 35 | E36 | 4-4-20 (FITC) | — | PL230C6 | H3L2 | n2 | 338H4 | H3L4 | 284A10 | H1L1 |
| 35 | E37 | 460C3 | L1H1 | 4-4-20 (FITC) | — | n2 | 338H4 | H3L4 | 284A10 | H1L1 |
| 35 | E38 | 460C3 | L1H1 | PL230C6 | H3L2 | n2 | 4-4-20 (FITC) | — | 284A10 | H1L1 |
| 35 | E39 | 460C3 | L1H1 | PL230C6 | H3L2 | n2 | 338H4 | H3L4 | 4-4-20 (FITC) | — |

Example 8: FACS Analysis of Tetra-Specific Specific Antibody Binding to Human PD-11. Transfected CHO Cells The tetra-specific-specific antibodies listed in TABLE 6 were tested for binding to Chinese hamster ovary cells (CHO) cells stably expressing full length human ROR1. Antibodies were prepared at 2×final concentration and titrated 1:5 across 3 wells of a 96 well plate in 50 ul of PBS/2% FBS and then 5,000 ROR1-CHO cells in 50ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA® and the binding profile is shown in FIG. 7. All of the tetra-specific antibodies except for the control SI-27E15 contain the same PD-L1 binding domain, PL23006, and showed very similar binding intensity to PD-L1 expressing CHO cells.

Example 9: Re-Directed T Cell Cytotoxicity (RTCC) Assay with Peripheral Blood Mononuclear Cells as Effectors and B-Acute Lymphoblastic Leukemia (B-ALL) Cell Line Kasumi-2 as Targets The tetra-specific-specific antibodies listed in TABLE 6 were tested for RTCC activity against the B-ALL cell line Kasumi 2 using human peripheral blood mononuclear cells (PBMC) as effectors. The Kasumi 2 target cells, 5×10e6, were labeled with CFSE (Invitrogen, #C34554) at 0.5 uM in 10 ml of culture media for 20 minutes at 37C. The cells were washed 3 times with 50 ml of culture media before resuspending in 10 ml then counted again. Antibodies were prepared at 2×final concentration and titrated 1:3 across 10 wells of a 96 well plate in 200 ul of RPMI+10% FBS. Human PBMC were purified by standard ficoll density gradient from a "leukopak" which is an enriched leukapheresis product collected from normal human peripheral blood. In the final destination 96 well plate the target cells, PBMC, and serially titrated antibodies were combined by adding 100 ul of target cells (5,000), 50 ul of PBMC (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 8, the tetra-specific antibodies all contain the same PD-L1 binding domain PL23006, the same ROR1 binding domain 323H7, and the same CD3 binding domain 284A10, but have one of the 41BB binding domains 460C3, 420H5, and 466F6 and showed greater RTCC activity compared to the controls except for the control SI-27E12 which does not have a 41BB binding domain but appeared to be similarly potent at the tetra-specific antibodies SI-35E18, 19, and 20.

Example 10: Re-Directed T Cell Cytotoxicity (RTCC) Assay with CD8+, CD45RO+ Memory T Cells as Effectors and B-Acute Lymphoblastic Leukemia (B-ALL) Cell Line Kasumi-2 as Targets The tetra-specific-specific antibodies listed in TABLE 6 were tested for RTCC activity against the B-ALL cell line Kasumi 2 using human CD8+, CD45RO+ memory T cells as effectors. The Kasumi 2 target cells, 5×10e6, were labeled with CFSE (Invitrogen, #C34554) at 0.5 uM in 10 ml of culture media for 20 minutes at 37C. The cells were washed 3 times with 50 ml of culture media before resuspending in 10 ml then counted again. Antibodies were prepared at 2×final concentration and titrated 1:3 across 10 wells of a 96 well plate in 200 ul of RPMI+10% F6S. Human CD8+, CD45RO+ memory T cells were enriched from peripheral blood mononuclear cells from a normal donor using the EASYSEP™ Human Memory CD8+ T Cell Enrichment Kit (Stemcell Technologies, #19159) as per the manufacturers protocol. The final cell population was determined to be 98% CD8+, CD45RO+ T cells by FACS analysis (data not shown). In the final destination 96 well plate the target cells, T cells, and serially titrated antibodies were combined by adding 100 ul of target cells (5,000), 50 ul of CD8+, CD45RO+ memory T cells (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 9, the tetra-specific antibodies all contain the same PD-L1 binding domain PL23006, the same ROR1 binding domain 323H7, and the same CD3 binding domain 284A10, but have one of the 41BB binding domains 460C3, 420H5, and 466F6 and showed greater RTCC activity compared to the controls that do not contain one of the 41BB, PD-L1, ROR1, or CD3 binding domains.

Example 11: Re-Directed T Cell Cytotoxicity (RTCC) Assay with CD8+, CD45RA+ Naive T Cells as Effectors and B-Acute Lymphoblastic Leukemia (B-ALL) Cell Line Kasumi-2 as Targets The tetra-specific-specific antibodies listed in TABLE 6 were tested for RTCC activity against the B-ALL cell line Kasumi 2 using human CD8+, CD45RA+ memory T cells as effectors. The Kasumi 2 target cells, 5×10e6, were labeled with CFSE (Invitrogen, #C34554) at 0.5 uM in 10 ml of culture media for 20 minutes at 37C. The cells were washed 3 times with 50 ml of culture media before resuspending in 10 ml then counted again. Antibodies were prepared at 2×final concentration and titrated 1:3 across 10 wells of a 96 well plate in 200 ul of RPMI+10% FBS. Human CD8+, CD45RA+ memory T cells were enriched from peripheral blood mononuclear cells from a normal donor using the EASYSEP™ Human Naive CD8+ T Cell Isolation Kit (Stemcell Technologies, #19258) as per the manufacturers protocol. The final cell population was determined to be 98% CD8+, CD45RA+ T cells by FACS analysis (data not shown). In the final destination 96 well plate the target cells, T cells, and serially titrated antibodies were combined by adding 100 ul of target cells (5,000), 50 ul of CD8+, CD45RO+ T cells (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 10, the tetra-specific antibodies all contain the same PD-L1 binding domain PL23006, the same ROR1 binding domain 323H7, and the same CD3 binding domain 284A10, but have one of the 41BB binding domains 460C3, 420H5, and 466F6 and showed greater RTCC activity compared to the controls that do not contain one of the 41BB, PD-L1, ROR1, or CD3 binding domains.

Example 12: Re-Directed T Cell Cytotoxicity
(RTCC) Assay with Peripheral Blood Mononuclear
Cells as Effectors and B-Acute Lymphoblastic
Leukemia (B-ALL) Cell Line Kasumi-2 as Targets The tetra-specific-specific antibodies listed in TABLE 6 were tested for RTCC activity against the B-ALL cell line Kasumi 2 using human peripheral blood mononuclear cells (PBMC) as effectors. The Kasumi 2 target cells, 5×10e6, were labeled with CFSE (Invitrogen, #C34554) at 0.5 uM in 10 ml of culture media for 20 minutes at 37C. The cells were washed 3 times with 50 ml of culture media before resuspending in 10 ml then counted again. Antibodies were prepared at 2×final concentration and titrated 1:3 across 10 wells of a 96 well plate in 200 ul of RPMI+10% FBS. Human PBMC were purified by standard ficoll density gradient from a "leukopak" which is an enriched leukapheresis product collected from normal human peripheral blood. In the final destination 96 well plate the target cells, PBMC, and serially titrated antibodies were combined by adding 100 ul of target cells (5,000), 50 ul of PBMC (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 11, the tetra-specific antibodies all contain the same PD-L1 binding domain PL23006, the same ROR1 binding domain 338H4, and the same CD3 binding domain 284A10, but have one of the 41BB binding domains 460C3, 420H5, and 466F6 and showed greater RTCC activity compared to the controls except for the control SI-35E36 which does not have a 41BB binding domain but appeared to be similarly potent at the tetra-specific antibodies SI-35E18, 19, and 20.

Example 13: Re-Directed T Cell Cytotoxicity
(RTCC) Assay with CD8+, CD45RO+ Memory T
Cells as Effectors and B-Acute Lymphoblastic
Leukemia (B-ALL) Cell Line Kasumi-2 as Targets The tetra-specific-specific antibodies listed in TABLE 6 were tested for RTCC activity against the B-ALL cell line Kasumi 2 using human CD8+, CD45RO+ memory T cells as effectors. The Kasumi 2 target cells, 5×10e6, were labeled with CFSE (Invitrogen, #C34554) at 0.5 uM in 10 ml of culture media for 20 minutes at 37C. The cells were washed 3 times with 50 ml of culture media before resuspending in 10 ml then counted again. Antibodies were prepared at 2×final concentration and titrated 1:3 across 10 wells of a 96 well plate in 200 ul of RPMI+10% FBS. Human CD8+, CD45RO+ memory T cells were enriched from peripheral blood mononuclear cells from a normal donor using the EASYSEP™ Human Memory CD8+ T Cell Enrichment Kit (Stemcell Technologies, #19159) as per the manufacturers protocol. The final cell population was determined to be 98% CD8+, CD45RO+ T cells by FACS analysis (data not shown). In the final destination 96 well plate the target cells, T cells, and serially titrated antibodies were combined by adding 100 ul of target cells (5,000), 50 ul of CD8+, CD45RO+ memory T cells (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 12, the tetra-specific antibodies all contain the same PD-L1 binding domain PL23006, the same ROR1 binding domain 338H4, and the same CD3 binding domain 284A10, but have one of the 41BB binding domains 460C3, 420H5, and 466F6 and showed greater RTCC activity compared to the controls that do not contain one of the 41BB, PD-L1, ROR1, or CD3 binding domains.

Example 14: Re-Directed T Cell Cytotoxicity
(RTCC) Assay with CD8+, CD45RA+ Naive T
Cells as Effectors and B-Acute Lymphoblastic
Leukemia (B-ALL) Cell Line Kasumi-2 as Targets The tetra-specific-specific antibodies listed in TABLE 6 were tested for RTCC activity against the B-ALL cell line Kasumi 2 using human CD8+, CD45RA+ memory T cells as effectors. The Kasumi 2 target cells, 5×10e6, were labeled with CFSE (Invitrogen, #C34554) at 0.5 uM in 10 ml of culture media for 20 minutes at 37C. The cells were washed 3 times with 50 ml of culture media before resuspending in 10 ml then counted again. Antibodies were prepared at 2×final concentration and titrated 1:3 across 10 wells of a 96 well plate in 200 ul of RPMI+10% FBS. Human CD8+, CD45RA+ memory T cells were enriched from peripheral blood mononuclear cells from a normal donor using the EASYSEP™ Human Naive CD8+ T Cell Isolation Kit (Stemcell Technologies, #19258) as per the manufacturers protocol. The final cell population was determined to be 98% CD8+, CD45RA+ T cells by FACS analysis (data not shown). In the final destination 96 well plate the target cells, T cells, and serially titrated antibodies were combined by adding 100 ul of target cells (5,000), 50 ul of CD8+, CD45RO+ T cells (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 13, the tetra-specific antibodies all contain the same PD-L1 binding domain PL23006, the same ROR1 binding domain 338H4, and the same CD3 binding domain 284A10, but have one of the 41BB binding domains 460C3, 420H5, and 466F6 but did not show greater RTCC activity compared to the controls that do not contain one of the 41BB, PD-L1, ROR1, or CD3 binding domains. This is in contrast to the tetra-specific antibodies described in example 6 and shown in FIG. 10 that do show RTCC activity with CD8+, CD45RA+ naive T cells.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description. All references cited or referred to in this disclosure are hereby incorporated by reference in their entireties.

Multi-Specific Antibodies and Methods of Making and Using Thereof

```
                        SEQUENCE LISTING

CDR's underlined in amino acid sequences
>SEQ ID: 01 anti-CD3 284A10 VHv1 nt
GAGGTGCAGCTGGTGGAGTCTGGGGGAGGCTTGGTCCAGCCTGGGGGGTCCCTGAGACTCTCCTGTGCAGCCTC
TGGATTCACCATCAGTACCAATGCAATGAGCTGGGTCCGCCAGGCTCCAGGGAAGGGGCTGGAGTGGATCGGAG
TCATTACTGGTCGTGATATCACATACTACGCGAGCTGGGCGAAAGGCAGATTCACCATCTCCAGAGACAATTCC
AAGAACACGCTGTATCTTCAAATGAACAGCCTGAGAGCCGAGGACACGGCTGTGTATTACTGTGCGCGCGACGG
TGGATCATCTGCTATTACTAGTAACAACATTTGGGGCCAAGGAACTCTGGTCACCGTTTCTTCA >SEQ ID: 02 anti-CD3 284A10 VHv1 aa
EVQLVESGGGLVQPGGSLRLSCAASGFTISTNAMSWVRQAPGKGLEWIGVITGRDITYYASWAKGRFTISRDNS
KNTLYLQMNSLRAEDTAVYYCARDGGSSAITSNNIWGQGTLVTVSS >SEQ ID: 03 anti-CD3 284A10 VLv1 nt
GACGTCGTGATGACCCAGTCTCCTTCCACCCTGTCTGCATCTGTAGGAGACAGAGTCACCATCAATTGCCAAGC
CAGTGAGAGCATTAGCAGTTGGTTAGCCTGGTATCAGCAGAAACCAGGGAAAGCCCCTAAGCTCCTGATCTATG
AAGCATCCAAACTGGCATCTGGGGTCCCATCAAGGTTCAGCGGCAGTGGATCTGGGACAGAGTTCACTCTCACC
ATCAGCAGCCTGCAGCCTGATGATTTTGCAACTTATTACTGCCAAGGCTATTTTTATTTTATTAGTCGTACTTA
TGTAAATTCTTTCGGCGGAGGGACCAAGGTGGAGATCAAA >SEQ ID: 04 anti-CD3 284A10 VLv1 aa
DVVMTQSPSTLSASVGDRVTINCQASESISSWLAWYQQKPGKAPKLLIYEASKLASGVPSRFSGSGSGTEFTLT
ISSLQPDDFATYYCQGYFYFISRTYVNSFGGGTKVEIK >SEQ ID: 05 anti-CD3 480C8 VHv1 nt
GAGGTGCAGCTGGTGGAGTCTGGGGGAGGCTTGGTCCAGCCTGGGGGGTCCCTGAGACTCTCCTGTGCAGCCTC
TGGAATCGACCTCAGTAGCAATGCAATGAGCTGGGTCCGCCAGGCTCCAGGGAAGGGGCTGGAGTGGATCGGAG
TCATTACTGGTCGTGATATCACATACTACGCGAGCTGGGCGAAAGGCAGATTCACCATCTCCAGAGACAATTCC
AAGAACACGCTGTATCTTCAAATGAACAGCCTGAGAGCCGAGGACACGGCTGTGTATTACTGTGCGCGCGACGG
TGGATCATCTGCTATTAATAGTAAGAACATTTGGGGCCAAGGAACTCTGGTCACCGTTTCTTCA >SEQ ID: 06 anti-CD3 480C8 VHv1 aa
EVQLVESGGGLVQPGGSLRLSCAASGIDLSSNAMSWVRQAPGKGLEWIGVITGRDITYYASWAKGRFTISRDNS
KNTLYLQMNSLRAEDTAVYYCARDGGSSAINSKNIWGQGTLVTVSS >SEQ ID: 07 anti-CD3 480C8 VLv1 nt
GACATCCAGATGACCCAGTCTCCTTCCACCCTGTCTGCATCTGTAGGAGACAGAGTCACCATCACTTGCCAAGC
CAGTGAGAGCATTAGCAGTTGGTTAGCCTGGTATCAGCAGAAACCAGGGAAAGCCCCTAAGCTCCTGATCTATG
AAGCATCCAAACTGGCATCTGGGGTCCCATCAAGGTTCAGCGGCAGTGGATCTGGGACAGAGTTCACTCTCACC
ATCAGCAGCCTGCAGCCTGATGATTTTGCAACTTATTACTGCCAAGGCTATTTTTATTTTATTAGTCGTACTTA
TGTAAATGCTTTCGGCGGAGGGACCAAGGTGGAGATCAAA >SEQ ID: 08 anti-CD3 480C8 VLv1 aa
DIQMTQSPSTLSASVGDRVTITCQASESISSWLAWYQQKPGKAPKLLIYEASKLASGVPSRFSGSGSGTEFTLT
ISSLQPDDFATYYCQGYFYFISRTYVNAFGGGTKVEIK >SEQ ID: 09 anti-PD-L1 P1230C6 VHv3 nt
CAGTCGGTGGAGGAGTCTGGGGGAGGCTTGGTCCAGCCTGGGGGGTCCCTGAGACTCTCCTGTACAGCCTCTGG
AATCGACCTTAATACCTACGACATGATCTGGGTCCGCCAGGCTCCAGGCAAGGGGCTAGAGTGGGTTGGAATCA
TTACTTATAGTGGTAGTAGATACTACGCGAACTGGGCGAAAGGCCGATTCACCATCTCCAAAGACAATACCAAG
AACACGGTGTATCTGCAAATGAACAGCCTGAGAGCTGAGGACACGGCTGTGTATTACTGTGCCAGAGATTATAT
GAGTGGTTCCCACTTGTGGGGCCAGGGAACCCTGGTCACCGTCTCTAGT >SEQ ID: 10 anti-PD-L1 PL230C6 VHv3 aa
QSVEESGGGLVQPGGSLRLSCTASGIDLNTYDMIWVRQAPGKGLEWVGIITYSGSRYYANWAKGRFTISKDNTK
NTVYLQMNSLRAEDTAVYYCARDYMSGSHLWGQGTLVTVSS >SEQ ID: 11 anti-PD-L1 PL230C6 VLv2 nt
GCCTATGATATGACCCAGTCTCCATCTTCCGTGTCTGCATCTGTAGGAGACAGAGTCACCATCAAGTGTCAGGC
CAGTGAGGACATTTATAGCTTCTTGGCCTGGTATCAGCAGAAACCAGGGAAAGCCCCTAAGCTCCTGATCCATT
CTGCATCCTCTCTGGCATCTGGGGTCCCATCAAGGTTCAGCGGCAGTGGATCTGGGACAGATTTCACTCTCACC
ATCAGCAGCCTGCAGCCTGAAGATTTTGCAACTTACTATTGTCAACAGGGTTATGGTAAAAATAATGTTGATAA
TGCTTTCGGCGGAGGGACCAAGGTGGAGATCAAA
```

SEQUENCE LISTING

>SEQ ID: 12 anti-PD-L1 PL230C6 VLv2 aa
AYDMTQSPSSVSASVGDRVTIKCQASEDIYSFLAWYQQKPGKAPKLLIHSASSLASGVPSRFSGSGSGTDFTLT
ISSLQPEDFATYYCQQGYGKNNVDNAFGGGTKVEIK >SEQ ID: 13 anti-PD-L1 PL221G5 VHv1 nt
GAGGTGCAGCTGTTGGAGTCTGGGGGAGGCTTGGTACAGCCTGGGGGGTCCCTGAGACTCTCCTGTGCAGCCTC
TGGATTCTCCTTCAGTAGCGGGTACGACATGTGCTGGGTCCGCCAGGCTCCAGGGAAGGGGCTGGAGTGGATCG
CATGCATTGCTGCTGGTAGTGCTGGTATCACTTACGACGCGAACTGGGCGAAAGGCCGGTTCACCATCTCCAGA
GACAATTCCAAGAACACGCTGTATCTGCAAATGAACAGCCTGAGAGCCGAGGACACGGCCGTATATTACTGTGC
GAGATCGGCGTTTTCGTTCGACTACGCCATGGACCTCTGGGGCCAGGGAACCCTGGTCACCGTCTCGAGC >SEQ ID: 14 anti-PD-L1 PL221G5 VHv1 aa
EVQLLESGGGLVQPGGSLRLSCAASGFSFSSGYDMCWVRQAPGKGLEWIACIAAGSAGITYDANWAKGRFTISR
DNSKNTLYLQMNSLRAEDTAVYYCARSAFSFDYAMDLWGQGTLVTVSS >SEQ ID: 15 anti-PD-L1 PL221G5 VLv1 nt
GACATCCAGATGACCCAGTCTCCTTCCACCCTGTCTGCATCTGTAGGAGACAGAGTCACCATCACTTGCCAGGC
CAGTCAGAGCATTAGTTCCCACTTAAACTGGTATCAGCAGAAACCAGGGAAAGCCCCTAAGCTCCTGATCTATA
AGGCATCCACTCTGGCATCTGGGGTCCCATCAAGGTTCAGCGGCAGTGGATCTGGGACAGAATTTACTCTCACC
ATCAGCAGCCTGCAGCCTGATGATTTTGCAACTTATTACTGCCAACAGGGTTATAGTTGGGGTAATGTTGATAA
TGTTTTCGGCGGAGGGACCAAGGTGGAGATCAAA >SEQ ID: 16 anti-PD-L1 PL221G5 VLv1 aa
DIQMTQSPSTLSASVGDRVTITCQASQSISSHLNWYQQKPGKAPKLLIYKASTLASGVPSRFSGSGSGTEFTLT
ISSLQPDDFATYYCQQGYSWGNVDNVFGGGTKVEIK >SEQ ID: 17 anti-PD-1 PD224D1 VHv2 nt
GAGGTGCAGCTGGTGGAGTCTGGGGGAGGCTTGGTCCAGCCTGGGGGGTCCCTGAGACTCTCCTGTACAGCCTC
TGGATTCTCCCTAAGTAGCTATGCAATGAGCTGGGTCCGCCAGGCTCCAGGGAAGGGGCTGGAGTACATCGGCT
ACATTGGTGATACTACTGGCATAGCCTACGCGAGCTGGGCGAATGGCAGATTCACCATCTCCAAAGACAATACC
AAGAACACGGTGGATCTTCAAATGAACAGCCTGAGAGCCGAGGACACGGCTGTGTATTACTGTGCGAGAGGCTG
GTCCTACTTAGACATCTGGGGCCAAGGGACCCTGGTCACCGTCTCGAGC >SEQ ID: 18 anti-PD-1 PD224D1 VHv2 aa
EVQLVESGGGLVQPGGSLRLSCTASGFSLSSYAMSWVRQAPGKGLEYIGYIGDTTGIAYASWANGRFTISKDNT
KNTVDLQMNSLRAEDTAVYYCARGWSYLDIWGQGTLVTVSS >SEQ ID: 19 anti-PD-1 PD224D1 VLv2 nt
GCCCTTGTGATGACCCAGTCTCCATCCTCCCTGTCTGCATCTGTAGGAGACAGAGTCACCATCACTTGCCAGGC
CAGTCAGAACATTTACAGCAATTTAGCCTGGTATCAGCAGAAACCAGGGAAAGTTCCTAAGCTCCTGATCTATC
AGGCCTCCACTCTGGCATCTGGGGTCCCATCTCGGTTCAGTGGCAGTGGATATGGGACAGATTTCACTCTCACC
ATCAGCAGCCTGCAGCCTGAAGATGTTGCAACTTATTACTGTCAAGGCGGTTATTATAGTGCTGCCCTTAATAC
TTTCGGCGGAGGGACCAAGGTGGAGATCAAA >SEQ ID: 20 anti-PD-1 PD224D1 VLv2 aa
ALVMTQSPSSLSASVGDRVTITCQASQNIYSNLAWYQQKPGKVPKLLIYQASTLASGVPSRFSGSGYGTDFTLT
ISSLQPEDVATYYCQGGYYSAALNTFGGGTKVEIK >SEQ ID: 21 anti-4-1BB 420H5 VHv3 nt
CAGTCGCTGGTGGAGTCTGGGGGAGGCTTGGTACAGCCTGGGGGGTCCCTGAGACTCTCCTGTGCAGCCTCTGG
ATTCTCCTTCAGTAGCAACTACTGGATATGCTGGGTCCGCCAGGCTCCAGGGAAGGGGCTGGAGTGGATCGCAT
GCATTTATGTTGGTAGTAGTGGTGACACTTACTACGCGAGCTGGTCGGCGAAAGGCCGGTTCACCATCTCCAGAGAC
AATTCCAAGAACACGCTGTATCTGCAAATGAACAGCCTGAGAGCCGAGGACACGGCCGTATATTACTGTGCGAG
AGATAGTAGTAGTTATTATATGTTTAACTTGTGGGGCCAGGGAACCCTGGTCACCGTCTCGAGC >SEQ ID: 22 anti-4-1BB 420H5 VHv3 aa
QSLVESGGGLVQPGGSLRLSCAASGFSFSSNYWICWVRQAPGKGLEWIACIYVGSSGDTYYASSAKGRFTISRD
NSKNTLYLQMNSLRAEDTAVYYCARDSSSYYMFNLWGQGTLVTVSS >SEQ ID: 23 anti-4-1BB 420H5 VLv3 nt
GCCCTTGTGATGACCCAGTCTCCTTCCACCCTGTCTGCATCTGTAGGAGACAGAGTCACCATCAATTGCCAGGC
CAGTGAGGACATTGATACCTATTTAGCCTGGTATCAGCAGAAACCAGGGAAAGCCCCTAAGCTCCTGATCTTTT
ATGCATCCGATCTGGCATCTGGGGTCCCATCAAGGTTCAGCGGCAGTGGATCTGGGACAGAATTCACTCTCACC
ATCAGCAGCCTGCAGCCTGATGATTTTGCAACTTATTACTGCCAAGGCGGTTACTATACTAGTAGTGCTGATAC
GAGGGGTGCTTTCGGCGGAGGGACCAAGGTGGAGATCAAA >SEQ ID: 24 anti-4-1BB 420H5 VLv3 aa
ALVMTQSPSTLSASVGDRVTINCQASEDIDTYLAWYQQKPGKAPKLLIFYASDLASGVPSRFSGSGSGTEFTLT
ISSLQPDDFATYYCQGGYYTSSADTRGAFGGGTKVEIK >SEQ ID: 25 anti-4-1BB 466F6 VHv2 nt
CGGTCGCTGGTGGAGTCTGGGGGAGGCTTGGTCCAGCCTGGGGGGTCCCTGAGACTCTCCTGTACAGCCTCTGG
ATTCACCATCAGTAGCTACCACATGCAGTGGGTCCGCCAGGCTCCAGGGAAGGGGCTGGAGTACATCGGAACCA
TTAGTAGTGGTGGTAATGTATACTACGCGAGCTCCGCGAGAGGCAGATTCACCATCTCCAGACCCTCGTCCAAG
AACACGGTGGATCTTCAAATGAACAGCCTGAGAGCCGAGGACACGGCTGTGTATTACTGTGCGAGAGACTCTGG
TTATAGTGATCCTATGTGGGGCCAGGGAACCCTGGTCACCGTCTCGAGC

SEQUENCE LISTING

>SEQ ID: 26 anti-4-1BB 466F6 VHv2 aa
RSLVESGGGLVQPGGSLRLSCTASGFTISSYHMQWVRQAPGKGLEYIGTISSGGNVYYASSARGRFTISRPSSK
NTVDLQMNSLRAEDTAVYYCARDSGYSDPMWGQGTLVTVSS >SEQ ID: 27 anti-4-1BB 466F6 VLv5 nt
GACGTTGTGATGACCCAGTCTCCATCTTCCGTGTCTGCATCTGTAGGAGACAGAGTCACCATCACCTGTCAGGC
CAGTCAGAACATTAGGACTTACTTATCCTGGTATCAGCAGAAACCAGGGAAAGCCCCTAAGCTCCTGATCTATG
CTGCAGCCAATCTGGCATCTGGGGTCCCATCAAGGTTCAGCGGCAGTGGATCTGGGACAGATTTCACTCTCACC
ATCAGCGACCTGGAGCCTGGCGATGCTGCAACTTACTATTGTCAGTCTACCTATCTTGGTACTGATTATGTTGG
CGGTGCTTTCGGCGGAGGGACCAAGGTGGAGATCAAA >SEQ ID: 28 anti-4-1BB 466F6 VLv5 aa
DVVMTQSPSSVSASVGDRVTITCQASQNIRTYLSWYQQKPGKAPKLLIYAAANLASGVPSRFSGSGSGTDFTLT
ISDLEPGDAATYYCQSTYLGTDYVGGAFGGGTKVEIK >SEQ ID: 29 anti-4-1BB 460C3 VHv1 nt
GAGGTGCAGCTGTTGGAGTCTGGGGGAGGCTTGGTACAGCCTGGGGGGTCCCTGAGACTCTCCTGTGCAGCCTC
TGGAATCGACTTCAGTAGGAGATACTACATGTGCTGGGTCCGCCAGGCTCCAGGGAAGGGGCTGGAGTGGATCG
CATGCATATATACTGGTAGCCGCGATACTCCTCACTACGCGAGCTCCGCGAAAGGCCGGTTCACCATCTCCAGA
GACAATTCCAAGAACACGCTGTATCTGCAAATGAACAGCCTGAGAGCCGAGGACACGGCCGTATATTACTGTGC
GAGAGAAGGTAGCCTGTGGGGCCAGGGAACCCTGGTCACCGTCTCGAGC >SEQ ID: 30 anti-4-1BB 460C3 VHv1 aa
EVQLLESGGGLVQPGGSLRLSCAASGIDFSRRYYMCWVRQAPGKGLEWIACIYTGSRDTPHYASSAKGRFTISR
DNSKNTLYLQMNSLRAEDTAVYYCAREGSLWGQGTLVTVSS >SEQ ID: 31 anti-4-1BB 460C3 VLv1 nt
GACATCCAGATGACCCAGTCTCCTTCCACCCTGTCTGCATCTGTAGGAGACAGAGTCACCATCACTTGCCAGTC
CAGTCAGAGTGTTTATAGTAACTGGTTCTCCTGGTATCAGCAGAAACCAGGGAAAGCCCCTAAGCTCCTGATCT
ATTCTGCATCCACTCTGGCATCTGGGGTCCCATCAAGGTTCAGCGGCAGTGGATCTGGGACAGAATTCACTCTC
ACCATCAGCAGCCTGCAGCCTGATGATTTTGCAACTTATTACTGCGCAGGCGGTTACAATACTGTTATTGATAC
TTTTGCTTTCGGCGGAGGGACCAAGGTGGAGATCAAA >SEQ ID: 32 anti-4-1BB 460C3 VLv1 aa
DIQMTQSPSTLSASVGDRVTITCQSSQSVYSNWFSWYQQKPGKAPKLLIYSASTLASGVPSRFSGSGSGTEFTL
TISSLQPDDFATYYCAGGYNTVIDTFAFGGGTKVEIK >SEQ ID: 33 anti-ROR1 324C6 VHv2 nt
CAGTCGCTGGTGGAGTCTGGGGGAGGCTTGGTCCAGCCTGGGGGGTCCCTGAGACTCTCCTGTACTGCCTCTGG
ATTCTCCCTCAGTAGGTACTACATGACCTGGGTCCGCCAGGCTCCAGGGAAGGGGCTGGAGTGGATCGGAACCA
TTTATACTAGTGGTAGTACATGGTACGCGAGCTGGACAAAAGGCAGATTCACCATCTCCAAAGACAATACCAAG
AACACGGTGGATCTTCAAATGAACAGCCTGAGAGCCGAGGACACGGCTGTGTATTACTGTGCGAGATCCTATTA
TGGCGGTGATAAGACTGGTTTAGGCATCTGGGGCCAGGGAACTCTGGTTACCGTCTCTTCA >SEQ ID: 34 anti-ROR1 324C6 VHv2 nt
QSLVESGGGLVQPGGSLRLSCTASGFSLSRYYMTWVRQAPGKGLEWIGTIYTSGSTWYASWTKGRFTISKDNTK
NTVDLQMNSLRAEDTAVYYCARSYYGGDKTGLGIWGQGTLVTVSS >SEQ ID: 35 anti-ROR1 324C6 VLv1 nt
GACATCCAGATGACCCAGTCTCCTTCCACCCTGTCTGCATCTGTAGGAGACAGAGTCACCATCACTTGCCAGGC
CAGTCAGAGCATTGATAGTTGGTTATCCTGGTATCAGCAGAAACCAGGGAAAGCCCCTAAGCTCCTGATCTATC
AGGCATCCACTCTGGCATCTGGGGTCCCATCAAGGTTCAGCGGCAGTGGATCTGGGACAGAGTTCACTCTCACC
ATCAGCAGCCTGCAGCCTGATGATTTTGCAACTTATTACTGCCAATCTGCTTATGGTGTTAGTGGTACTAGTAG
TTATTTATATACTTTCGGCGGAGGGACCAAGGTGGAGATCAAA >SEQ ID: 36 anti-ROR1 324C6 VLv1 aa
DIQMTQSPSTLSASVGDRVTITCQASQSIDSWLSWYQQKPGKAPKLLIYQASTLASGVPSRFSGSGSGTEFTLT
ISSLQPDDFATYYCQSAYGVSGTSSYLYTFGGGTKVEIK >SEQ ID: 37 anti-ROR1 323H7 VHv4 nt
GAGGTGCAGCTGTTGGAGTCTGGGGGAGGCTTGGTACAGCCTGGGGGGTCCCTGAGACTCTCCTGTGCAGCCTC
TGGATTCACCATCAGTCGCTACCACATGACTTGGGTCCGCCAGGCTCCAGGGAAGGGGCTGGAGTGGATCGGAC
ATATTTATGTTAATAATGATGACACAGACTACGCGAGCTCCGCGAAAGGCCGGTTCACCATCTCCAGAGACAAT
TCCAAGAACACGCTGTATCTGCAAATGAACAGCCTGAGAGCCGAGGACACGGCCACCTATTTCTGTGCGAGATT
GGATGTTGGTGGTGGTGGTGCTTATATTGGGGACATCTGGGGCCAGGGAACTCTGGTTACCGTCTCTTCA >SEQ ID: 38 anti-ROR1 323H7 VHv4 aa
EVQLLESGGGLVQPGGSLRLSCAASGFTISRYHMTWVRQAPGKGLEWIGHIYVNNDDTDYASSAKGRFTISRDN
SKNTLYLQMNSLRAEDTATYFCARLDVGGGGAYIGDIWGQGTLVTVSS >SEQ ID: 39 anti-ROR1 323H7 VLv1 nt
GACATCCAGATGACCCAGTCTCCATCCTCCCTGTCTGCATCTGTAGGAGACAGAGTCACCATCACTTGCCAGTC
CAGTCAGAGTGTTTATAACAACAACGACTTAGCCTGGTATCAGCAGAAACCAGGGAAAGTTCCTAAGCTCCTGA
TCTATTATGCTTCCACTCTGGCATCTGGGGTCCCATCTCGGTTCAGTGGCAGTGGATCTGGGACAGATTTCACT
CTCACCATCAGCAGCCTGCAGCCTGAAGATGTTGCAACTTATTACTGTCAGGCGGTTATGATACGGATGGTCT
TGATACGTTTGCTTTCGGCGGAGGGACCAAGGTGGAGATCAAA

SEQUENCE LISTING

>SEQ ID: 40 anti-ROR1 323H7 VLv1 aa
DIQMTQSPSSLSASVGDRVTITC<u>QSSQSVYNNNDLA</u>WYQQKPGKVPKLLIY<u>YASTLAS</u>GVPSRFSGSGSGTDFT
LTISSLQPEDVATYYC<u>AGGYDTDGLDTFA</u>FGGGTKVEIK >SEQ ID: 41 anti-ROR1 338H4 VHv3 nt
GAGGTGCAGCTGGTGGAGTCTGGGGGAGGCTTGGTCCAGCCTGGGGGGTCCCTGAGACTCTCCTGTACTGCCTC
TGGATTCTCCCTCAGTAGCTATGCAATGAGCTGGGTCCGCCAGGCTCCAGGGAGGGGGCTGGAGTGGATCGGAA
TCATTTATGCTAGTGGTAGCACATACTACGCGAGCTCGGCGAAAGGCAGATTCACCATCTCCAAAGACAATACC
AAGAACACGGTGGATCTTCAAATGAACAGCCTGAGAGCCGAGGACACGGCTGTGTATTACTGTGCGAGAATTTA
TGACGGCATGGACCTCTGGGGCCAGGGAACTCTGGTTACCGTCTCTTCA >SEQ ID: 42 anti-ROR1 338H4 VHv3 aa
EVQLVESGGGLVQPGGSLRLSCTASGFSL<u>SSYAMS</u>WVRQAPGRGLEWIG<u>IIYASGSTYYASSAKG</u>RFTISKDNT
KNTVDLQMNSLRAEDTAVYYCAR<u>IYDGMDL</u>WGQGTLVTVSS >SEQ ID: 43 anti-ROR1 338H4 VLv4 nt
GACATCCAGATGACCCAGTCTCCATCCTCCCTGTCTGCATCTGTAGGAGACAGAGTCACCATCAATTGCCAGGC
CAGTCAGAACATTTACAGCTACTTATCCTGGTATCAGCAGAAACCAGGGAAAGTTCCTAAGCGCCTGATCTATC
TGGCATCTACTCTGGCATCTGGGGTCCCATCTCGGTTCAGTGGCAGTGGATCTGGGACAGATTACACTCTCACC
ATCAGCAGCCTGCAGCCTGAAGATGTTGCAACTTATTACTGTCAAAGCAATTATAACGGTAATTATGGTTTCGG
CGGAGGGACCAAGGTGGAGATCAAA >SEQ ID: 44 anti-ROR1 338H4 VLv4 aa
DIQMTQSPSSLSASVGDRVTINCQ<u>ASQNIYSYLS</u>WYQQKPGKVPKRLIY<u>LASTLAS</u>GVPSRFSGSGSGTDYTLT
ISSLQPEDVATYYC<u>QSNYNGNYG</u>FGGGTKVEIK >SEQ ID: 45 anti-ROR1 330F11 VHv1 nt
GAGGTGCAGCTGGTGGAGTCTGGGGGAGGCTTGGTCCAGCCTGGGGGGTCCCTGAGACTCTCCTGTGCAGCCTC
TGGATTCTCCCTCAATAACTACTGGATGAGCTGGGTCCGCCAGGCTCCAGGGAAGGGGCTGGAGTGGATCGGAA
CCATTAGTAGTGGTGCGTATACATGGTTCGCCACCTGGGCGACAGGCAGATTCACCATCTCCAGAGACAATTCC
AAGAACACGCTGTATCTTCAAATGAACAGCCTGAGAGCCGAGGACACGGCTGTGTATTACTGTGCGAGATATTC
TTCTACTACTGATTGGACCTACTTTAACATCTGGGGCCAGGGAACTCTGGTTACCGTCTCTTCA >SEQ ID: 46 anti-ROR1 330F11 VHv1 aa
EVQLVESGGGLVQPGGSLRLSCAASGFSL<u>NNYWMS</u>WVRQAPGKGLEWIG<u>TISSGAYTWFATWATG</u>RFTISRDNS
KNTLYLQMNSLRAEDTAVYYCAR<u>YSSTTDWTYFNI</u>WGQGTLVTVSS >SEQ ID: 47 anti-ROR1 330F11 VLv1 nt
GACATCCAGATGACCCAGTCTCCTTCCACCCTGTCTGCATCTGTAGGAGACAGAGTCACCATCACTTGCCAGGC
CAGTCAGAGCATTAATAACTACTTAGCCTGGTATCAGCAGAAACCAGGGAAAGCCCCTAAGCTCCTGATCTATA
GGGCATCCACTCTGGAATCTGGGGTCCCATCAAGGTTCAGCGGCAGTGGATCTGGGACAGAATTCACTCTCACC
ATCAGCAGCCTGCAGCCTGATGATTTTGCAACTTATTACTGCCAAAGCTATAATGGTGTTGGTAGGACTGCTTT
CGGCGGAGGGACCAAGGTGGAGATCAAA >SEQ ID: 48 anti-ROR1 330F11 VLv1 aa
DIQMTQSPSTLSASVGDRVTITC<u>QASQSINNYLA</u>WYQQKPGKAPKLLIY<u>RASTLES</u>GVPSRFSGSGSGTEFTLT
ISSLQPDDFATYYC<u>QSYNGVGRTA</u>FGGGTKVEIK >SEQ ID: 49 anti-EGFRvIII mAb 806 VH nt
GATGTGCAGCTTCAGGAGTCGGGACCTAGCCTGGTGAAACCTTCTCAGTCTCTGTCCCTCACCTGCACTGTCAC
TGGCTACTCAATCACCAGTGATTTTGCCTGGAACTGGATTCGGCAGTTTCCAGGAAACAAGCTGGAGTGGATGG
GCTACATAAGTTATAGTGGTAACACTAGGTACAACCCATCTCTCAAAAGTCGAATCTCTATCACTCGCGACACA
TCCAAGAACCAATTCTTCCTGCAGTTGAACTCTGTGACTATTGAGGACACAGCCACATATTACTGTGTAACGGC
GGGACGCGGGTTTCCTTATTGGGGCCAAGGGACTCTGGTCACTGTCTCTGCA >SEQ ID: 50 anti-EGFRvIII mAb 806 VH aa
DVQLQESGPSLVKPSQSLSLTCTVTGYSIT<u>SDFAWN</u>WIRQFPGNKLEWMG<u>YISYSGNTRYNPSLKS</u>RISITRDT
SKNQFFLQLNSVTIEDTATYYCVT<u>AGRGFPY</u>WGQGTLVTVSA >SEQ ID: 51 anti-EGFRvIII mAb 806 VL nt
GACATCCTGATGACCCAATCTCCATCCTCCATGTCTGTATCTCTGGGAGACACAGTCAGCATCACTTGCCATTC
AAGTCAGGACATTAACAGTAATATAGGGTGGTTGCAGCAGAGACCAGGGAAATCATTTAAGGGCCTGATCTATC
ATGGAACCAACTTGGACGATGAAGTTCCATCAAGGTTCAGTGGCAGTGGATCTGGAGCCGATTATTCTCTCACC
ATCAGCAGCCTGGAATCTGAAGATTTTGCAGACTATTACTGTGTACAGTATGCTCAGTTTCCGTGGACGTTCGG
TGGAGGCACCAAGCTGGAAATCAAA >SEQ ID: 52 anti-EGFRvIII mAb 806 VL aa
DILMTQSPSSMSVSLGDTVSITC<u>HSSQDINSNIG</u>WLQQRPGKSFKGLIY<u>HGTNLDD</u>EVPSRFSGSGSGADYSLT
ISSLESEDFADYYC<u>VQYAQFPWT</u>FGGGTKLEIK >SEQ ID: 53 anti-CD19 21D4 VH nt
GAGGTGCAGCTGGTGCAGTCTGGAGCAGAGGTGAAGAAACCAGGAGAGTCTCTGAAGATCTCCTGTAAGGGTTC
TGGATACAGCTTTAGCAGTTCATGGATCGGCTGGGTGCGCCAGGCACCTGGGAAGGCCTGGAATGGATGGGA
TCATCTATCCTGATGACTCTGATACCAGATACAGTCCATCCTTCCAAGGCCAGGTCACCATCTCAGCCGACAAG
TCCATCAGGACTGCCTACCTGCAGTGGAGTAGCCTGAAGGCCTCGGACACCGCTATGTATTACTGTGCGAGACA
TGTTACTATGATTTGGGGAGTTATTATTGACTTCTGGGGCCAGGGAACCCTGGTCACCGTCTCCTCA

SEQUENCE LISTING

>SEQ ID: 54 anti-CD19 21D4 VH aa
EVQLVQSGAEVKKPGESLKISCKGSGYSFS<u>SSWIG</u>WVRQAPGKGLEWMG<u>IIYPDDSDTRYSPSFQG</u>QVTISADK
SIRTAYLQWSSLKASDTAMYYCAR<u>HVTMIWGVIIDF</u>WGQGTLVTSS >SEQ ID: 55 anti-CD19 21D4 VL nt
GCCATCCAGTTGACCCAGTCTCCATCCTCCCTGTCTGCATCTGTAGGAGACAGAGTCACCATCACTTGCCGGGC
AAGTCAGGGCATTAGCAGTGCTTTAGCCTGGTATCAGCAGAAACCAGGGAAAGCTCCTAAGCTCCTGATCTATG
ATGCCTCCAGTTTGGAAAGTGGGGTCCCATCAAGGTTCAGCGGCAGTGGATCTGGGACAGATTTCACTCTCACC
ATCAGCAGCCTGCAGCCTGAAGATTTTGCAACTTATTACTGTCAACAGTTTAATAGTTACCCATTCACTTTCGG
CCCTGGGACCAAAGTGGATATCAAA >SEQ ID: 56 anti-CD19 21D4 VL aa
AIQLTQSPSSLSASVGDRVTITC<u>RASQGISSALA</u>WYQQKPGKAPKLLIY<u>DASSLES</u>GVPSRFSGSGSGTDFTLT
ISSLQPEDFATYYC<u>QQFNSYPFT</u>FGPGTKVDIK >SEQ ID: 57 anti-FITC4-4-20 VH nt
GAGGTGAAGCTGGATGAGACTGGAGGAGGCTTGGTGCAACCTGGGAGGCCCATGAAACTCTCCTGTGTTGCCTC
TGGATTCACTTTTAGTGACTACTGGATGAACTGGGTCCGCCAGTCTCCAGAGAAAGGACTGGAGTGGGTAGCAC
AAATTAGAAACAAACCTTATAATTATGAAACATATTATTCAGATTCTGTGAAAGGCAGATTCACCATCTCAAGA
GATGATTCCAAAAGTAGTGTCTACCTGCAAATGAACAACTTAAGAGTTGAAGACATGGGTATCTATTACTGTAC
GGGTTCTTACTATGGTATGGACTACTGGGGTCAAGGAACCTCAGTCACCGTCTCCTCA >SEQ ID: 58 anti-FITC 4-4-20 VH aa
EVKLDETGGGLVQPGRPMKLSCVASGFTFS<u>DYWMN</u>WVRQSPEKGLEWVA<u>QIRNKPYNYETYYSDSVKG</u>RFTISR
DDSKSSVYLQMNNLRVEDMGIYYCTG<u>SYYGMDY</u>WGQGTSVTVSS >SEQ ID: 59 anti-FITC 4-4-20 VL nt
GATGTCGTGATGACCCAAACTCCACTCTCCCTGCCTGTCAGTCTTGGAGATCAAGCCTCCATCTCTTGCAGATC
TAGTCAGAGCCTTGTACACAGTAATGGAAACACCTATTTACGTTGGTACCTGCAGAAGCCAGGCCAGTCTCCAA
AGGTCCTGATCTACAAAGTTTCCAACCGATTTTCTGGGGTCCCAGACAGGTTCAGTGGCAGTGGATCAGGGACA
GATTTCACACTCAAGATCAGCAGAGTGGAGGCTGAGGATCTGGGAGTTTATTTCTGCTCTCAAAGTACACATGT
TCCGTGGACGTTCGGTGGAGGCACCAAGCTGGAAATCAAA >SEQ ID: 60 anti-FITC 4-4-20 VL aa
DVVMTQTPLSLPVSLGDQASISC<u>RSSQSLVHSNGNTYLR</u>WYLQKPGQSPKVLIY<u>KVSNRFS</u>GVPDRFSGSGSGT
DFTLKISRVEAEDLGVYFC<u>SQSTHVPWT</u>FGGGTKLEIK >SEQ ID: 61 human IgG1 null (G1m-fa with ADCC/CDC null mutations) nt
GCTAGCACCAAGGGCCCATCGGTCTTCCCCCTGGCACCCTCCTCCAAGAGCACCTCTGGGGGCACAGCGGCCCT
GGGCTGCCTGGTCAAGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAACACCAAGGTGGACAAGAGAGTTGA
GCCCAAATCTTGTGACAAAACTCACACATGCCCACCGTGCCCAGCACCTGAAGCCGCGGGGGCACCGTCAGTCT
TCCTCTTCCCCCCAAAACCCAAGGACACCCTCATGATCTCCCGGACCCCTGAGGTCACATGCGTGGTGGTGGAC
GTGAGCCACGAAGACCCTGAGGTCAAGTTCAACTGGTACGTGGACGGCGTGGAGGTGCATAATGCCAAGACAAA
GCCGCGGGAGGAGCAGTACAACAGCACGTACCGTGTGGTCAGCGTCCTCACCGTCCTGCACCAGGACTGGCTGA
ATGGCAAGGAGTACAAGTGCGCGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGATGAGCTGACCAAGAACCAGGTCAG
CCTGACCTGCCTGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTATAGCAAGCTCACCGTGGAC
AAGAGCAGGTGGCAGCAGGGGAACGTCTTCTCATGCTCCGTGATGCATGAGGCTCTGCACAACCACTACACGCA
GAAGAGCCTCTCCCTGTCTCCGGGT >SEQ ID: 62 human IgG1 null (G1m-fa with ADCC/CDC null mutations) aa
ASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKRVEPKSCDKTHTCPPCPAPEAAGAPSVFLFPPKPKDTLMISRTPEVTCVVVD
VSHEDPEVKFNWYVDGVEVHNAKTKPREEQYNSTYRVVSVLTVLHQDWLNGKEYKCAVSNKALPAPIEKTISKA
KGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG >SEQ ID: 63 human Ig Kappa nt
CGTACGGTGGCTGCACCATCTGTCTTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGAAGGTGGATAACGCCCTCCAATCGG
GTAACTCCCAGGAGAGTGTCACAGAGCAGGACAGCAAGGACAGCACCTACAGCCTCAGCAGCACCCTGACGCTG
AGCAAAGCAGACTACGAGAAACACAAAGTCTACGCCTGCGAAGTCACCCATCAGGGCCTGAGCTCGCCCGTCAC
AAAGAGCTTCAACAGGGGAGAGTGT >SEQ ID: 64 human Ig Kappa aa
RTVAAPSVFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC >SEQ ID: 65 SI-35E18 (60C3-L1H1-scFv x P1230C6-Fab x 323H7-H4L1-scFv x
284A10-H1L1-scFv) heavy chain nt
GACATCCAGATGACCCAGTCTCCTTCCACCCTGTCTGCATCTGTAGGAGACAGAGTCACCATCACTTGCCAGTC
CAGTCAGAGTGTTTATAGTAACTGGTTCTCCTGGTATCAGCAGAAACCAGGGAAAGCCCCTAAGCTCCTGATCT
ATTCTGCATCCACTCTGGCATCTGGGGTCCCATCAAGGTTCAGCGGCAGTGGATCTGGGACAGAATTCACTCTC

```
                           SEQUENCE LISTING

ACCATCAGCAGCCTGCAGCCTGATGATTTTGCAACTTATTACTGCGCAGGCGGTTACAATACTGTTATTGATAC
TTTTGCTTTCGGCGGAGGGACCAAGGTGGAGATCAAAGGCGGTGGCGGTAGTGGGGGAGGCGGTTCTGGCGGCG
GAGGGTCCGGCGGTGGAGGATCAGAGGTGCAGCTGTTGGAGTCTGGGGGAGGCTTGGTACAGCCTGGGGGGTCC
CTGAGACTCTCCTGTGCAGCCTCTGGAATCGACTTCAGTAGGAGATACTACATGTGCTGGGTCCGCCAGGCTCC
AGGGAAGGGGCTGGAGTGGATCGCATGCATATATACTGGTAGCCGCGATACTCCTCACTACGCGAGCTCCGCGA
AAGGCCGGTTCACCATCTCCAGAGACAATTCCAAGAACACGCTGTATCTGCAAATGAACAGCCTGAGAGCCGAG
GACACGGCCGTATATTACTGTGCGAGAGAAGGTAGCCTGTGGGGCCAGGGAACCCTGGTCACCGTCTCGAGCGG
CGGTGGAGGGTCCGGCGGTGGTGGATCCCAGTCGGTGGAGGAGTCTGGGGGAGGCTTGGTCCAGCCTGGGGGGT
CCCTGAGACTCTCCTGTACAGCCTCTGGAATCGACCTTAATACCTACGACATGATCTGGGTCCGCCAGGCTCCA
GGGCAAGGGGCTAGAGTGGGTTGGAATCATTACTTATAGTGGTAGTAGATACTACGCGAACTGGGCGAAAGGCCG
ATTCACCATCTCCAAAGACAATACCAAGAACACGGTGTATCTGCAAATGAACAGCCTGAGAGCTGAGGACACGG
CTGTGTATTACTGTGCCAGAGATTATATGAGTGGTTCCCACTTGTGGGGCCAGGGAACCCTGGTCACCGTCTCT
AGTGCTAGCACCAAGGGCCCATCGGTCTTCCCCCTGGCACCCTCCTCCAAGAGCACCTCTGGGGGCACAGCGGC
CCTGGGCTGCCTGGTCAAGGACTACTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTCAGCAGCGTGGTGACCGTGCCCTCC
AGCAGCTTGGGCACCCAGACCTACATCTGCAACGTGAATCACAAGCCCAGCAACACCAAGGTGGACAAGAGAGT
TGAGCCCAAATCTTGTGACAAAACTCACACATGCCCACCGTGCCCAGCACCTGAAGCCGCGGGGGCACCGTCAG
TCTTCCTCTTCCCCCCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACCGTCCTGCACCAGGACTGGC
TGAATGGCAAGGAGTACAAGTGCGCGGTCTCCAACAAAGCCCTCCCAGCCCCCATCGAGAAAACCATCTCCAAA
GCCAAAGGGCAGCCCCGAGAACCACAGGTGTATACCCTGCCCCCATCCCGGGATGAGCTGACCAAGAACCAGGT
CAGCCTGACCTGCCTGGTCAAAGGCTTCTATCCCAGCGACATCGCCGTGGAGTGGGAGAGCAATGGGCAGCCGG
AGAACAACTACAAGACCACGCCTCCCGTGCTGGACTCCGACGGCTCCTTCTTCCTCTATAGCAAGCTCACCGTG
GACAAGAGCAGGTGGCAGCAGGGGAACGTCTTCTCATGCTCCGTGATGCATGAGGCTCTGCACAACCACTACAC
GCAGAAGAGCCTCTCCCTGTCTCCGGGTGGCGGTGGAGGGTCCGGCGGTGGTGGATCCGAGGTGCAGCTGTTGG
AGTCTGGGGGAGGCTTGGTACAGCCTGGGGGGTCCCTGAGACTCTCCTGTGCAGCCTCTGGATTCACCATCAGT
CGCTACCACATGACTTGGGTCCGCCAGGCTCCAGGGAAGGGGCTGGAGTGGATCGGACATATTTATGTTAATAA
TGATGACACAGACTACGCGAGCTCCGCGAAAGGCCGGTTCACCATCTCCAGAGACAATTCCAAGAACACGCTGT
ATCTGCAAATGAACAGCCTGAGAGCCGAGGACACGGCCACCTATTTCTGTGCGAGATTGGATGTTGGTGGTGGT
GGTGCTTATATTGGGGACATCTGGGGCCAGGGAACTCTGGTTACCGTCTCTTCAGGCGGTGGCGGTAGTGGGGG
AGGCGGTTCTGGCGGCGGAGGGTCCGGCGGTGGAGGATCAGACATCCAGATGACCCAGTCTCCATCCTCCCTGT
CTGCATCTGTAGGAGACAGAGTCACCATCACTTGCCAGTCCAGTCAGAGTGTTTATAACAACAACGACTTAGCC
TGGTATCAGCAGAAACCAGGGAAAGTTCCTAAGCTCCTGATCTATTATGCTTCCACTCTGGCATCTGGGGTCCC
ATCTCGGTTCAGTGGCAGTGGATCTGGACAGATTTCACTCTCACCATCAGCAGCCTGCAGCCTGAAGATGTTG
CAACTTATTACTGTGCAGGCGGTTATGATACGGATGGTCTTGATACGTTTGCTTTCGGCGGAGGGACCAAGGTG
GAGATCAAAGGCGGTGGAGGGTCCGGCGGTGGTGGATCCGAGGTGCAGCTGGTGGAGTCTGGGGGAGGCTTGGT
CCAGCCTGGGGGGTCCCTGAGACTCTCCTGTGCAGCCTCTGGATTCACCATCAGTACCAATGCAATGAGCTGGG
TCCGCCAGGCTCCAGGGAAGGGGCTGGAGTGGATCGGAGTCATTACTGGTCGTGATATCACATACTACGCGAGC
TGGGCGAAAGGCAGATTCACCATCTCCAGAGACAATTCCAAGAACACGCTGTATCTTCAAATGAACAGCCTGAG
AGCCGAGGACACGGCTGTGTATTACTGTGCGCGACGGGATGGATCATCTGCTATTACTAGTAACAACATTTGGG
GCCAAGGAACTCTGGTCACCGTTTCTTCAGGCGGTGGCGGTAGTGGGGGAGGCGGTTCTGGCGGCGGAGGGTCC
GGCGGTGGAGGATCAGACGTCGTGATGACCCAGTCTCCTTCCACCCTGTCTGCATCTGTAGGAGACAGAGTCAC
CATCAATTGCCAAGCCAGTGAGAGCATTAGCAGTTGGTTAGCCTGGTATCAGCAGAAACCAGGGAAAGCCCCTA
AGCTCCTGATCTATGAAGCATCCAAACTGGCATCTGGGGTCCCATCAAGGTTCAGCGGCAGTGGATCTGGGACA
GAGTTCACTCTCACCATCAGCAGCCTGCAGCCTGATGATTTTGCAACTTATTACTGCCAAGGCTATTTTTATTT
TATTAGTCGTACTTATGTAAATTCTTTCGGCGGAGGGACCAAGGTGGAGATCAAA
```

>SEQ ID: 66 SI-35E18 (460C3-L1H1-scFv x P1230C6-Fab x 323H7-H4L1-scFv x
284A10-H1L1-scFv) heavy chain aa
DIQMTQSPSTLSASVGDRVTITCQSSQSVYSNWFSWYQQKPGKAPKLLIYSASTLASGVPSRFSGSGSGTEFTL
TISSLQPDDFATYYCAGGYNTVIDTFAFGGGTKVEIK (anti-4-1BB13 460C3 VLv1)

GGGGSGGGGSGGGGSGGGGS (Gly$_4$Ser)x4 linker

EVQLLESGGGLVQPGGSLRLSCAASGIDFSRRYYMCWVRQAPGKGLEWIACIYTGSRDTPHYASSAKGRFTISR
DNSKNTLYLQMNSLRAEDTAVYYCAREGSLWGQGTLVTVSS (anti-4-1BB13 460C3 VHv1)
GGGGSGGGGS (Gly$_4$Ser)x2 linker QSVEESGGGLVQPGGSLRLSCTASGIDLNTYDMIWVRQAPGKGLEWVGIITYSGSRYYANWAKGRFTISKDNTK
NTVYLWNSLRAEDTAVYYCARDYMSGSHLWGQGTLVTVSS(anti-PD-L1 PL23006 VHv3)

ASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKRVEPKSCDKTHTCPPCPAPEAAGAPSVFLFPPKPKDTLMISRTPEVTCVVVD
VSHEDPEVKFNWYVDGVEVHNAKTKPREEQYNSTYRVVSVLTVLHQDWLNGKEYKCAVSNKALPAPIEKTISKA
KGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPG (human IgG1 null)

GGGGSGGGGS (Gly$_4$Ser)x2 linker

EVQLLESGGGLVQPGGSLRLSCAASGFTISRYHMTWVRQAPGKGLEWIGHIYVNNDDTDYASSAKGRFTISRDN
SKNTLYLQMNSLRAEDTATYFCARLDVGGGGAYIGDIWGQGTLVTVSS (anti-ROR1 323H7 VHv4)

GGGGSGGGGSGGGGSGGGGS (Gly$_4$Ser)x4 linker

DIQMTQSPSSLSASVGDRVTITCQSSQSVYNNNDLAWYQQKPGKVPKLLIYYASTLASGVPSRFSGSGSGTDFT
LTISSLQPEDVATYYCAGGYDTDGLDTFAFGGGTKVEIK (anti-ROR1 323H7 VLv1)

SEQUENCE LISTING

GGGGSGGGGS (Gly₄Ser)x2 linker

EVQLVESGGGLVQPGGSLRLSCAASGFTISTNAMSWVRQAPGKGLEWIGVITGRDITYYASWAKGRFTISRDNS
KNTLYLQMNSLRAEDTAVYYCARDGGSSAITSNNIWGQGTLVTVSS (anti-CD3 284A10 VHv1)

GGGGSGGGGSGGGGSGGGGS (Gly₄Ser)x4 linker

DVVMTQSPSTLSASVGDRVTINCQASESISSWLAWYQQKPGKAPKLLIYEASKLASGVPSRFSGSGSGTEFTLT
ISSLQPDDFATYYCQGYFYFISRTYVNSFGGGTKVEIK (anti-CD3 284A10 VLv1)

>SEQ ID: 67 SI-35E18 (460C3-L1H1-scFv x P1230C6-Fab x 323H7-H4L1-scFv x
284A10-H1L1-scFv) light chain nt
GCCTATGATATGACCCAGTCTCCATCTTCCGTGTCTGCATCTGTAGGAGACAGAGTCACCATCAAGTGTCAGGC
CAGTGAGGACATTTATAGCTTCTTGGCCTGGTATCAGCAGAAACCAGGGAAAGCCCCTAAGCTCCTGATCCATT
CTGCATCCTCTCTGGCATCTGGGGTCCCATCAAGGTTCAGCGGCAGTGGATCTGGGACAGATTTCACTCTCACC
ATCAGCAGCCTGCAGCCTGAAGATTTTGCAACTTACTATTGTCAACAGGGTTATGGTAAAAATAATGTTGATAA
TGCTTTCGGCGGAGGGACCAAGGTGGAGATCAAACGTACGGTGGCTGCACCATCTGTCTTCATCTTCCCGCCAT
CTGATGAGCAGTTGAAATCTGGAACTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAGTGTCACAGAGCAGGACAGCAAGGA
CAGCACCTACAGCCTCAGCAGCACCCTGACGCTGAGCAAAGCAGACTACGAGAAACACAAAGTCTACGCCTGCG
AAGTCACCCATCAGGGCCTGAGCTCGCCCGTCACAAAGAGCTTCAACAGGGGAGAGTGT >SEQ ID: 68 SI-35E18 (460C3-L1H1-scFv x P1230C6-Fab x 323H7-H4L1-scFv x
284A10-H1L1-scFv) light chain aa
AYDMTQSPSSVSASVGDRVTIKCQASEDIYSFLAWYQQKPGKAPKLLIHSASSLASGVPSRFSGSGSGTDFTLT
ISSLQPEDFATYYCQQGYGKNNVDNAFGGGTKVEIK (anti-PD-L1 PL23006 VLv2)

RTVAAPSVFIFPPSDEQLKSGTASVVCLLNNFYPREAKVQWKVDNALQSGNSQESVTEQDSKDSTYSLSSTLTL
SKADYEKHKVYACEVTHQGLSSPVTKSFNRGEC (human Ig Kappa)

| antigen | antibody | VH/VL | organism | patent | seq ID | Company |
|---|---|---|---|---|---|---|
| FITC | 4-4-20 | VH | artificial | US 2009/0042291 A1 | 14 | Xencor |
| FITC | 4-4-20 | VL | artificial | US 2009/0042291 A1 | 13 | Xencor |
| CD19 | 21D4 | VH | human | US 2009/0142349 A1 | 1 | Medarex |
| CD19 | 21D4 | VL | human | US 2009/0142349 A1 | 9 | Medarex |
| EGFRvIII | mAb 806 | VH | mouse | US 2009/0137782 A1 | 11 | Ludwig Institute |
| EGFRvIII | mAb 806 | VL | mouse | US 2009/0137782 A1 | 12 | Ludwig Institute |

NOTE:
EGFRvIII Systimmune sequence missing C-terminal Arginine.

Sequence Index:

| SEQ ID | Description |
|---|---|
| 1 | anti-CD3 284A10 VHv1 nt |
| 2 | anti-CD3 284A10 VHv1 aa |
| 3 | anti-CD3 284A10 VLv1 nt |
| 4 | anti-CD3 284A10 VLv1 aa |
| 5 | anti-CD3 480C8 VHv1 nt |
| 6 | anti-CD3 480C8 VHv1 aa |
| 7 | anti-CD3 480C8 VLv1 nt |
| 8 | anti-CD3 480C8 VLv1 aa |
| 9 | anti-PD-L1 PL230C6 VHv3 nt |
| 10 | anti-PD-L1 PL230C6 VHv3 aa |
| 11 | anti-PD-L1 PL230C6 VLv2 nt |
| 12 | anti-PD-L1 PL230C6 VLv2 aa |
| 13 | anti-PD-L1 PL221G5 VHv1 nt |
| 14 | anti-PD-L1 PL221G5 VHv1 aa |
| 15 | anti-PD-L1 PL221G5 VLv1 nt |
| 16 | anti-PD-L1 PL221G5 VLv1 aa |
| 17 | anti-PD-1 PD224D1 VHv2 nt |
| 18 | anti-PD-1 PD224D1 VHv2 aa |
| 19 | anti-PD-1 PD224D1 VLv2 nt |
| 20 | anti-PD-1 PD224D1 VLv2 aa |
| 21 | anti-4-1BB 420H5 VHv3 nt |

| SEQ ID | Description |
|---|---|
| 22 | anti-4-1BB 420H5 VHv3 aa |
| 23 | anti-4-1BB 420H5 VLv3 nt |
| 24 | anti-4-1BB 420H5 VHLv3 aa |
| 25 | anti-4-1BB 466F6 VHv2 nt |
| 26 | anti-4-1BB 466F6 VHv2 aa |
| 27 | anti-4-1BB 466F6 VLv5 nt |
| 28 | anti-4-1BB 466F6 VLv5 aa |
| 29 | anti-4-1BB 460C3 VHv1 nt |
| 30 | anti-4-1BB 460C3 VHv1 aa |
| 31 | anti-4-1BB 460C3 VLv1 nt |
| 32 | anti-4-1BB 460C3 VLv1 aa |
| 33 | anti-ROR1 324C6 VHv2 nt |
| 34 | anti-ROR1 324C6 VHv2 aa |
| 35 | anti-ROR1 324C6 VLv1 nt |
| 36 | anti-ROR1 324C6 VLv1 aa |
| 37 | anti-ROR1 323H7 VHv4 nt |
| 38 | anti-ROR1 323H7 VHv4 aa |
| 39 | anti-ROR1 323H7 VLv1 nt |
| 40 | anti-ROR1 323H7 VLv1 aa |
| 41 | anti-ROR1 338H4 VHv3 nt |
| 42 | anti-ROR1 338H4 VHv3 aa |
| 43 | anti-ROR1 338H4 VLv4 nt |
| 44 | anti-ROR1 338H4 VLv4 aa |
| 45 | anti-ROR1 330F11 VHv1 nt |
| 46 | anti-ROR1 330F11 VHv1 aa |
| 47 | anti-ROR1 330F11 VLv1 nt |
| 48 | anti-ROR1 330F11 VLv1 aa |
| 49 | anti-EGFRvIII mAb 806 VH nt |
| 50 | anti-EGFRvIII mAb 806 VH aa |
| 51 | anti-EGFRvIII mAb 806 VL nt |
| 52 | anti-EGFRvIII mAb 806 VL aa |
| 53 | anti-CD19 21D4 VH nt |
| 54 | anti-CD19 21D4 VH aa |
| 55 | anti-CD19 21D4 VL nt |
| 56 | anti-CD19 21D4 VL aa |
| 57 | anti-FITC 4-4-20 VH nt |
| 58 | anti-FITC 4-4-20 VH aa |
| 59 | anti-FITC 4-4-20 VL nt |
| 60 | anti-FITC 4-4-20 VL aa |
| 61 | human IgG1 null (G1m-fa with ADCC/CDC null mutations) nt |
| 62 | human IgG1 null (G1m-fa with ADCC/CDC null mutations) aa |
| 63 | human Ig Kappa nt |
| 64 | human Ig Kappa aa |
| 65 | SI-35E18 (60C3-L1H1-scFv × PL230C6-Fab × 323H7-H4L1-scFv × 284A10-H1L1-scFv) heavy chain nt |
| 66 | SI-35E18 (60C3-L1H1-scFv × PL230C6-Fab × 323H7-H4L1-scFv × 284A10-H1L1-scFv) heavy chain aa |
| 67 | SI-35E18 (60C3-L1H1-scFv × PL230C6-Fab × 323H7-H4L1-scFv × 284A10-H1L1-scFv) light chain nt |
| 68 | SI-35E18 (60C3-L1H1-scFv × PL230C6-Fab × 323H7-H4L1-scFv × 284A10-H1L1-scFv) light chain aa |

What is claimed is:

1. A tetra-specific antibody monomer having a N-terminal and a C-terminal, comprising in tandem from the N-terminal to the C-terminal,
a first scFv domain at the N-terminal,
a Fab domain, wherein the Fab domain comprises a CL having an amino acid SEQ ID NO. 64,
a Fc domain having an amino acid SEQ ID NO. 62,
a second scFv domain, and
a third scFv domain at the C-terminal, and
wherein the first scFv domain, the Fab domain, the second scFv domain and the third scFv domain have a combination of binding specificities selected from:
   i) the first scFv domain having a specificity against CD3, the Fab domain having a specificity against EGFR VIII, the second scFv domain having a specificity against PD-L1, and the third scFv domain having a specificity against 4-1BB, wherein the tetra-specific anti-body monomer comprises 3 complementarity determining regions (CDRs) of SEQ ID NO. 2 and 3 CDRs of SEQ ID NO: 4, 3 CDRs of SEQ ID NO. 10 and 3 CDRs of SEQ ID NO. 12, 3 CDRs of SEQ ID NO. 30 and 3 CDRs of SEQ ID NO. 32, and 3 CDRs of SEQ ID NO. 38 and 3 CDRs of SEQ ID NO: 40,
   ii) the first scFv domain having a binding specificity against CD3, the Fab domain having a binding affinity to CD19, the second scFv domain having a binding affinity to PD-L1, and the third scFv domain having a binding affinity to 4-1BB, wherein the tetra-specific anti-body monomer comprises 3 CDRs of SEQ ID NO. 2 and 3 CDRs of SEQ ID NO: 4, 3 CDRs of SEQ ID NO. 14 and 3 CDRs of SEQ ID NO. 16, 3 CDRs of SEQ ID NO: 26 and 3 CDRs of SEQ ID NO. 28, and 3 CDRs of SEQ ID NO: 54 and 3 CDRs of SEQ ID NO. 56, and
   iii) the first scFv domain having a binding affinity to 4-1BB, the Fab domain having a binding affinity to PD-L1, the second scFv domain having a binding affinity to ROR1, and the third scFv domain having a binding affinity to CD3, wherein the tetra-specific anti-body monomer comprises,
   a. 3 CDRs of SEQ ID NO. 2 and 3 CDRs of SEQ ID NO: 4, 3 CDRs of SEQ ID NO. 14 and 3 CDRs of SEQ ID NO. 16, 3 CDRs of SEQ ID NO: 26 and 3 CDRs of SEQ ID NO. 28, and 3 CDRs of SEQ ID NO: 54 and 3 CDRs of SEQ ID NO. 56; or
   b. 3 CDRs of SEQ ID NO. 2 and 3 CDRs of SEQ ID NO: 4, 3 CDRs of SEQ ID NO. 14 and 3 CDRs of SEQ ID NO. 16, 3 CDRs of SEQ ID NO. 22 and 3 CDRs of SEQ ID NO. 24, and 3 CDRs of SEQ ID NO. 50 and 3 CDRs of SEQ ID NO. 52.

2. The tetra-specific antibody monomer of claim 1, wherein the first scFv domain comprises an amino acid sequence having a sequency identity to SEQ ID NO. 2 and 4, the Fab domain comprises an amino acid sequence having a sequency identity to SEQ ID NO. 50 and 52, the second scFv domain comprises an amino acid sequence having a sequency identity to SEQ ID NO. 14 and 16, and the third scFv domain comprises an amino acid sequence having a sequency identity to SEQ ID NO. 22 and 24.

3. The tetra-specific antibody monomer of claim 1, wherein the first scFv domain comprises an amino acid sequence having a sequence identity to SEQ ID NO. 2 and 4, the Fab domain comprises an amino acid sequence having a sequence identity to SEQ ID NO. 54 and 56, the second scFv domain comprises an amino acid sequence having a sequence identity to SEQ ID NO. 14 and 16, and the third scFv domain comprises an amino acid sequence having a sequence identity to SEQ ID NO. 26 and 28.

4. The tetra-specific antibody monomer of claim 1, wherein the first scFv domain comprises an amino acid sequence having sequence identity to SEQ ID NO. 30 and 32, or SEQ ID NO. 26 and 28, the Fab domain comprises an amino acid sequence having sequence identity to SEQ ID NO. 10 and 12, the second scFv domain comprises an amino acid sequence having sequence identity to SEQ ID NO. 38 and 40, and the third scFv comprises an amino acid sequence having sequence identity to SEQ ID NO. 2 and 4.

5. The tetra-specific antibody monomer of claim 1, wherein the first scFv domain, the second scFv domain, or the third scFv domain comprises a gly-gly-gly-gly-ser (G4S)$_n$ linker having SEQ ID NO. 66, wherein n is 2, or 4.

6. The tetra-specific antibody monomer of claim 1, comprising an amino acid sequence having at least 98% sequence identity to SEQ ID NO. 02, 04, 06, 08, 10, 12, 14, 16, 18, 20, 22, 24, 26, 28, 30, 32, 34, 36, 38, 40, 42, 44, 46, 48, 50, 52, 54, 56, 58, 60, 62, or 64.

7. A scFv domain for the tetra-specific antibody monomer of claim 1,
comprising an amino acid sequence having at least 98% sequence identity to SEQ ID NO. 02, 04, 14, 16, 22, 24, 26, 28, 30, or 32.

8. A Fab domain for the tetra-specific antibody monomer of claim 1,
comprising an amino acid sequence having at least 98% sequence identity to SEQ ID NO. 10, 12, 50, 52, 54, 56, or 58.

9. A tetra-specific antibody, comprising a dimer of the tetra-specific antibody monomer of claim 1.

10. The tetra-specific antibody of claim 9, comprising an amino acid sequence having at least 98% sequence identity to SEQ ID NO. 66, and 68.

11. An isolated nucleic acid sequence, encoding an amino acid sequence having SEQ ID NO. 02, 04, 06, 08, 10, 12, 14, 16, 18, 20, 22, 24, 26, 28, 30, 32, 34, 36, 38, 40, 42, 44, 46, 48, 50, 52, 66 or 68.

12. An expression vector, comprising the isolated nucleic acid sequence of claim 11.

13. A host cell comprising the isolated nucleic acid sequence of claim 11, wherein the host cell is a prokaryotic cell or a eukaryotic cell.

14. A method for producing the tetra-specific antibody of claim 9, comprising culturing a host cell comprising one or more isolated nucleic acid sequences such that the DNA sequence encoding the tetra-specific antibody,
wherein the nucleic acid sequences are expressed, and
purifying the tetra-specific antibody.

15. A pharmaceutical composition, comprising a pharmaceutically acceptable carrier and the tetra-specific antibody of claim 9.

16. A method of treating a human subject with cancer, comprising administering to the subject an effective amount of the tetra-specific antibody according to claim 9.

\* \* \* \* \*

```
                           SEQUENCE LISTING

<160> NUMBER OF SEQ ID NOS: 68

<210> SEQ ID NO 1
<211> LENGTH: 360
<212> TYPE: DNA
<213> ORGANISM: Artificial Sequence
<220> FEATURE:
<223> OTHER INFORMATION: synthesized

<400> SEQUENCE: 1
gaggtgcagc tggtggagtc tgggggaggc ttggtccagc ctgggggtc cctgagactc      60 tcctgtgcag cctctggatt caccatcagt accaatgcaa tgagctgggt ccgccaggct     120
ccagggaagg ggctggagtg gatcggagtc attactggtc gtgatatcac atactacgcg     180
agctgggcga aaggcagatt caccatctcc agagacaatt ccaagaacac gctgtatctt     240
caaatgaaca gcctgagagc cgaggacacg gctgtgtatt actgtgcgcg cgacggtgga     300
tcatctgcta ttactagtaa caacatttgg ggccaaggaa ctctggtcac cgtttcttca     360
```

<210> SEQ ID NO 2
<211> LENGTH: 120
<212> TYPE: PRT
<213> ORGANISM: Artificial Sequence
<220> FEATURE:
<223> OTHER INFORMATION: synthesized

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Thr Ser Asn Asn Ile Trp Gly Gln
            100                 105                 110

Gly Thr Leu Val Thr Val Ser Ser
        115                 120
```

<210> SEQ ID NO 3
<211> LENGTH: 336
<212> TYPE: DNA
<213> ORGANISM: Artificial Sequence
<220> FEATURE:
<223> OTHER INFORMATION: synthesized

<400> SEQUENCE: 3

```
gacgtcgtga tgacccagtc tccttccacc ctgtctgcat ctgtaggaga cagagtcacc    60
atcaattgcc aagccagtga gagcattagc agttggttag cctggtatca gcagaaacca   120
gggaaagccc ctaagctcct gatctatgaa gcatccaaac tggcatctgg ggtcccatca   180
aggttcagcg gcagtggatc tgggacagag ttcactctca ccatcagcag cctgcagcct   240
gatgattttg caacttatta ctgccaaggc tattttatt ttattagtcg tacttatgta    300
aattctttcg gcggagggac caaggtggag atcaaa                             336
```

<210> SEQ ID NO 4
<211> LENGTH: 112
<212> TYPE: PRT
<213> ORGANISM: Artificial Sequence
<220> FEATURE:
<223> OTHER INFORMATION: synthesized

<400> SEQUENCE: 4

```
Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                65                  70                  75                  80
Asp Asp Phe Ala Thr Tyr Tyr Cys Gln Gly Tyr Phe Tyr Phe Ile Ser
                            85                  90                  95

Arg Thr Tyr Val Asn Ser Phe Gly Gly Gly Thr Lys Val Glu Ile Lys
            100                 105                 110
```

<210> SEQ ID NO 5
<211> LENGTH: 360
<212> TYPE: DNA
<213> ORGANISM: Artificial Sequence
<220> FEATURE:
<223> OTHER INFORMATION: synthesized

<400> SEQUENCE: 5

```
gaggtgcagc tggtggagtc tgggggaggc ttggtccagc ctgggggtc cctgagactc      60 tcctgtgcag cctctggaat cgacctcagt agcaatgcaa tgagctgggt ccgccaggct    120
ccagggaagg gctggagtg atcggagtc attactggtc gtgatatcac atactacgcg      180
agctgggcga aaggcagatt caccatctcc agagacaatt ccaagaacac gctgtatctt   240
caaatgaaca gcctgagagc cgaggacacg gctgtgtatt actgtgcgcg cgacggtgga   300
tcatctgcta ttaatagtaa gaacatttgg ggccaaggaa ctctggtcac cgtttcttca   360
```

<210> SEQ ID NO 6
<211> LENGTH: 120
<212> TYPE: PRT
<213> ORGANISM: Artificial Sequence
<220> FEATURE:
<223> OTHER INFORMATION: synthesized

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Ser Ser Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Asn Ser Lys Asn Ile Trp Gly Gln
            100                 105                 110

Gly Thr Leu Val Thr Val Ser Ser
        115                 120
```

<210> SEQ ID NO 7
<211> LENGTH: 336
<212> TYPE: DNA
<213> ORGANISM: Artificial Sequence
<220> FEATURE:
<223> OTHER INFORMATION: synthesized

<400> SEQUENCE: 7

```
gacatccaga tgacccagtc tccttccacc ctgtctgcat ctgtaggaga cagagtcacc      60
atcacttgcc aagccagtga gagcattagc agttggttag cctggtatca gcagaaacca    120
gggaaagccc ctaagctcct gatctatgaa gcatccaaac tggcatctgg ggtcccatca    180
```

-continued

```
aggttcagcg gcagtggatc tgggacagag ttcactctca ccatcagcag cctgcagcct    240
gatgattttg caacttatta ctgccaaggc tatttttatt ttattagtcg tacttatgta    300
aatgctttcg gcggagggac caaggtggag atcaaa                              336
```

<210> SEQ ID NO 8
<211> LENGTH: 112
<212> TYPE: PRT
<213> ORGANISM: Artificial Sequence
<220> FEATURE:
<223> OTHER INFORMATION: synthesized

<400> SEQUENCE: 8

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ala Phe Gly Gly Gly Thr Lys Val Glu Ile Lys
            100                 105                 110
```

<210> SEQ ID NO 9
<211> LENGTH: 345
<212> TYPE: DNA
<213> ORGANISM: Artificial Sequence
<220> FEATURE:
<223> OTHER INFORMATION: synthesized

<400> SEQUENCE: 9

```
cagtcggtgg aggagtctgg gggaggcttg gtccagcctg ggggtccct gagactctcc      60 tgtacagcct ctggaatcga ccttaatacc tacgacatga tctgggtccg ccaggctcca    120
ggcaaggggc tagagtgggt tggaatcatt acttatagtg gtagtagata ctacgcgaac    180
tgggcgaaag gccgattcac catctccaaa gacaatacca gaacacggt gtatctgcaa     240 atgaacagcc tgagagctga ggacacggct gtgtattact gtgccagaga ttatatgagt    300
ggttcccact gtgggggcca gggaaccctg gtcaccgtct ctagt                    345
```

<210> SEQ ID NO 10
<211> LENGTH: 115
<212> TYPE: PRT
<213> ORGANISM: Artificial Sequence
<220> FEATURE:
<223> OTHER INFORMATION: synthesized

<400> SEQUENCE: 10

```
Gln Ser Val Glu Glu Ser Gly Gly Gly Leu Val Gln Pro Gly Gly Ser
1               5                   10                  15

Leu Arg Leu Ser Cys Thr Ala Ser Gly Ile Asp Leu Asn Thr Tyr Asp
            20                  25                  30

Met Ile Trp Val Arg Gln Ala Pro Gly Lys Gly Leu Glu Trp Val Gly
        35                  40                  45
```

```
Ile Ile Thr Tyr Ser Gly Ser Arg Tyr Tyr Ala Asn Trp Ala Lys Gly
        50                  55                  60

Arg Phe Thr Ile Ser Lys Asp Asn Thr Lys Asn Thr Val Tyr Leu Gln
 65                  70                  75                  80

Met Asn Ser Leu Arg Ala Glu Asp Thr Ala Val Tyr Tyr Cys Ala Arg
                 85                  90                  95

Asp Tyr Met Ser Gly Ser His Leu Trp Gly Gln Gly Thr Leu Val Thr
            100                 105                 110

Val Ser Ser
    115

<210> SEQ ID NO 11
<211> LENGTH: 330
<212> TYPE: DNA
<213> ORGANISM: Artificial Sequence
<220> FEATURE:
<223> OTHER INFORMATION: synthesized

<400> SEQUENCE: 11
gcctatgata tgacccagtc tccatcttcc gtgtctgcat ctgtaggaga cagagtcacc      60
atcaagtgtc aggccagtga ggacatttat agcttcttgg cctggtatca gcagaaacca     120
gggaaagccc ctaagctcct gatccattct gcatcctctc tggcatctgg ggtcccatca     180
aggttcagcg gcagtggatc tgggacagat ttcactctca ccatcagcag cctgcagcct     240
gaagattttg caacttacta ttgtcaacag ggttatggta aaaataatgt tgataatgct     300
ttcggcggag ggaccaaggt ggagatcaaa                                      330

<210> SEQ ID NO 12
<211> LENGTH: 110
<212> TYPE: PRT
<213> ORGANISM: Artificial Sequence
<220> FEATURE:
<223> OTHER INFORMATION: synthesized

<400> SEQUENCE: 12

Ala Tyr Asp Met Thr Gln Ser Pro Ser Ser Val Ser Ala Ser Val Gly
 1               5                  10                  15

Asp Arg Val Thr Ile Lys Cys Gln Ala Ser Glu Asp Ile Tyr Ser Phe
             20                  25                  30

Leu Ala Trp Tyr Gln Gln Lys Pro Gly Lys Ala Pro Lys Leu Leu Ile
            35                  40                  45

His Ser Ala Ser Ser Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Gly Lys Asn Asn
                 85                  90                  95

Val Asp Asn Ala Phe Gly Gly Gly Thr Lys Val Glu Ile Lys
            100                 105                 110

<210> SEQ ID NO 13
<211> LENGTH: 366
<212> TYPE: DNA
<213> ORGANISM: Artificial Sequence
<220> FEATURE:
<223> OTHER INFORMATION: synthesized

<400> SEQUENCE: 13
gaggtgcagc tgttggagtc tgggggaggc ttggtacagc ctggggggtc cctgagactc      60
```

```
tcctgtgcag cctctggatt ctccttcagt agcgggtacg acatgtgctg ggtccgccag    120
gctccaggga aggggctgga gtggatcgca tgcattgctg ctggtagtgc tggtatcact    180
tacgacgcga actgggcgaa aggccggttc accatctcca gagacaattc caagaacacg    240
ctgtatctgc aaatgaacag cctgagagcc gaggacacgg ccgtatatta ctgtgcgaga    300
tcggcgtttt cgttcgacta cgccatggac ctctggggcc agggaaccct ggtcaccgtc    360
tcgagc                                                               366
```

```
<210> SEQ ID NO 14
<211> LENGTH: 122
<212> TYPE: PRT
<213> ORGANISM: Artificial Sequence
<220> FEATURE:
<223> OTHER INFORMATION: synthesized

<400> SEQUENCE: 14
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Ile Ala Cys Ile Ala Ala Gly Ser Ala Gly Ile Thr Tyr Asp Ala Asn
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ser Ala Phe Ser Phe Asp Tyr Ala Met Asp Leu Trp
            100                 105                 110

Gly Gln Gly Thr Leu Val Thr Val Ser Ser
        115                 120

```
<210> SEQ ID NO 15
<211> LENGTH: 330
<212> TYPE: DNA
<213> ORGANISM: Artificial Sequence
<220> FEATURE:
<223> OTHER INFORMATION: synthesized

<400> SEQUENCE: 15
gacatccaga tgacccagtc tccttccacc ctgtctgcat ctgtaggaga cagagtcacc     60
atcacttgcc aggccagtca gagcattagt tcccacttaa actggtatca gcagaaacca    120
gggaaagccc ctaagctcct gatctataag gcatccactc tggcatctgg gtcccatca    180 aggttcagcg gcagtggatc tgggacagaa tttactctca ccatcagcag cctgcagcct    240
gatgattttg caacttatta ctgccaacag ggttatagtt ggggtaatgt tgataatgtt    300
ttcggcggag ggaccaaggt ggagatcaaa                                     330
```

```
<210> SEQ ID NO 16
<211> LENGTH: 110
<212> TYPE: PRT
<213> ORGANISM: Artificial Sequence
<220> FEATURE:
<223> OTHER INFORMATION: synthesized

<400> SEQUENCE: 16
```

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Trp Gly Asn
                85                  90                  95

Val Asp Asn Val Phe Gly Gly Gly Thr Lys Val Glu Ile Lys
            100                 105                 110
```

<210> SEQ ID NO 17
<211> LENGTH: 345
<212> TYPE: DNA
<213> ORGANISM: Artificial Sequence
<220> FEATURE:
<223> OTHER INFORMATION: synthesized

<400> SEQUENCE: 17

```
gaggtgcagc tggtggagtc tgggggaggc ttggtccagc ctgggggtc cctgagactc      60
tcctgtacag cctctggatt ctccctaagt agctatgcaa tgagctgggt ccgccaggct    120
ccagggaagg ggctggagta catcggctac attggtgata ctactggcat agcctacgcg    180
agctgggcga atggcagatt caccatctcc aaagacaata ccaagaacac ggtggatctt    240
caaatgaaca gcctgagagc cgaggacacg gctgtgtatt actgtgcgag aggctggtcc    300
tacttagaca tctggggcca agggaccctg gtcaccgtct cgagc                    345
```

<210> SEQ ID NO 18
<211> LENGTH: 115
<212> TYPE: PRT
<213> ORGANISM: Artificial Sequence
<220> FEATURE:
<223> OTHER INFORMATION: synthesized

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Lys Gly Leu Glu Tyr Ile
        35                  40                  45

Gly Tyr Ile Gly Asp Thr Thr Gly Ile Ala Tyr Ala Ser Trp Ala Asn
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Gly Trp Ser Tyr Leu Asp Ile Trp Gly Gln Gly Thr Leu Val Thr
            100                 105                 110

Val Ser Ser
        115
```

<210> SEQ ID NO 19

<211> LENGTH: 327
<212> TYPE: DNA
<213> ORGANISM: Artificial Sequence
<220> FEATURE:
<223> OTHER INFORMATION: synthesized

<400> SEQUENCE: 19

```
gcccttgtga tgacccagtc tccatcctcc ctgtctgcat ctgtaggaga cagagtcacc    60
atcacttgcc aggccagtca gaacatttac agcaatttag cctggtatca gcagaaacca   120
gggaaagttc ctaagctcct gatctatcag gcctccactc tggcatctgg ggtcccatct   180
cggttcagtg gcagtggata tgggacagat ttcactctca ccatcagcag cctgcagcct   240
gaagatgttg caacttatta ctgtcaaggc ggttattata gtgctgccct taatactttc   300
ggcggaggga ccaaggtgga gatcaaa                                       327
```

<210> SEQ ID NO 20
<211> LENGTH: 109
<212> TYPE: PRT
<213> ORGANISM: Artificial Sequence
<220> FEATURE:
<223> OTHER INFORMATION: synthesized

<400> SEQUENCE: 20

```
Ala Leu Val Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Val Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gly Gly Tyr Tyr Ser Ala Ala
                85                  90                  95

Leu Asn Thr Phe Gly Gly Gly Thr Lys Val Glu Ile Lys
            100                 105
```

<210> SEQ ID NO 21
<211> LENGTH: 360
<212> TYPE: DNA
<213> ORGANISM: Artificial Sequence
<220> FEATURE:
<223> OTHER INFORMATION: synthesized

<400> SEQUENCE: 21

```
cagtcgctgg tggagtctgg gggaggcttg gtacagcctg gggggtccct gagactctcc    60
tgtgcagcct ctggattctc cttcagtagc aactactgga tgctgggt ccgccaggct    120
ccagggaagg ggctggagtg gatcgcatgc atttatgttg gtagtagtgg tgacacttac   180
tacgcgagct ccgcgaaagg ccggttcacc atctccagag acaattccaa gaacacgctg   240
tatctgcaaa tgaacagcct gagagccgag gacacggccg tatattactg tgcgagagat   300
agtagtagtt attatatgtt taacttgtgg ggccaggaa ccctggtcac cgtctcgagc   360
```

<210> SEQ ID NO 22
<211> LENGTH: 120
<212> TYPE: PRT
<213> ORGANISM: Artificial Sequence
<220> FEATURE:

<223> OTHER INFORMATION: synthesized

<400> SEQUENCE: 22

Gln Ser Leu Val Glu Ser Gly Gly Gly Leu Val Gln Pro Gly Gly Ser
1               5                   10                  15

Leu Arg Leu Ser Cys Ala Ala Ser Gly Phe Ser Phe Ser Asn Tyr
            20                  25                  30

Trp Ile Cys Trp Val Arg Gln Ala Pro Gly Lys Gly Leu Glu Trp Ile
        35                  40                  45

Ala Cys Ile Tyr Val Gly Ser Ser Gly Asp Thr Tyr Tyr Ala Ser Ser
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Ser Ser Tyr Tyr Met Phe Asn Leu Trp Gly Gln
            100                 105                 110

Gly Thr Leu Val Thr Val Ser Ser
        115                 120

<210> SEQ ID NO 23
<211> LENGTH: 336
<212> TYPE: DNA
<213> ORGANISM: Artificial Sequence
<220> FEATURE:
<223> OTHER INFORMATION: synthesized

<400> SEQUENCE: 23
gcccttgtga tgacccagtc tccttccacc ctgtctgcat ctgtaggaga cagagtcacc    60
atcaattgcc aggccagtga ggacattgat acctatttag cctggtatca gcagaaacca   120
gggaaagccc ctaagctcct gatcttttat gcatccgatc tggcatctgg ggtcccatca   180
aggttcagcg gcagtggatc tgggacagaa ttcactctca ccatcagcag cctgcagcct   240
gatgattttg caacttatta ctgccaaggc ggttactata ctagtagtgc tgatacgagg   300
ggtgctttcg gcggagggac caaggtggag atcaaa                             336

<210> SEQ ID NO 24
<211> LENGTH: 112
<212> TYPE: PRT
<213> ORGANISM: Artificial Sequence
<220> FEATURE:
<223> OTHER INFORMATION: synthesized

<400> SEQUENCE: 24

Ala Leu Val Met Thr Gln Ser Pro Ser Thr Leu Ser Ala Ser Val Gly
1               5                   10                  15

Asp Arg Val Thr Ile Asn Cys Gln Ala Ser Glu Asp Ile Asp Thr Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Gly Tyr Tyr Thr Ser Ser
                85                  90                  95

Ala Asp Thr Arg Gly Ala Phe Gly Gly Gly Thr Lys Val Glu Ile Lys

<210> SEQ ID NO 25
<211> LENGTH: 345
<212> TYPE: DNA
<213> ORGANISM: Artificial Sequence
<220> FEATURE:
<223> OTHER INFORMATION: synthesized

<400> SEQUENCE: 25

```
cggtcgctgg tggagtctgg ggggaggcttg gtccagcctg ggggtccct gagactctcc      60
tgtacagcct ctggattcac catcagtagc taccacatgc agtgggtccg ccaggctcca     120
gggaaggggc tggagtacat cggaaccatt agtagtggtg gtaatgtata ctacgcgagc     180
tccgcgagag gcagattcac catctccaga ccctcgtcca agaacacggt ggatcttcaa     240
atgaacagcc tgagagccga ggacacggct gtgtattact gtgcgagaga ctctggttat     300
agtgatccta tgtggggcca gggaaccctg gtcaccgtct cgagc                     345
```

<210> SEQ ID NO 26
<211> LENGTH: 115
<212> TYPE: PRT
<213> ORGANISM: Artificial Sequence
<220> FEATURE:
<223> OTHER INFORMATION: synthesized

<400> SEQUENCE: 26

```
Arg Ser Leu Val Glu Ser Gly Gly Gly Leu Val Gln Pro Gly Gly Ser
1               5                   10                  15
Leu Arg Leu Ser Cys Thr Ala Ser Gly Phe Thr Ile Ser Ser Tyr His
            20                  25                  30
Met Gln Trp Val Arg Gln Ala Pro Gly Lys Gly Leu Glu Tyr Ile Gly
        35                  40                  45
Thr Ile Ser Ser Gly Gly Asn Val Tyr Tyr Ala Ser Ser Ala Arg Gly
    50                  55                  60
Arg Phe Thr Ile Ser Arg Pro Ser Ser Lys Asn Thr Val Asp Leu Gln
65                  70                  75                  80
Met Asn Ser Leu Arg Ala Glu Asp Thr Ala Val Tyr Tyr Cys Ala Arg
                85                  90                  95
Asp Ser Gly Tyr Ser Asp Pro Met Trp Gly Gln Gly Thr Leu Val Thr
            100                 105                 110
Val Ser Ser
        115
```

<210> SEQ ID NO 27
<211> LENGTH: 333
<212> TYPE: DNA
<213> ORGANISM: Artificial Sequence
<220> FEATURE:
<223> OTHER INFORMATION: synthesized

<400> SEQUENCE: 27

```
gacgttgtga tgacccagtc tccatcttcc gtgtctgcat ctgtaggaga cagagtcacc      60
atcacctgtc aggccagtca gaacattagg acttacttat cctggtatca gcagaaacca     120
gggaaagccc ctaagctcct gatctatgct gcagccaatc tggcatctgg ggtcccatca     180
aggttcagcg gcagtggatc tgggacagat ttcactctca ccatcagcga cctggagcct     240
ggcgatgctg caacttacta ttgtcagtct acctatcttg gtactgatta tgttggcggt     300
gctttcggcg gagggaccaa ggtggagatc aaa                                  333
```

<210> SEQ ID NO 28
<211> LENGTH: 111
<212> TYPE: PRT
<213> ORGANISM: Artificial Sequence
<220> FEATURE:
<223> OTHER INFORMATION: synthesized

<400> SEQUENCE: 28

```
Asp Val Val Met Thr Gln Ser Pro Ser Ser Val Ser Ala Ser Val Gly
1               5                   10                  15

Asp Arg Val Thr Ile Thr Cys Gln Ala Ser Gln Asn Ile Arg Thr Tyr
            20                  25                  30

Leu Ser Trp Tyr Gln Gln Lys Pro Gly Lys Ala Pro Lys Leu Leu Ile
        35                  40                  45

Tyr Ala Ala Ala Asn Leu Ala Ser Gly Val Pro Ser Arg Phe Ser Gly
    50                  55                  60

Ser Gly Ser Gly Thr Asp Phe Thr Leu Thr Ile Ser Asp Leu Glu Pro
65                  70                  75                  80

Gly Asp Ala Ala Thr Tyr Tyr Cys Gln Ser Thr Tyr Leu Gly Thr Asp
                85                  90                  95

Tyr Val Gly Gly Ala Phe Gly Gly Gly Thr Lys Val Glu Ile Lys
            100                 105                 110
```

<210> SEQ ID NO 29
<211> LENGTH: 345
<212> TYPE: DNA
<213> ORGANISM: Artificial Sequence
<220> FEATURE:
<223> OTHER INFORMATION: synthesized

<400> SEQUENCE: 29

```
gaggtgcagc tgttggagtc tgggggaggc ttggtacagc ctggggggtc cctgagactc      60
tcctgtgcag cctctggaat cgacttcagt aggagatact acatgtgctg ggtccgccag     120
gctccaggga aggggctgga gtggatcgca tgcatatata ctggtagccg cgatactcct     180
cactacgcga gctccgcgaa aggccggttc accatctcca gagacaattc caagaacacg     240
ctgtatctgc aaatgaacag cctgagagcc gaggacacgg ccgtatatta ctgtgcgaga     300
gaaggtagcc tgtggggcca gggaaccctg gtcaccgtct cgagc                     345
```

<210> SEQ ID NO 30
<211> LENGTH: 115
<212> TYPE: PRT
<213> ORGANISM: Artificial Sequence
<220> FEATURE:
<223> OTHER INFORMATION: synthesized

<400> SEQUENCE: 30

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
             85                  90                  95

Tyr Cys Ala Arg Glu Gly Ser Leu Trp Gly Gln Gly Thr Leu Val Thr
            100                 105                 110

Val Ser Ser
        115

<210> SEQ ID NO 31
<211> LENGTH: 333
<212> TYPE: DNA
<213> ORGANISM: Artificial Sequence
<220> FEATURE:
<223> OTHER INFORMATION: synthesized

<400> SEQUENCE: 31
gacatccaga tgacccagtc tccttccacc ctgtctgcat ctgtaggaga cagagtcacc      60
atcacttgcc agtccagtca gagtgtttat agtaactggt tctcctggta tcagcagaaa    120
ccagggaaag cccctaagct cctgatctat tctgcatcca ctctggcatc tggggtccca    180
tcaaggttca gcggcagtgg atctgggaca gaattcactc tcaccatcag cagcctgcag    240
cctgatgatt ttgcaactta ttactgcgca ggcggttaca atactgttat tgatactttt    300
gctttcggcg agggaccaa ggtggagatc aaa                                  333

<210> SEQ ID NO 32
<211> LENGTH: 111
<212> TYPE: PRT
<213> ORGANISM: Artificial Sequence
<220> FEATURE:
<223> OTHER INFORMATION: synthesized

<400> SEQUENCE: 32

Asp Ile Gln Met Thr Gln Ser Pro Ser Thr Leu Ser Ala Ser Val Gly
1               5                  10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys
            100                 105                 110

<210> SEQ ID NO 33
<211> LENGTH: 357
<212> TYPE: DNA
<213> ORGANISM: Artificial Sequence
<220> FEATURE:
<223> OTHER INFORMATION: synthesized

<400> SEQUENCE: 33
cagtcgctgg tggagtctgg gggaggcttg gtccagcctg ggggtccct gagactctcc      60 tgtactgcct ctggattctc cctcagtagg tactacatga cctgggtccg ccaggctcca    120
gggaaggggc tggagtggat cggaaccatt tatactagtg gtagtacatg gtacgcgagc    180
tggacaaaag gcagattcac catctccaaa gacaatacca gaacacggt ggatcttcaa    240
```

```
atgaacagcc tgagagccga ggacacggct gtgtattact gtgcgagatc ctattatggc    300
ggtgataaga ctggtttagg catctggggc agggaactc tggttaccgt ctcttca       357
```

<210> SEQ ID NO 34
<211> LENGTH: 119
<212> TYPE: PRT
<213> ORGANISM: Artificial Sequence
<220> FEATURE:
<223> OTHER INFORMATION: synthesized

<400> SEQUENCE: 34

```
Gln Ser Leu Val Glu Ser Gly Gly Gly Leu Val Gln Pro Gly Gly Ser
 1               5                  10                  15

Leu Arg Leu Ser Cys Thr Ala Ser Gly Phe Ser Leu Ser Arg Tyr Tyr
                20                  25                  30

Met Thr Trp Val Arg Gln Ala Pro Gly Lys Gly Leu Glu Trp Ile Gly
            35                  40                  45

Thr Ile Tyr Thr Ser Gly Ser Thr Trp Tyr Ala Ser Trp Thr Lys Gly
        50                  55                  60

Arg Phe Thr Ile Ser Lys Asp Asn Thr Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Ser Tyr Tyr Gly Gly Asp Lys Thr Gly Leu Gly Ile Trp Gly Gln Gly
               100                 105                 110

Thr Leu Val Thr Val Ser Ser
           115
```

<210> SEQ ID NO 35
<211> LENGTH: 339
<212> TYPE: DNA
<213> ORGANISM: Artificial Sequence
<220> FEATURE:
<223> OTHER INFORMATION: synthesized

<400> SEQUENCE: 35

```
gacatccaga tgacccagtc tccttccacc ctgtctgcat ctgtaggaga cagagtcacc    60
atcacttgcc aggccagtca gagcattgat agttggttat cctggtatca gcagaaacca   120
gggaaagccc ctaagctcct gatctatcag gcatccactc tggcatctgg ggtcccatca   180
aggttcagcg gcagtggatc tgggacagag ttcactctca ccatcagcag cctgcagcct   240
gatgattttg caacttatta ctgccaatct gcttatggtg ttagtggtac tagtagttat   300
ttatatactt tcggcggagg gaccaaggtg gagatcaaa                          339
```

<210> SEQ ID NO 36
<211> LENGTH: 113
<212> TYPE: PRT
<213> ORGANISM: Artificial Sequence
<220> FEATURE:
<223> OTHER INFORMATION: synthesized

<400> SEQUENCE: 36

```
Asp Ile Gln Met Thr Gln Ser Pro Ser Thr Leu Ser Ala Ser Val Gly
 1               5                  10                  15

Asp Arg Val Thr Ile Thr Cys Gln Ala Ser Gln Ser Ile Asp Ser Trp
                20                  25                  30

Leu Ser Trp Tyr Gln Gln Lys Pro Gly Lys Ala Pro Lys Leu Leu Ile
            35                  40                  45
```

Tyr Gln Ala Ser Thr Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Ala Tyr Val Ser Gly
                85                  90                  95

Thr Ser Ser Tyr Leu Tyr Thr Phe Gly Gly Gly Thr Lys Val Glu Ile
            100                 105                 110

Lys

<210> SEQ ID NO 37
<211> LENGTH: 366
<212> TYPE: DNA
<213> ORGANISM: Artificial Sequence
<220> FEATURE:
<223> OTHER INFORMATION: synthesized

<400> SEQUENCE: 37
gaggtgcagc tgttggagtc tgggggaggc ttggtacagc ctgggggtc cctgagactc       60 tcctgtgcag cctctggatt caccatcagt cgctaccaca tgacttgggt ccgccaggct     120
ccagggaagg ggctggagtg gatcggacat atttatgtta ataatgatga cacagactac     180
gcgagctccg cgaaaggccg gttcaccatc tccagagaca attccaagaa cacgctgtat     240
ctgcaaatga acagcctgag agccgaggac acggccacct atttctgtgc gagattggat     300
gttggtggtg gtggtgctta tattggggac atctggggcc agggaactct ggttaccgtc     360
tcttca                                                                366

<210> SEQ ID NO 38
<211> LENGTH: 122
<212> TYPE: PRT
<213> ORGANISM: Artificial Sequence
<220> FEATURE:
<223> OTHER INFORMATION: synthesized

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Arg Tyr
            20                  25                  30

His Met Thr Trp Val Arg Gln Ala Pro Gly Lys Gly Leu Glu Trp Ile
        35                  40                  45

Gly His Ile Tyr Val Asn Asn Asp Asp Thr Asp Tyr Ala Ser Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Phe Cys
                85                  90                  95

Ala Arg Leu Asp Val Gly Gly Gly Gly Ala Tyr Ile Gly Asp Ile Trp
            100                 105                 110

Gly Gln Gly Thr Leu Val Thr Val Ser Ser
        115                 120

<210> SEQ ID NO 39
<211> LENGTH: 339
<212> TYPE: DNA
<213> ORGANISM: Artificial Sequence
<220> FEATURE:

<223> OTHER INFORMATION: synthesized

<400> SEQUENCE: 39

```
gacatccaga tgacccagtc tccatcctcc ctgtctgcat ctgtaggaga cagagtcacc    60
atcacttgcc agtccagtca gagtgtttat aacaacaacg acttagcctg gtatcagcag   120
aaaccaggga agttcctaa gctcctgatc tattatgctt ccactctggc atctggggtc   180
ccatctcggt tcagtggcag tggatctggg acagatttca ctctcaccat cagcagcctg   240
cagcctgaag atgttgcaac ttattactgt gcaggcggtt atgatacgga tggtcttgat   300
acgtttgctt cggcggagg gaccaaggtg gagatcaaa                           339
```

<210> SEQ ID NO 40
<211> LENGTH: 113
<212> TYPE: PRT
<213> ORGANISM: Artificial Sequence
<220> FEATURE:
<223> OTHER INFORMATION: synthesized

<400> SEQUENCE: 40

```
Asp Ile Gln Met Thr Gln Ser Pro Ser Ser Leu Ser Ala Ser Val Gly
1               5                   10                  15
Asp Arg Val Thr Ile Thr Cys Gln Ser Ser Gln Ser Val Tyr Asn Asn
            20                  25                  30
Asn Asp Leu Ala Trp Tyr Gln Gln Lys Pro Gly Lys Val Pro Lys Leu
        35                  40                  45
Leu Ile Tyr Tyr Ala Ser Thr Leu Ala Ser Gly Val Pro Ser Arg Phe
    50                  55                  60
Ser Gly Ser Gly Ser Gly Thr Asp Phe Thr Leu Thr Ile Ser Ser Leu
65                  70                  75                  80
Gln Pro Glu Asp Val Ala Thr Tyr Tyr Cys Ala Gly Gly Tyr Asp Thr
                85                  90                  95
Asp Gly Leu Asp Thr Phe Ala Phe Gly Gly Gly Thr Lys Val Glu Ile
            100                 105                 110
Lys
```

<210> SEQ ID NO 41
<211> LENGTH: 345
<212> TYPE: DNA
<213> ORGANISM: Artificial Sequence
<220> FEATURE:
<223> OTHER INFORMATION: synthesized

<400> SEQUENCE: 41

```
gaggtgcagc tggtggagtc tgggggaggc ttggtccagc ctggggggtc cctgagactc    60
tcctgtactg cctctggatt ctccctcagt agctatgcaa tgagctgggt ccgccaggct   120
ccagggaggg gctggagtg gatcggaatc atttatgcta gtggtagcac atactacgcg   180
agctcggcga aaggcagatt caccatctcc aaagacaata ccaagaacac ggtggatctt   240
caaatgaaca gcctgagagc cgaggacacg gctgtgtatt actgtgcgag aatttatgac   300
ggcatggacc tctggggcca gggaactctg gttaccgtct cttca                   345
```

<210> SEQ ID NO 42
<211> LENGTH: 115
<212> TYPE: PRT
<213> ORGANISM: Artificial Sequence
<220> FEATURE:
<223> OTHER INFORMATION: synthesized

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Arg Gly Leu Glu Trp Ile
        35                  40                  45

Gly Ile Ile Tyr Ala Ser Gly Ser Thr Tyr Tyr Ala Ser Ser Ala Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Ile Tyr Asp Gly Met Asp Leu Trp Gly Gln Gly Thr Leu Val Thr
            100                 105                 110

Val Ser Ser
        115

<210> SEQ ID NO 43
<211> LENGTH: 321
<212> TYPE: DNA
<213> ORGANISM: Artificial Sequence
<220> FEATURE:
<223> OTHER INFORMATION: synthesized

<400> SEQUENCE: 43
gacatccaga tgacccagtc tccatcctcc ctgtctgcat ctgtaggaga cagagtcacc      60
atcaattgcc aggccagtca gaacatttac agctactcat cctggtatca gcagaaacca    120
gggaaagttc ctaagcgcct gatctatctg catcactc tggcatctgg ggtcccatct      180
cggttcagtg gcagtggatc tgggacagat tacactctca ccatcagcag cctgcagcct    240
gaagatgttg caacttatta ctgtcaaagc aattataacg gtaattatgg tttcggcgga    300
gggaccaagg tggagatcaa a                                               321

<210> SEQ ID NO 44
<211> LENGTH: 107
<212> TYPE: PRT
<213> ORGANISM: Artificial Sequence
<220> FEATURE:
<223> OTHER INFORMATION: synthesized

<400> SEQUENCE: 44

Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Asn Ile Tyr Ser Tyr
            20                  25                  30

Leu Ser Trp Tyr Gln Gln Lys Pro Gly Lys Val Pro Lys Arg Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Ser Asn Tyr Asn Gly Asn Tyr
                85                  90                  95

Gly Phe Gly Gly Gly Thr Lys Val Glu Ile Lys
            100                 105

<210> SEQ ID NO 45
<211> LENGTH: 360
<212> TYPE: DNA
<213> ORGANISM: Artificial Sequence
<220> FEATURE:
<223> OTHER INFORMATION: synthesized

<400> SEQUENCE: 45

```
gaggtgcagc tggtggagtc tgggggaggc ttggtccagc ctgggggtc cctgagactc        60 tcctgtgcag cctctggatt ctccctcaat aactactgga tgagctgggt ccgccaggct      120
ccagggaagg ggctggagtg gatcggaacc attagtagtg gtgcgtatac atggttcgcc      180
acctgggcga caggcagatt caccatctcc agagacaatt ccaagaacac gctgtatctt      240
caaatgaaca gcctgagagc cgaggacacg gctgtgtatt actgtgcgag atattcttct      300
actactgatt ggacctactt taacatctgg ggccaggaa ctctggttac cgtctcttca      360
```

<210> SEQ ID NO 46
<211> LENGTH: 120
<212> TYPE: PRT
<213> ORGANISM: Artificial Sequence
<220> FEATURE:
<223> OTHER INFORMATION: synthesized

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Tyr
            20                  25                  30

Trp Met Ser Trp Val Arg Gln Ala Pro Gly Lys Gly Leu Glu Trp Ile
        35                  40                  45

Gly Thr Ile Ser Ser Gly Ala Tyr Thr Trp Phe Ala Thr Trp Ala Thr
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Ser Ser Thr Thr Asp Trp Thr Tyr Phe Asn Ile Trp Gly Gln
            100                 105                 110

Gly Thr Leu Val Thr Val Ser Ser
        115                 120

<210> SEQ ID NO 47
<211> LENGTH: 324
<212> TYPE: DNA
<213> ORGANISM: Artificial Sequence
<220> FEATURE:
<223> OTHER INFORMATION: synthesized

<400> SEQUENCE: 47

```
gacatccaga tgacccagtc tccttccacc ctgtctgcat ctgtaggaga cagagtcacc       60
atcacttgcc aggccagtca gagcattaat aactactag cctggtatca gcagaaacca      120
gggaaagccc ctaagctcct gatctatagg gcatccactc tggaatctgg ggtcccatca      180
aggttcagcg gcagtggatc tgggacagaa ttcactctca ccatcagcag cctgcagcct      240
gatgattttg caacttatta ctgccaaagc tataatggtg ttggtaggac tgctttcggc      300
ggagggacca aggtggagat caaa                                            324
```

<210> SEQ ID NO 48
<211> LENGTH: 108
<212> TYPE: PRT
<213> ORGANISM: Artificial Sequence
<220> FEATURE:
<223> OTHER INFORMATION: synthesized

<400> SEQUENCE: 48

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asn Gly Val Gly Arg
                85                  90                  95

Thr Ala Phe Gly Gly Gly Thr Lys Val Glu Ile Lys
            100                 105
```

<210> SEQ ID NO 49
<211> LENGTH: 348
<212> TYPE: DNA
<213> ORGANISM: Artificial Sequence
<220> FEATURE:
<223> OTHER INFORMATION: synthesized

<400> SEQUENCE: 49

```
gatgtgcagc ttcaggagtc gggacctagc ctggtgaaac cttctcagtc tctgtccctc      60
acctgcactg tcactggcta ctcaatcacc agtgattttg cctggaactg gattcggcag     120
tttccaggaa acaagctgga gtggatgggc tacataagtt atagtggtaa cactaggtac     180
aacccatctc tcaaaagtcg aatctctatc actcgcgaca catccaagaa ccaattcttc     240
ctgcagttga actctgtgac tattgaggac acagccacat attactgtgt aacggcggga     300
cgcgggtttc cttattgggg ccaagggact ctggtcactg tctctgca                  348
```

<210> SEQ ID NO 50
<211> LENGTH: 116
<212> TYPE: PRT
<213> ORGANISM: Artificial Sequence
<220> FEATURE:
<223> OTHER INFORMATION: synthesized

<400> SEQUENCE: 50

```
Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95
```

Val Thr Ala Gly Arg Gly Phe Pro Tyr Trp Gly Gln Gly Thr Leu Val
            100                 105                 110

Thr Val Ser Ala
        115

<210> SEQ ID NO 51
<211> LENGTH: 321
<212> TYPE: DNA
<213> ORGANISM: Artificial Sequence
<220> FEATURE:
<223> OTHER INFORMATION: synthesized

<400> SEQUENCE: 51
gacatcctga tgacccaatc tccatcctcc atgtctgtat ctctgggaga cacagtcagc    60
atcacttgcc attcaagtca ggacattaac agtaatatag gtggttgca gcagagacca   120 gggaaatcat ttaagggcct gatctatcat ggaaccaact tggacgatga agttccatca   180
aggttcagtg gcagtggatc tggagccgat tattctctca ccatcagcag cctggaatct   240
gaagattttg cagactatta ctgtgtacag tatgctcagt ttccgtggac gttcggtgga   300
ggcaccaagc tggaaatcaa a                                              321

<210> SEQ ID NO 52
<211> LENGTH: 107
<212> TYPE: PRT
<213> ORGANISM: Artificial Sequence
<220> FEATURE:
<223> OTHER INFORMATION: synthesized

<400> SEQUENCE: 52

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 53
<211> LENGTH: 363
<212> TYPE: DNA
<213> ORGANISM: Artificial Sequence
<220> FEATURE:
<223> OTHER INFORMATION: synthesized

<400> SEQUENCE: 53
gaggtgcagc tggtgcagtc tggagcagag gtgaagaaac caggagagtc tctgaagatc    60
tcctgtaagg gttctggata cagctttagc agttcatgga tcggctgggt gcgccaggca   120
cctgggaaag gcctggaatg gatggggatc atctatcctg atgactctga taccagatac   180
agtccatcct tccaaggcca ggtcaccatc tcagccgaca gtccatcag gactgcctac   240 ctgcagtgga gtagcctgaa ggcctcggac accgctatgt attactgtgc gagacatgtt   300

```
actatgattt gggagttat tattgacttc tggggccagg gaaccctggt caccgtctcc      360
tca                                                                   363
```

<210> SEQ ID NO 54
<211> LENGTH: 121
<212> TYPE: PRT
<213> ORGANISM: Artificial Sequence
<220> FEATURE:
<223> OTHER INFORMATION: synthesized

<400> SEQUENCE: 54

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
            20                  25                  30

Trp Ile Gly Trp Val Arg Gln Ala Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Asp Phe Trp Gly
            100                 105                 110

Gln Gly Thr Leu Val Thr Val Ser Ser
        115                 120
```

<210> SEQ ID NO 55
<211> LENGTH: 321
<212> TYPE: DNA
<213> ORGANISM: Artificial Sequence
<220> FEATURE:
<223> OTHER INFORMATION: synthesized

<400> SEQUENCE: 55

```
gccatccagt tgacccagtc tccatcctcc ctgtctgcat ctgtaggaga cagagtcacc       60
atcacttgcc gggcaagtca gggcattagc agtgctttag cctggtatca gcagaaacca      120
gggaaagctc ctaagctcct gatctatgat gcctccagtt tggaaagtgg ggtcccatca      180
aggttcagcg gcagtggatc tgggacagat ttcactctca ccatcagcag cctgcagcct      240
gaagattttg caacttatta ctgtcaacag tttaatagtt acccattcac tttcggccct      300
gggaccaaag tggatatcaa a                                                321
```

<210> SEQ ID NO 56
<211> LENGTH: 107
<212> TYPE: PRT
<213> ORGANISM: Artificial Sequence
<220> FEATURE:
<223> OTHER INFORMATION: synthesized

<400> SEQUENCE: 56

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45
```

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 57
<211> LENGTH: 354
<212> TYPE: DNA
<213> ORGANISM: Artificial Sequence
<220> FEATURE:
<223> OTHER INFORMATION: synthesized

<400> SEQUENCE: 57
gaggtgaagc tggatgagac tggaggaggc ttggtgcaac ctgggaggcc catgaaactc      60
tcctgtgttg cctctggatt cactttagt gactactgga tgaactgggt ccgccagtct     120
ccagagaaag gactggagtg ggtagcacaa attagaaaca aaccttataa ttatgaaaca     180
tattattcag attctgtgaa aggcagattc accatctcaa gagatgattc caaaagtagt     240
gtctacctgc aaatgaacaa cttaagagtt gaagacatgg gtatctatta ctgtacgggt     300
tcttactatg gtatggacta ctggggtcaa ggaacctcag tcaccgtctc ctca          354

<210> SEQ ID NO 58
<211> LENGTH: 118
<212> TYPE: PRT
<213> ORGANISM: Artificial Sequence
<220> FEATURE:
<223> OTHER INFORMATION: synthesized

<400> SEQUENCE: 58

Glu Val Lys Leu Asp Glu Thr Gly Gly Gly Leu Val Gln Pro Gly Arg
 1               5                  10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115

<210> SEQ ID NO 59
<211> LENGTH: 336
<212> TYPE: DNA
<213> ORGANISM: Artificial Sequence
<220> FEATURE:
<223> OTHER INFORMATION: synthesized

<400> SEQUENCE: 59

| | |
|---|---|
| gatgtcgtga tgacccaaac tccactctcc ctgcctgtca gtcttggaga tcaagcctcc | 60 |
| atctcttgca gatctagtca gagccttgta cacagtaatg gaaacaccta tttacgttgg | 120 |
| tacctgcaga agccaggcca gtctccaaag gtcctgatct acaaagtttc caaccgattt | 180 |
| tctggggtcc cagacaggtt cagtggcagt ggatcaggga cagatttcac actcaagatc | 240 |
| agcagagtgg aggctgagga tctgggagtt tatttctgct ctcaaagtac acatgttccg | 300 |
| tggacgttcg gtggaggcac caagctggaa atcaaa | 336 |

<210> SEQ ID NO 60
<211> LENGTH: 112
<212> TYPE: PRT
<213> ORGANISM: Artificial Sequence
<220> FEATURE:
<223> OTHER INFORMATION: synthesized

<400> SEQUENCE: 60

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 61
<211> LENGTH: 987
<212> TYPE: DNA
<213> ORGANISM: Artificial Sequence
<220> FEATURE:
<223> OTHER INFORMATION: synthesized

<400> SEQUENCE: 61

| | |
|---|---|
| gctagcacca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagag agttgagccc | 300 |
| aaatcttgtg acaaaactca cacatgccca ccgtgcccag cacctgaagc cgcggggggca | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |
| agcacgtacc gtgtggtcag cgtcctcacc gtcctgcacc aggactggct gaatggcaag | 600 |
| gagtacaagt gcgcggtctc caacaaagcc ctcccagccc ccatcgagaa aaccatctcc | 660 |
| aaagccaaag ggcagccccg agaaccacag gtgtacaccc tgcccccatc ccgggatgag | 720 |
| ctgaccaaga accaggtcag cctgacctgc ctggtcaaag gcttctatcc cagcgacatc | 780 |

```
gccgtggagt gggagagcaa tgggcagccg agaacaact acaagaccac gcctcccgtg    840
ctggactccg acggctcctt cttcctctat agcaagctca ccgtggacaa gagcaggtgg    900 cagcaggga acgtcttctc atgctccgtg atgcatgagg ctctgcacaa ccactacacg    960
cagaagagcc tctccctgtc tccgggt                                        987
```

```
<210> SEQ ID NO 62
<211> LENGTH: 329
<212> TYPE: PRT
<213> ORGANISM: Artificial Sequence
<220> FEATURE:
<223> OTHER INFORMATION: synthesized

<400> SEQUENCE: 62
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
```

<210> SEQ ID NO 63
<211> LENGTH: 321
<212> TYPE: DNA
<213> ORGANISM: Artificial Sequence
<220> FEATURE:
<223> OTHER INFORMATION: synthesized

<400> SEQUENCE: 63

```
cgtacggtgg ctgcaccatc tgtcttcatc ttcccgccat ctgatgagca gttgaaatct      60
ggaactgcct ctgttgtgtg cctgctgaat aacttctatc ccagagaggc aaagtacag     120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321
```

<210> SEQ ID NO 64
<211> LENGTH: 107
<212> TYPE: PRT
<213> ORGANISM: Artificial Sequence
<220> FEATURE:
<223> OTHER INFORMATION: synthesized

<400> SEQUENCE: 64

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 65
<211> LENGTH: 3681
<212> TYPE: DNA
<213> ORGANISM: Artificial Sequence
<220> FEATURE:
<223> OTHER INFORMATION: synthesized

<400> SEQUENCE: 65

```
gacatccaga tgacccagtc tccttccacc ctgtctgcat ctgtaggaga cagagtcacc      60
atcacttgcc agtccagtca gagtgtttat agtaactggt tctcctggta tcagcagaaa    120
ccagggaaag cccctaagct cctgatctat tctgcatcca ctctggcatc tggggtccca    180
tcaaggttca gcggcagtgg atctgggaca gaattcactc tcaccatcag cagcctgcag    240
cctgatgatt ttgcaactta ttactgcgca ggcggttaca atactgttat tgatactttt    300
gctttcggcg gagggaccaa ggtggagatc aaaggcggtg gcggtagtgg gggaggcggt    360
tctggcggcg gagggtccgg cggtggagga tcagaggtgc agctgttgga gtctggggga    420
```

```
ggcttggtac agcctggggg gtccctgaga ctctcctgtg cagcctctgg aatcgacttc    480
agtaggagat actacatgtg ctgggtccgc caggctccag ggaagggct ggagtggatc    540 gcatgcatat atactggtag ccgcgatact cctcactacg cgagctccgc gaaaggccgg    600
ttcaccatct ccagagacaa ttccaagaac acgctgtatc tgcaaatgaa cagcctgaga    660
gccgaggaca cggccgtata ttactgtgcg agagaaggta gcctgtgggg ccagggaacc    720
ctggtcaccg tctcgagcgg cggtggaggg tccggcggtg gtggatccca gtcggtggag    780
gagtctgggg gaggcttggt ccagcctggg gggtccctga ctctcctg tacagcctct    840 ggaatcgacc ttaataccta cgacatgatc tgggtccgcc aggctccagg caaggggcta    900
gagtgggttg gaatcattac ttatagtggt agtagatact acgcgaactg ggcgaaaggc    960
cgattcacca tctccaaaga cataccaag aacacggtgt atctgcaaat gaacagcctg    1020
agagctgagg acacggctgt gtattactgt gccagagatt atatgagtgg ttcccacttg    1080
tggggccagg gaaccctggt caccgtctct agtgctagca ccaagggccc atcggtcttc    1140
cccctggcac cctcctccaa gagcacctct ggggcacag cggccctggg ctgcctggtc    1200
aaggactact ccccgaacc ggtgacggtg tcgtggaact caggcgccct gaccagcggc    1260
gtgcacacct tcccggctgt cctacagtcc tcaggactct actccctcag cagcgtggtg    1320
accgtgccct ccagcagctt gggcacccag acctacatct gcaacgtgaa tcacaagccc    1380
agcaacacca aggtggacaa gagagttgag cccaaatctt gtgacaaaac tcacacatgc    1440
ccaccgtgcc cagcacctga gccgcgggg gcaccgtcag tcttcctctt ccccccaaaa    1500
cccaaggaca cctcatgat ctcccggacc cctgaggtca catgcgtggt ggtggacgtg    1560
agccacgaag accctgaggt caagttcaac tggtacgtgg acggcgtgga ggtgcataat    1620
gccaagacaa agccgcggga ggagcagtac aacagcacgt accgtgtggt cagcgtcctc    1680
accgtcctgc accaggactg gctgaatggc aaggagtaca agtgcgcggt ctccaacaaa    1740
gccctcccag cccccatcga gaaaaccatc tccaaagcca aagggcagcc ccgagaacca    1800
caggtgtata ccctgccccc atcccgggat gagctgacca agaaccaggt cagcctgacc    1860
tgcctggtca aaggcttcta tcccagcgac atcgccgtgg agtgggagag caatgggcag    1920
ccggagaaca actacaagac cacgcctccc gtgctggact ccgacggctc cttcttcctc    1980
tatagcaagc tcaccgtgga caagagcagg tggcagcagg ggaacgtctt ctcatgctcc    2040
gtgatgcatg aggctctgca caaccactac acgcagaaga gcctctccct gtctccgggt    2100
ggcggtggag gtccggcgg tggtggatcc gaggtgcagc tgttggagtc tgggggaggc    2160
ttggtacagc ctggggggtc cctgagactc tcctgtgcag cctctggatt caccatcagt    2220
cgctaccaca tgacttgggt ccgccaggct ccagggaagg gctggagtg gatcggacat    2280 atttatgtta ataatgatga cacagactac gcgagctccg cgaaaggccg gttcaccatc    2340
tccagagaca attccaagaa cacgctgtat ctgcaaatga acagcctgag agccgaggac    2400
acggccacct atttctgtgc gagattggat gttggtggtg gtggtgctta tattggggac    2460
atctggggcc aggaactct ggttaccgtc tcttcaggcg gtggcggtag tggggaggc    2520 ggttctggcg gcgagggtc cggcggtgga ggatcagaca tccagatgac ccagtctcca    2580
tcctccctgt ctgcatctgt aggagacaga gtcaccatca cttgccagtc cagtcagagt    2640
gtttataaca caacgactt agcctggtat cagcagaaac cagggaaagt tcctaagctc    2700
ctgatctatt atgcttccac tctggcatct ggggtcccat ctcggttcag tggcagtgga    2760
tctgggacag atttcactct caccatcagc agcctgcagc ctgaagatgt tgcaacttat    2820
```

```
tactgtgcag gcggttatga tacggatggt cttgatacgt ttgctttcgg cggagggacc    2880
aaggtggaga tcaaaggcgg tggagggtcc ggcggtggtg gatccgaggt gcagctggtg    2940
gagtctgggg gaggcttggt ccagcctggg gggtccctga actctcctg tgcagcctct     3000 ggattcacca tcagtaccaa tgcaatgagc tgggtccgcc aggctccagg gaaggggctg    3060
gagtggatcg gagtcattac tggtcgtgat atcacatact acgcgagctg gcgaaaggc     3120 agattcacca tctccagaga caattccaag aacacgctgt atcttcaaat gaacagcctg    3180
agagccgagg acacggctgt gtattactgt gcgcgcgacg tggatcatc tgctattact     3240 agtaacaaca tttggggcca aggaactctg gtcaccgttt cttcaggcgg tggcggtagt    3300
gggggaggcg gttctggcgg cggagggtcc ggcggtggag gatcagacgt cgtgatgacc    3360
cagtctcctt ccaccctgtc tgcatctgta ggagacagag tcaccatcaa ttgccaagcc    3420
agtgagagca ttagcagttg gttagcctgg tatcagcaga accagggaa agcccctaag     3480 ctcctgatct atgaagcatc caaactggca tctggggtcc catcaaggtt cagcggcagt    3540
ggatctggga cagagttcac tctcaccatc agcagcctgc agcctgatga ttttgcaact    3600
tattactgcc aaggctattt ttattttatt agtcgtactt atgtaaattc tttcggcgga    3660
gggaccaagg tggagatcaa a                                              3681
```

<210> SEQ ID NO 66
<211> LENGTH: 1227
<212> TYPE: PRT
<213> ORGANISM: Artificial Sequence
<220> FEATURE:
<223> OTHER INFORMATION: synthesized

<400> SEQUENCE: 66

```
Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys Gly
            100                 105                 110

Gly Gly Gly Ser Gly Gly Gly Ser Gly Gly Gly Ser Gly Gly
        115                 120                 125

Gly Gly Ser Glu Val Gln Leu Leu Glu Ser Gly Gly Gly Leu Val Gln
    130                 135                 140

Pro Gly Gly Ser Leu Arg Leu Ser Cys Ala Ala Ser Gly Ile Asp Phe
145                 150                 155                 160

Ser Arg Arg Tyr Tyr Met Cys Trp Val Arg Gln Ala Pro Gly Lys Gly
                165                 170                 175

Leu Glu Trp Ile Ala Cys Ile Tyr Thr Gly Ser Arg Asp Thr Pro His
            180                 185                 190

Tyr Ala Ser Ser Ala Lys Gly Arg Phe Thr Ile Ser Arg Asp Asn Ser
        195                 200                 205
```

Lys Asn Thr Leu Tyr Leu Gln Met Asn Ser Leu Arg Ala Glu Asp Thr
            210                 215                 220

Ala Val Tyr Tyr Cys Ala Arg Glu Gly Ser Leu Trp Gly Gln Gly Thr
225                 230                 235                 240

Leu Val Thr Val Ser Ser Gly Gly Gly Ser Gly Gly Gly Gly Ser
                245                 250                 255

Gln Ser Val Glu Glu Ser Gly Gly Leu Val Gln Pro Gly Gly Ser
            260                 265                 270

Leu Arg Leu Ser Cys Thr Ala Ser Gly Ile Asp Leu Asn Thr Tyr Asp
            275                 280                 285

Met Ile Trp Val Arg Gln Ala Pro Gly Lys Gly Leu Glu Trp Val Gly
290                 295                 300

Ile Ile Thr Tyr Ser Gly Ser Arg Tyr Tyr Ala Asn Trp Ala Lys Gly
305                 310                 315                 320

Arg Phe Thr Ile Ser Lys Asp Asn Thr Lys Asn Thr Val Tyr Leu Gln
                325                 330                 335

Met Asn Ser Leu Arg Ala Glu Asp Thr Ala Val Tyr Tyr Cys Ala Arg
                340                 345                 350

Asp Tyr Met Ser Gly Ser His Leu Trp Gly Gln Gly Thr Leu Val Thr
            355                 360                 365

Val Ser Ser Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Leu Gly
            435                 440                 445

Thr Gln Thr Tyr Ile Cys Asn Val Asn His Lys Pro Ser Asn Thr Lys
            450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Ala Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
            515                 520                 525

Phe Asn Trp Tyr Val Asp Gly Val Glu Val His Asn Ala Lys Thr Lys
530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Ala
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
            595                 600                 605

Arg Asp Glu Leu Thr Lys Asn Gln Val Ser Leu Thr Cys Leu Val Lys
610                 615                 620

```
Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
                660                 665                 670

Gln Gly Asn Val Phe Ser Cys Ser Val Met His Glu Ala Leu His Asn
                675                 680                 685

His Tyr Thr Gln Lys Ser Ser Leu Ser Pro Gly Gly Gly Gly
    690                 695                 700

Ser Gly Gly Gly Ser Glu Val Gln Leu Leu Glu Ser Gly Gly Gly
705                 710                 715                 720

Leu Val Gln Pro Gly Gly Ser Leu Arg Leu Ser Cys Ala Ala Ser Gly
                725                 730                 735

Phe Thr Ile Ser Arg Tyr His Met Thr Trp Val Arg Gln Ala Pro Gly
                740                 745                 750

Lys Gly Leu Glu Trp Ile Gly His Ile Tyr Val Asn Asn Asp Asp Thr
                755                 760                 765

Asp Tyr Ala Ser Ser Ala Lys Gly Arg Phe Thr Ile Ser Arg Asp Asn
770                 775                 780

Ser Lys Asn Thr Leu Tyr Leu Gln Met Asn Ser Leu Arg Ala Glu Asp
785                 790                 795                 800

Thr Ala Thr Tyr Phe Cys Ala Arg Leu Asp Val Gly Gly Gly Gly Ala
                805                 810                 815

Tyr Ile Gly Asp Ile Trp Gly Gln Gly Thr Leu Val Thr Val Ser Ser
                820                 825                 830

Gly Gly Gly Gly Ser Gly Gly Gly Ser Gly Gly Gly Gly Ser Gly
                835                 840                 845

Gly Gly Gly Ser Asp Ile Gln Met Thr Gln Ser Pro Ser Ser Leu Ser
850                 855                 860

Ala Ser Val Gly Asp Arg Val Thr Ile Thr Cys Gln Ser Ser Gln Ser
865                 870                 875                 880

Val Tyr Asn Asn Asn Asp Leu Ala Trp Tyr Gln Gln Lys Pro Gly Lys
                885                 890                 895

Val Pro Lys Leu Leu Ile Tyr Tyr Ala Ser Thr Leu Ala Ser Gly Val
                900                 905                 910

Pro Ser Arg Phe Ser Gly Ser Gly Ser Gly Thr Asp Phe Thr Leu Thr
                915                 920                 925

Ile Ser Ser Leu Gln Pro Glu Asp Val Ala Thr Tyr Tyr Cys Ala Gly
                930                 935                 940

Gly Tyr Asp Thr Asp Gly Leu Asp Thr Phe Ala Phe Gly Gly Gly Thr
945                 950                 955                 960

Lys Val Glu Ile Lys Gly Gly Gly Gly Ser Gly Gly Gly Gly Ser Glu
                965                 970                 975

Val Gln Leu Val Glu Ser Gly Gly Gly Leu Val Gln Pro Gly Gly Ser
                980                 985                 990

Leu Arg Leu Ser Cys Ala Ala Ser Gly Phe Thr Ile Ser Thr Asn Ala
                995                 1000                1005

Met Ser Trp Val Arg Gln Ala Pro Gly Lys Gly Leu Glu Trp Ile
        1010                1015                1020

Gly Val Ile Thr Gly Arg Asp Ile Thr Tyr Tyr Ala Ser Trp Ala
        1025                1030                1035

Lys Gly Arg Phe Thr Ile Ser Arg Asp Asn Ser Lys Asn Thr Leu
```

```
                    1040                1045                1050
Tyr Leu Gln Met Asn Ser Leu Arg Ala Glu Asp Thr Ala Val Tyr
            1055                1060                1065

Tyr Cys Ala Arg Asp Gly Gly Ser Ser Ala Ile Thr Ser Asn Asn
    1070                1075                1080

Ile Trp Gly Gln Gly Thr Leu Val Thr Val Ser Ser Gly Gly Gly
1085                1090                1095

Gly Ser Gly Gly Gly Gly Ser Gly Gly Gly Gly Ser Gly Gly Gly
    1100                1105                1110

Gly Ser Asp Val Val Met Thr Gln Ser Pro Ser Thr Leu Ser Ala
    1115                1120                1125

Ser Val Gly Asp Arg Val Thr Ile Asn Cys Gln Ala Ser Glu Ser
    1130                1135                1140

Ile Ser Ser Trp Leu Ala Trp Tyr Gln Gln Lys Pro Gly Lys Ala
1145                1150                1155

Pro Lys Leu Leu Ile Tyr Glu Ala Ser Lys Leu Ala Ser Gly Val
    1160                1165                1170

Pro Ser Arg Phe Ser Gly Ser Gly Ser Gly Thr Glu Phe Thr Leu
    1175                1180                1185

Thr Ile Ser Ser Leu Gln Pro Asp Asp Phe Ala Thr Tyr Tyr Cys
    1190                1195                1200

Gln Gly Tyr Phe Tyr Phe Ile Ser Arg Thr Tyr Val Asn Ser Phe
    1205                1210                1215

Gly Gly Gly Thr Lys Val Glu Ile Lys
    1220                1225
```

<210> SEQ ID NO 67
<211> LENGTH: 651
<212> TYPE: DNA
<213> ORGANISM: Artificial Sequence
<220> FEATURE:
<223> OTHER INFORMATION: synthesized

<400> SEQUENCE: 67

```
gcctatgata tgacccagtc tccatcttcc gtgtctgcat ctgtaggaga cagagtcacc    60
atcaagtgtc aggccagtga ggacatttat agcttcttgg cctggtatca gcagaaacca   120
gggaaagccc ctaagctcct gatccattct gcatcctctc tggcatctgg ggtcccatca   180
aggttcagcg gcagtggatc tgggacagat ttcactctca ccatcagcag cctgcagcct   240
gaagattttg caacttacta ttgtcaacag ggttatggta aaaataatgt tgataatgct   300
ttcggcggag ggaccaaggt ggagatcaaa cgtacggtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaag tctacgcctg cgaagtcacc   600
catcagggcc tgagctcgcc cgtcacaaag agcttcaaca ggggagagtg t            651
```

<210> SEQ ID NO 68
<211> LENGTH: 217
<212> TYPE: PRT
<213> ORGANISM: Artificial Sequence
<220> FEATURE:
<223> OTHER INFORMATION: synthesized

<400> SEQUENCE: 68

```
Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```